(12) United States Patent
Mathiowitz et al.

(10) Patent No.: US 9,238,011 B2
(45) Date of Patent: Jan. 19, 2016

(54) COMPOSITIONS, METHODS AND KITS FOR THERAPEUTIC TREATMENT WITH WET SPUN MICROSTRUCTURES

(71) Applicants: Brown University, Providence, RI (US); The Children's Mercy Hospital, Kansas City, MO (US)

(72) Inventors: Edith Mathiowitz, Brookline, MA (US); Danya Lavin, Providence, RI (US); Richard Hopkins, Kansas City, MO (US)

(73) Assignee: Brown University, Providence, RI (US)

( * ) Notice: Subject to any disclaimer, the term of this patent is extended or adjusted under 35 U.S.C. 154(b) by 97 days.

(21) Appl. No.: 13/836,560

(22) Filed: Mar. 15, 2013

(65) Prior Publication Data

US 2013/0280319 A1     Oct. 24, 2013

Related U.S. Application Data

(63) Continuation-in-part of application No. PCT/US2012/048860, filed on Jul. 30, 2012.

(60) Provisional application No. 61/636,877, filed on Apr. 23, 2012.

(51) Int. Cl.
| | |
|---|---|
| *A61K 9/70* | (2006.01) |
| *A61K 47/34* | (2006.01) |
| *A61L 27/26* | (2006.01) |
| *A61L 27/54* | (2006.01) |
| *A61L 17/00* | (2006.01) |
| *A61L 17/04* | (2006.01) |
| *A61L 17/12* | (2006.01) |

(52) U.S. Cl.
CPC . *A61K 9/70* (2013.01); *A61K 47/34* (2013.01); *A61L 17/005* (2013.01); *A61L 17/04* (2013.01); *A61L 17/12* (2013.01); *A61L 27/26* (2013.01); *A61L 27/54* (2013.01); *A61L 2300/43* (2013.01)

(58) Field of Classification Search
CPC ....... A61L 27/26; A61L 17/04; A61L 17/005; A61L 17/12; A61L 2300/43; A61L 27/54; A61K 9/70; A61K 47/34; C08L 39/06; C08L 67/04

See application file for complete search history.

(56) References Cited

U.S. PATENT DOCUMENTS

| | | | |
|---|---|---|---|
| 4,965,128 A | 10/1990 | Greidanus et al. | |
| 7,029,700 B2 | 4/2006 | Mathiowitz et al. | |
| 8,043,553 B1 * | 10/2011 | Durcan | 264/573 |
| 2004/0086544 A1 | 5/2004 | Bezemer et al. | |
| 2006/0276385 A1 * | 12/2006 | Jo | 514/12 |
| 2007/0202150 A1 | 8/2007 | Dave | |

FOREIGN PATENT DOCUMENTS

WO    WO 2011007352 A2 *   1/2011

OTHER PUBLICATIONS

Venkatesaran et al. "Production of Anti-Fibroblast Growth Factor Receptor Monoclonal Antibodies by In Vitro Immunization" Hybridoma 1992, 11(6) 729-739, 1992.
Williamson et al. "Gravity spun polycaprolactone fibres: controlling release of hydrophylic macromolecule (ovalbumin) and a lipophilic drug (progesterone)" 2004 Biomaterials 25:5053-5060.
Williamson et al. "Gravity Spun Polycaprolactone Fibers for Applications in Vascular Tissue Engineering: Proliferation and Function of Human Vascular Endothelial Cells" Tissue Eng 2006; 12(1):45-51.
Williamson et al. "Gravity spinning of polycaprolactone fibres for applications in tissue engineering" Biomaterials, 2004; 25:459-465.
Xiang et al. "Structure and properties of polyimide (BTDA-TDI/MDI co-polyimide) fibers obtained by wet-spinning" Macromol Res, 2011; 19:645-653.
Yilgor et al. "Incorporation of a sequential BMP-2/BMP-7 delivery system into chitosan-based scaffolds for bone tissue engineering" Biomaterials 2009; 30(21):3551-9.
Zong et al. "Structure and morphology changes during in vitro degradation of electrospun poly(glycolide-co-lactide) nanofiber membrane" Biomacromolecules, 2003; 4:416-423.
Zurita et al. "Loading and release of ibuprofen in multi-and monofilament surgical sutures" Macromol Biosci 2006; 6(9):767-775.
Arbab et al. "Simultaneous effects of polymer concentration, jet-stretching, and hot-drawing on microstructural development of wet-spun poly(acrylonitrile) fibers" Polym Bull, 2011; 66:1267-1280.
Barcia et al. "Downregulation of endotoxin-induced uveitis by intravitreal injection of polylactic-glycolic acid (PLGA) microspheres loaded with dexamethasone" Exp Eye Res 2009; 89:238-245.
Blaker et al. Biomaterials "Development and characterization of silver-doped bioactive glass-coated sutures for tissue engineering and wound healing applications" Biomaterials 2004 25(7-8): 1319-1329.
Cao et al. "The topographical effect of electrospun nanofibrous scaffolds on the in vivo and in vitro foreign body reaction" J. Biomed. Mater. Res. A, 2009 pp. 1151-1159.
Chang et al. "Controlled release of an antibiotic, gentamicin sulphate, from gravity spun polycaprolactone fibers" J Biomed Mater Res Part A, 2008; 84:230-237.

(Continued)

*Primary Examiner* — Abigail Fisher
(74) *Attorney, Agent, or Firm* — Lawson & Weitzen LLP; Sonia K. Guterman; Preeti T. Arun

(57) ABSTRACT

Methods, compositions, systems, devices and kits are provided for preparing and using a multi-layer polymeric microstructure composition for delivering a therapeutic agent to a subject. In various embodiments, the therapeutic agent includes at least one selected from the group of: a drug, a protein, a sugar, a carbohydrate, and a nucleotide sequence. In related embodiments, the composition is a fiber, a suture, a sphere, an implant, or a scaffold.

26 Claims, 36 Drawing Sheets

(56) References Cited

OTHER PUBLICATIONS

Figure 1:
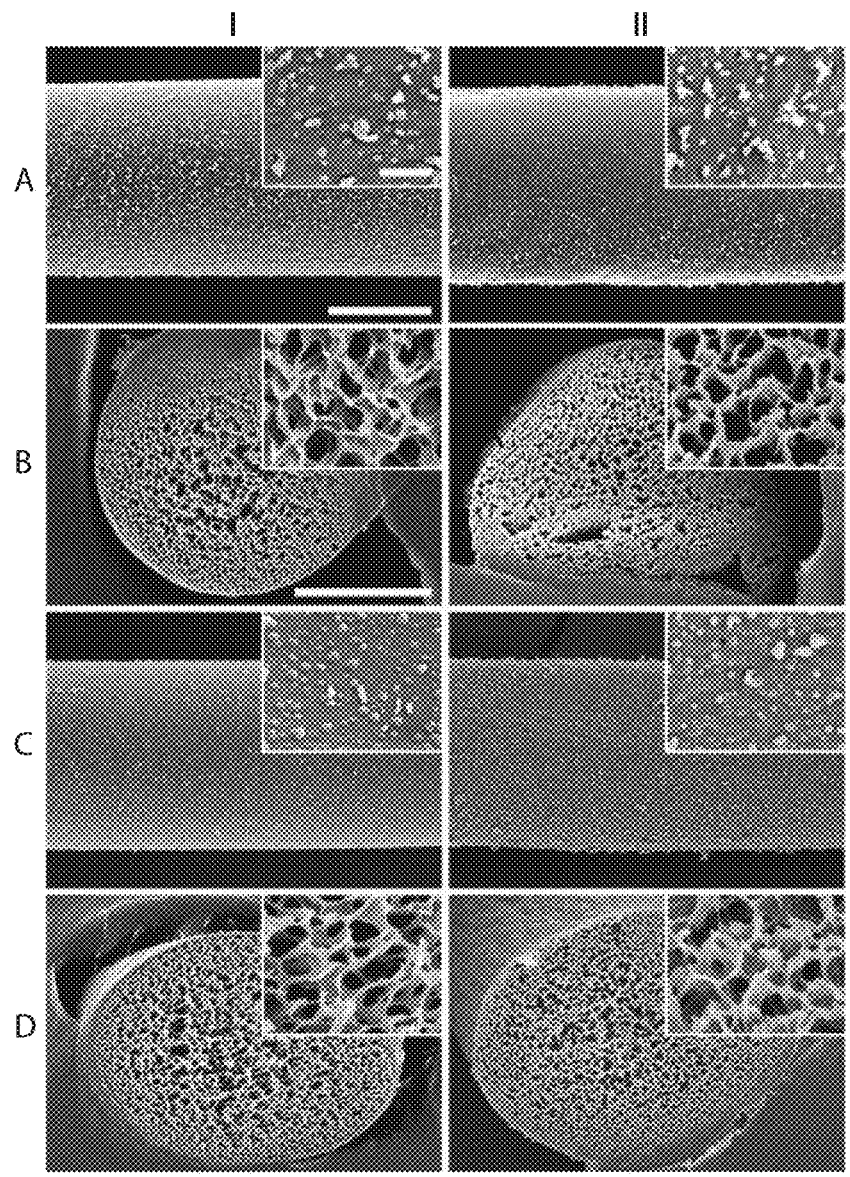

Chiang et al. "Weaving genetically engineered functionality into mechanically robust virus fibers" Adv Mater 2007; 19(6): 826-827.
Cohen et al. "Structure formation and phase-transformations in solutions of a rigid polymer" Acs Sym Ser, 1987; 350:181-98.
Cronin et al. "Protein-coated poly(L-lactic acid) fibers provid a substrate for differentiation of human skeletal muscular cells" J Biomed Mater Res A 2004;69(3): 373-381.
Crow et al. "Release of bovine serum albumin from a hydrogel-cored biodegradable polymer fiber" Biopolymers, 2006;81:419-427.
Crow et al. "Evaluation of in vitro drug release, pH change, and molecular weight degradation of poly(L-lactic acid) and poly(d, L-lactide-co-glycolide) fibers" Tissue Eng, 2005;11:1077-1084.
International Search Report and Written Opinion of the International Searching Authority mailed Feb. 15, 2013 in PCT/US12/48860 (11 pages).
Dang et al. "Spatiotemporal effects of a controlled-release anti-inflammatory drug on the cellular dynamics of host response" Biomaterials, 2011; 32:4464-4470.
Fischer et al. "Investigation of structure of solution grown crystals of lactide copolymers by means of chemical-reactions" Kolloid Z Z Polym, 1973; 251:980-990.
Gao et al. "The implantable 5-fluorouracil-loaded poly(L-lactic acid) and poly (L-lactic acid) fibers prepared by wet-spinning from suspension" J Control Release, 2007; 118:325-332.
Graessley "Molecular entanglement theory of flow behavior in amorphous polymers" J Chem Phys, 1965, 43:2696-2703.
Gramaglia et al. "High speed DSC (hyper-DSC) as a tool to measure the solubility of a drug within a solid or semi-solid matrix" Int J Pharm, 2005; 301:1-5.
Gupta et al. "Poly(lactic acid) fiber: An overview" Prog Polym Sci 2007, 32:455-482.
Harada et al. "Monoclonal antibody G6K12 specific for membrane-associated differentiation marker of human stratified squamous epithelia and squamous cell carcinoma" 1993, J. Oral Pathol. Med., 22(4):145-152.
Hickey et al. "In vivo evaluation of a dexamethasone/PLGA microsphere system designed to suppress the inflammatory tissue response to implantable medical devices" J Biomed Mater Res, 2002; 61:180-187.
Hirano et al. "Release of glycosaminoglycans in physiological salie and water by wet-spun chitin-acid glycosaminoglycan fiberts" J Biomed Mater Res 2001; 56(4): 556-561.
Hwang et al. "Microfluidic chip-based fabrication of PLGA microfiber scaffolds for tissue engineering" Langmuir 2008; 24(13): 6845-6851.
Inai, et al. "Immunohistochemical detection of an enamel protein-related epitope in rat bone at an early stage of osteogenesis" Histochemistry 1993, 99(5):335 362.
Jung et al. "Controlled release of cell-permeable gene complex from poly(L-lactide) scaffold for enhanced stem cell tissue engineering" J Control Release 2011, (152) 294-302.
Katz et al "Bacterial adherence to surgical sutures. A possible factor in suture induced infection" Ann Surg 1981; 194, 35-41.
Kim et al. "Incorporation and controlled release of a hydrophilic antibiotic using poly(lactide-co-glycolide)-based electrospun nanofibrous scaffolds" J Control Release 2004; 98(1):47-56.
Lavin et al. "A novel wet extrusion technique to fabricate self-assembled microfiber scaffolds for controlled drug delivery" J Biomed Mater Res A. Oct. 2012; 100(10):2793-802.
Lavin et al. "Multifunctional polymeric microfibers with prolonged drug delivery and structure support capabilities" E. Acta Biomater. May 2012; 8(5):1891-1900.
Lavin et al. "Effects of protein molecular weight on the intrinsic material properties and release kinetics of wet spun polymeric microfiber delivery systems" Acta Biomater Jan. 2013; 9(1):4569-78.
Leung et al., "Biomedical applications of nanofibers" Polym Advan Technol, 2011; 22:350-365.
Mack et al. "A biodegradable filament for controlled drug delivery" J Control Release, 2009; 139:205-211.
Mathiowitz et al. "Biologically erodable microspheres as potential oral drug delivery systems" Nature, 1997; 386:410-414.
Mulder et al. "Characterization of Two Human Monoclonal Antibodies Reactive with HLA-B60, respectively, Raised by in vitro Secondary Immunization of Peripheral Blood Lymphocytes" Hum. Immunol., 1993 36(3):186-192.
Nelson et al. "Technique paper for wet-spinning poly(L-lactic acid) and poly(DL-lactide-co-glycolide) monofilament fibers" Tissue Engineering, 2003; 9:1323-1330.
Pasternak et al. "Doxycycline-coated sutures improve mechanical strength of intestinal anastomoses" Int J Colorectal Dis 2008; 23(3): 271-276.
Patil et al."Dexamethasone-loaded poly(lactic-co-glycolic) acid microspheres/poly(vinyl alcohol) hydrogel composite coatings for inflammation control" Diabetes Technol Ther, 2004; 6:887-897.
Pekarek et al. "Double-walled polymer microspheres for controlled drug release" 1994; Nature 367:258-260.
Rahman et al. "Localization of Bovine Serum albumin in double-walled microspheres" 2004, Journal of Controlled Release 94:163-175.
Reil et al. "Dexamethasone Suppresses Vascular Smooth Muscle Cell Proliferation" J Surg Res, 1999;85:109-114.
Rissanen et al. "Effect of protein-loading on properties of wet-spun poly(L, D-lactide) multifilament fibers" J Appl Polym Sci 2010; 116(4):2174-2180.
Rissanen et al. "Solubility and phase separation of poly(L, D-lactide) copolymers" J Appl Polym Sci, 2008; 110:2399-2404.
Rissanen et al. "Effect of process parameters on properties of wet-spun poly(L, D-lactide) copolymer multifilament fibers" J Appl Polym Sci, 2009; 113:2683-2692.
Schakenraad et al. "Biodegradable hollow fibres for the controlled release of drugs" Biomaterials 1988 (9), 116-120.
Selvam et al. "Minimally invasive, longitudinal monitoring of biomaterial-associated inflammation by fluorescence imaging" Biomaterials, 2011; 32, 7785-7792.
Shibuya et al. "Covalent linking of proteins and cytokines to suture: enhancing the immune response of head and neck cancer patients" Laryngoscope 2003 113(11):1870-1884.
Sobhanipour et al. "Thermoporometry study of coagulation bath temperature effect on polyacrylonitrile fibers morphology" Thermochim Acta, 2011; 518:101-106.
Stäuber et al. "Rapid generation of monoclonal antibody-secreting hybridomas against African horse sickness virus by in vitro immunization and the fusion/cloning technique" J. Immunol. Methods, 1993, 161(2):157-168.
Su SH et al. "Curcumin impregnation improves the mechanical properties and reduces the inflammatory response associated with poly (L-lactic acid) fiber" J Biomat Sci-Polym, E 2005;16:353-370.
Sukitpaneenit et al. "Molecular elucidation of morphology and mechanical properties of PVDF hollow fiber membranes from aspects of phase inversion, crystallization and rheology" J Membrane Sci, 2009; 340 :192-205.
Tsuji et al. "Stereocomplex formation between enantiomeric poly(lactic acid)s. 5. Calorimetric and morphological studies on the stereocomplex formed in acetonitrile solution Macromolecules" 1992; 25:2940-2946.
Tuzlakoglu et al. "Biodegradable polymeric fiber structures in tissue engineering" Tissue Eng Part B Rev 2009; 15(1):17-27.

* cited by examiner

COMPOSITIONS, METHODS AND KITS FOR THERAPEUTIC TREATMENT WITH WET SPUN MICROSTRUCTURES

RELATED APPLICATION

This application claims the benefit of provisional application Ser. No. 61/636,877 filed Apr. 23, 2012, and international application serial number PCT/US12/48860 filed Jul. 30, 2012, both entitled, "Methods, compositions and kits for therapeutic treatment with wet spun binary phase microstructures", both having inventors Edith Mathiowitz, Danya Lavin and Richard Hopkins, which are hereby incorporated herein by reference in their entireties.

GOVERNMENT FUNDING

A portion of this work was supported by the National Science Foundation Materials Research Science & Engineering Program (DMR 0520651). The government has certain rights in this invention.

TECHNICAL FIELD

Systems, compositions, methods and kits are provided for preparing and using multi-layer polymeric microstructure system for controlled therapeutic agent delivery.

BACKGROUND

The delivery of hydrophilic therapeutics from small diameter wet spun microfibers is often characterized by an initial burst due to drug trapped on the surface during encapsulation (Williamson et al. 2004 Biomaterials 25:5053-5060; Change et al. 1998 Journal of Biomedical Research Part A 84A: 230-237). Rapid drug burst from microfibers is detrimental under the circumstances of a drug having a narrow therapeutic range, thereby resulting in local drug concentrations that quickly become toxic, and little advancement has been made to slow the release of therapeutics from wet spun microfiber-based delivery systems (Schakenraad et al. 1994 Biomaterials 367: 258-260). Previous work addressed double-walled microspheres with drug localized to inner or outer core for controlled release kinetics (Rahman et al. 2003 Journal of Controlled Release 94:163-175; Pekarek et al. 1994 Nature, 367:258-260). There is an urgent need for microencapsulation and phase separation techniques which slow the release of therapeutics from wet spun microfiber-based drug delivery systems.

SUMMARY

Compositions, methods and kits are provided for multi-functional polymeric microfibers with prolonged drug delivery and structural support capabilities.

An embodiment of the invention provides a wet spun microfiber composition having at least one polymer such that the composition includes a porous multi-layer polymeric microstructure, and further includes at least one encapsulated therapeutic agent, such that the therapeutic agent is located in an inner core of the microstructure and is controllably releasable from the composition, and such that the microfiber has a degree of crystallinity at least 10% greater than that of control polymer prior to wet spinning. In a related embodiment of the composition the polymeric microstructure is multi-layered. In other embodiments of the composition, the at least one encapsulated therapeutic agent is located in an inner core of the multi-layered microstructure.

In various embodiments the composition has a structure selected from the group of: a fiber, a suture, a sphere, an implant, and a scaffold.

In related embodiments of the composition an encapsulated first therapeutic agent is dexamethasone. Various embodiments of the composition further include an encapsulated second therapeutic agent. For example, the second therapeutic agent includes at least one selected from the group of a drug; a protein, for example, Nog (Noggin); a peptide; a sugar; a carbohydrate; and a nucleotide sequence. For example, the nucleotide sequence includes a vector. In related embodiments the protein is at least one selected-from the group of: a growth factor, an immunoglobulin, an enzyme, and a peptide antibiotic.

In various embodiments of the composition the polymers are at least one of poly-1-lactic acid (PLLA), poly-lactic-co-glycolide (PLGA) and polyvinylpyrrolidone (PVP).

According to an aspect of the invention, the composition comprises at least about 75% of the initial tensile strength for at least about five weeks.

Another embodiment of the invention provides a method of producing a wet spun microfiber composition having a porous multi-layer polymeric microstructure including the steps of mixing at least one polymer and at least one therapeutic agent with a solvent to form a solution; and wet spinning the material by phase inversion, thereby producing the microstructure, such that the composition has a degree of crystallinity which is at least 10% greater than that of control polymer prior to wet spinning.

In various embodiments of the method a first therapeutic agent is dexamethasone. Related embodiments of the method further include mixing the polymer solution with a second therapeutic agent prior to wet spinning. For example, the second therapeutic agent is selected from the group of: a protein a peptide, a sugar, a carbohydrate, a nucleotide sequence, and a drug, for example, an anti-apoptotic; an immunosuppressant; a pro-apoptotic; an anti-coagulant; an anti-tumor; an anti-viral; an anti-bacterial; an anti-mycobacterial; an anti-fungal; an anti-proliferative; and an anti-inflammatory, for example, a steroid selected from the group of: a cortisone compound, for example a dexamethasone, and a sex-related hormone; and a non-steroidal anti-inflammatory agent (NSAID).

In related embodiments of the method the solvent includes at least one of dichloromethane and tetrahydrofuran.

In embodiments of the method, wet spinning includes loading the material into a syringe, and dispensing the material into a coagulation bath, such that the coagulation bath includes a non-solvent, thereby obtaining phase inversion. For example, the coagulation bath includes petroleum ether.

Embodiments of the method include selecting the solvent and the non-solvent having different solubility parameters, such that the difference between the solubility parameters affects the rate of solidification of the polymer, the extent of solvent induced crystallization of the polymer, and the degree of crystallinity of the composition. The difference between the solubility parameter of the solvent and the solubility parameter of the non-solvent is selected from one of the following: less than about 12 units, less than about 10 units, less than about 9 units, less than about 8 units, less about than 7 units, less than about 6 units, less than about 5 units, less than about 4 units, less than about 3 units, less than about 2 units and less than about 1 unit. In various embodiments, the difference is less than about 2-4 units, less than about 4-6 units, less than about 6-8 units, or less than about 8-10 units.

In various embodiments, the difference is varied to modulate rate of crystallization of the composition. In a related embodiment, the polymers include a polymer matrix or a composite material. For example, the polymer matrix is bioabsorbable.

Another embodiment of the invention is a method of treating a subject having a medical condition including, contacting the subject with a wet spun microfiber composition having at least one polymer such that the composition includes a porous multi-layer polymeric microstructure, and further includes at least one encapsulated therapeutic agent, such that the therapeutic agent is located in an inner core of the microstructure and is controllably releasable from the composition, and such that the microfiber has a degree of crystallinity at least 10% greater than that of control polymer prior to wet spinning. For example, the medical condition is at least one selected from the group of a burn, an abrasion, a laceration, a pathology, a cancer, and an infection.

In related embodiments of the method of treating the subject, a first encapsulated therapeutic agent is dexamethasone. In various other embodiments, the method further includes an encapsulated second therapeutic agent. For example, the second therapeutic agent is at least one selected from the group of: a sugar; a carbohydrate; a nucleotide sequence; a protein selected from the group of: a growth factor, an immunoglobulin, an enzyme, and an antibiotic; and a drug, for example, an anti-apoptotic; an immunosuppressant; a pro-apoptotic; an anti-coagulant; an anti-tumor; an anti-viral; an anti-bacterial; an anti-mycobacterial; an anti-fungal; an anti-proliferative; and an anti-inflammatory, for example, a steroid selected from the group of a cortisone compound, for example a dexamethasone, and a sex-related hormone; and a non-steroidal anti-inflammatory agent (NSAID). For example the nucleotide sequence comprises a vector. For example the vector is a viral or a bacterial vector.

According to various embodiments of the method for treating the subject, the composition has a structure selected from the group of a fiber, a suture, a sphere, an implant, and a scaffold. In related embodiments, the polymers are at least one of poly-1-lactic acid (PLLA), poly-lactic-co-glycolide (PLGA) and polyvinylpyrrolidone (PVP).

Another aspect of the invention provides a kit for treating a subject having a medical condition including a wet spun microfiber composition having at least one polymer such that the composition includes a porous multi-layer polymeric microstructure, and further includes at least one encapsulated therapeutic agent, such that the therapeutic agent is located in an inner core of the microstructure and is controllably releasable from the composition, and such that the microfiber has a degree of crystallinity at least 10% greater than that of control polymer prior to wet spinning; instructions for use; and, a container.

In related embodiments of the kit a first encapsulated therapeutic agent is dexamethasone. In other embodiments the kit contains a second encapsulated therapeutic agent. For example, the second therapeutic agent is at least one selected from the group of a sugar; a carbohydrate; a nucleotide sequence; a protein selected from the group of a growth factor, an immunoglobulin, an enzyme, and an antibiotic; and a drug, for example, an anti-apoptotic; an immunosuppressant; a pro-apoptotic; an anti-coagulant; an anti-tumor; an anti-viral; an anti-bacterial; an anti-mycobacterial; an anti-fungal; an anti-proliferative; and an anti-inflammatory, for example, a steroid selected from the group of: a cortisone compound, for example a dexamethasone, and a sex-related hormone; and a non-steroidal anti-inflammatory agent (NSAID). For example, the nucleotide sequences comprise a vector.

According to other embodiments of the kit, the polymers are at least one of poly-1-lactic acid (PLLA), poly-lactic-co-glycolide (PLGA) and polyvinylpyrrolidone (PVP). In related embodiments of the kit the composition has a structure selected from the group of: a fiber, a suture, a sphere, an implant, and a scaffold.

An aspect of the invention provides a device for treating a tissue, the device comprising: at least one microstructure polymer including a composition, such that the polymer secures or binds the tissue and is selected from the group of: a suture, a strand, a fiber, a filament, and a thread; such that the polymer is a biocompatible ester compound and the composition contains at least one therapeutic agent that forms a complex with the polymer and is characterized by controllable release from the polymer.

In an embodiment of the device, the device and/or polymer has a diameter of about 20 micrometers (micron, μm) to about 80 μm, or about 30 μm to about 100 μm. The device and/or polymer in a related embodiment is characterized by withstanding a load at failure of about 50 millinewtons (nM) to about 120 mN, for example the load at failure is about 60 mN to about 100 mN. The device and/or polymer in a related embodiment is characterized by a strength of about 8 megapascals (MPa) to about 50 MPa, about 50 MPa to about 100 MPa, about 100 MPa to about 200 MPa, and about 200 MPa to about 300 MPa.

In an embodiment of the device, the polymer includes plurality of polymers. In various embodiments, the plurality of polymers includes about two, three, four, five, six, eight, ten, twelve, or even fourteen polymers. The plurality of polymers in various embodiments is interlinked or bound closely together, such that the plurality of polymers forms a structure selected from the group of: a screen, a fabric, a scaffold, a yarn, an implant, and a mesh. In a related embodiment, the plurality of polymers includes a bio-resorable polymer and a non-resorbable polymer such as a polytetrafluoroethylene or analog thereof. In a related embodiment, the plurality of polymers is treated with an agent to reduce immunoreaction in the tissue or body of a subject, or to reduce microbial growth on the device and the plurality of polymers.

In various embodiments, the plurality of polymers is mixed, wetspun and then interlocked/bound, thereby forming the device such that strength and elasticity of the plurality of polymers is greater than strength and elasticity of a single polymer. In an embodiment of the device, including the interlocked/bound plurality of polymers, has a diameter of at least: about 50 μm to about 100 μm, about 100 μm to about 250 μm, 250 μm to about 350 μm, about 350 μm to about 450 μm, about 450 μm to about 650 μm, or about 650 μm to about 950 μm. In a related embodiment, the device having the interlocked/bound plurality of polymers is characterized by having a load at failure greater than: about 100 mN to about 200 millinewtons, about 200 mN to about 300 mN, about 300 mN to about 400 mN, about 400 mN to about 500 mN, or about 500 mN to about 600 mN. The device in a related embodiment has an effective strength of about 8-150 megapascals (MPa).

The polymer of the device in various embodiments includes a poly-L-lactic acid, a poly-lactic-co-glycolide, or an analog or derivative thereof. In various embodiments, the polymer contains a ratio of different polymers, for example about 1:1 to about 1:3, about 1:3 to about 1:5, about 1:5 to about 1:10, about 1:10 to about 1:20, or about 1:20 to about 1:30 of two different polymers. In various embodiments, the polymer contains about 1:1:0.01 to 1:30:0.01 of three different polymers.

In a related embodiment, the polymer is obtained from a spin dope having the polymer dissolved in a solvent such as dicholormethane, and then wetspun into a non-solvent to obtain the device. For example, the spin dope includes about 5% (w/w), 10%, 15%, 20%, 25%, 30%, 40%, 50%, 60%, 70%, 80%, 90%, or 95% polymer. In various embodiments, the solvent is an organic solvent such as an alcohol or hydrocarbon.

In various embodiments of the device, the polymer is further characterized by at least one property selected from the group of: crystalline, amorphous, bio-resorbable, porous, elastic, and sterile. For example, porosity of the polymer enhances the controllable release of the therapeutic agent. In a related embodiment, each polymer is a pure polymer having a distinct set of characteristics and properties, for example the polymer is entirely a poly-L-lactic acid or a poly-lactic-co-glycolide, or the polymer is entirely hydrophilic or hydrophobic. Alternatively, the polymer is a composite/blend material of at least two different materials (e.g., polymer, metal, nanodot composition). In a related embodiment, the device having interlocked/bound polymers contains different types of pure polymers or composite polymers, i.e., at least two polymers have different characteristics and properties.

In a related embodiment, the device, polymer and/or composition further includes an additional agent that modulates strength or elasticity of the polymer, or that modulates release of the therapeutic agent from the device. For example, the additional agent is at least one selected from: a polymer, an elasticizer, an emollient, a hardener, a carbon (e.g., a diamond, a graphite), a hydrocarbon, a nano-based composition, a composite material comprising at least two different types of substances, and the like. A nano-based composition for example includes: a nano-metal, a nano-ceramic, a nano-polymer, and the like. For example, device is composed of a composite material is for example a glass and a polymer, or a plastic and a polymer.

In a related embodiment, the polymer includes a water-soluble polymer. The polymer in various embodiments includes a structure that is crystalline, amorphous, or a combination thereof. For example, the polymer is composed of a plurality of polymers that produce the structure that enhances or stabilizes the therapeutic agent, or alternatively enhances release of the therapeutic agent from the device. In a related embodiment, the polymer includes a polyvinylpyrrolidone.

The polymer and/or device in various embodiments has a unique variety of properties, such as transparency, chemical and biological inertness, very low toxicity as well as high media compatibility and cross-linkable flexibility.

The therapeutic agent in various embodiments includes at least one of the group selected from: a low molecular weight drug such as a glucosteroid or a steroid hormone, a protein, a peptide, a sugar, a carbohydrate, and a nucleotide sequence. For example, the nucleotide sequence includes a vector such as a viral vector or a bacterial vector.

In various embodiments, the therapeutic agent and/or the composition is at least one selected from the group of: an inorganic compound, a drug, a genetic material, a protein, a carbohydrate, a synthetic polymer, and a pharmaceutical composition. For example, the genetic material is at least one selected from: mRNA, siRNA, shRNA, microRNA, DNA, RNA, and protein. In a related embodiment, the protein includes at least one of the group selected from: a growth factor, an immunoglobulin, an enzyme, and an antibiotic.

In a related embodiment, the therapeutic agent includes at least one selected from the group of: a lysozyme, an insulin, dexamethasone, a noggin. The therapeutic agent in various embodiments of the device is at least one selected from the group consisting of: anti-tumor, antiviral, antibacterial, anti-inflammatory, anti-mycobacterial, anti-fungal, anti-proliferative, anti-apoptotic, bone morphogenic protein antagonist.

The polymer in various embodiments of the device contacts the tissue and releases the therapeutic agent and treats or remediates a defect or a condition of cells of the tissue, such that the tissue is selected from the group of: epithelial, endothelial, vascular, nerve, muscle, cartilage, and bone. The tissue for example is in an organ selected from at least one of: eye, heart, kidney, lung, liver, pancreas, stomach, colon, bladder, abdomen, leg, foot, head, throat, hand, and lymph.

An aspect of the invention provides a method of producing a device for securing or binding a tissue, the method including: mixing a plurality of polymers and at least one composition containing a therapeutic agent with a solvent to form a resulting polymer material; and wet-spinning the resulting polymer material, thereby producing the device for securing or binding the tissue.

In an embodiment of the method, the therapeutic agent is selected from the group of: a drug, a protein, a sugar, a carbohydrate, and a nucleotide sequence. For example, the method includes prior to mixing, engineering the nucleotide sequence to express the protein having an amino acid sequence, such that the protein remediates a condition or defect in the tissue.

The method in various embodiments involves the therapeutic agent being at least one of the group selected from: anti-coagulant, anti-tumor, anti-viral, anti-bacterial, anti-mycobacterial, anti-fungal, anti-proliferative, anti-inflammatory, anti-apoptotic, immunosuppressant, and pro-apoptotic. In a related embodiment, the method further includes contacting the tissue in a subject. In a related embodiment, the therapeutic agent is of a sufficient purity to administer to a human, and contacting the tissue involves administering the device by at least one route selected from the group of: surgically, intravenous, intramuscular, intraperitoneal, intradermal, intrapulmonary, intravaginal, rectal, oral, buccal, topical, ocular, intraocular, and subcutaneous. In various embodiments, contacting the device to the tissue involves surgically implanting the device.

The therapeutic agent in a related embodiment of the method is dexamethasone, and the method involves contacting the device to the tissue to reduce inflammation in the tissue or surrounding cells or tissue.

In various embodiments of the method, the solvent includes is at least one of: an alkane, an alcohol, or a hydrocarbon, for example a dichloromethane and a tetrahydrofuran. For example, prior to mixing the plurality of polymers and the therapeutic agent, the method further involves dissolving the plurality of polymers in an organic solvent such as dichloromethane. In various embodiments, the dissolving the plurality of polymers involves increasing the temperature.

Wet-spinning in various embodiments of the method includes the step of loading the polymer material into a syringe, and dispensing the polymer material into a coagulation bath comprising a non-solvent. In various embodiments, the non-solvent includes at least one selected from the group of: an ether, an alcohol, and a hydrocarbon. For example, the alcohol is selected from ethanol, isopropanol (2-propanol), butanol, or an analog or a derivative thereof; the ether is ethyl ether, petroleum ether, or an analog or a derivative thereof; and the hydrocarbon is at least one selected from the group of: a benzene, n-hexane, n-heptane a toluene, a xylene, and an analog or a derivative thereof.

In a related embodiment, the non-solvent in the method is non-carcinogenic. In various embodiments, the non-solvent is one selected from the group of: petroleum ether, silicon oil, 2-propanol, ethanol, n-heptane, n-hexane, ethanol, water, dirnethylsilanediol (dmsd), and an analog or a derivative thereof. In a related embodiment, the non-solvent in one selected from the group of: benzene, a toluene, a xylene, an acetonitrile, an acetone, an ethane, a heptane, a dimethyl sulfoxide, a dimethyl formamide, an acetate for example ethyl acetate, a pyridine, and an analog or a derivative thereof.

In various embodiments of the method, a difference between the solubility parameter of the solvent and the solubility parameter of the non-solvent affects the rate of solidification and the degree of crystallinity of the microstructure. In various embodiments of the method, dispensing the polymer material into the coagulation bath involves manuipulating/altering the difference between the solubility parameter of the solvent and the solubility parameter of the non-solvent to be about: less than about 12 units, less than 10 units, less than 9 units, less than 8 units, less than 7 units, less than 6 units, less than 5 units, less than 4 units, less than 3 units, less than 2 units and less than 1 unit. In various embodiments, the difference between the solubility parameter of the solvent and the non-solvent is less than about 2-4 units, less than about 4-6 units, less than about 6-8 units, or less than about 8-10 units.

The polymer in various embodiments of the method includes a hydrophilic polymer, a hydrophobic polymer, or a combination thereof, for example the polymer is a poly-L-lactic acid, a poly-lactic-co-glycolide, a polyvinylpyrrolidone, or an analog or derivative thereof.

In various embodiments of the method, mixing the plurality of polymers and the composition containing the therapeutic agent with the solvent involves encapsulating an amount (w/v) of the therapeutic agent in the polymers. For example, the amount of therapeutic agent is at least: about 0.05% to about 0.5%, about 0.5% to about 2%, about 2% to about 4%, about 4% to about 8%, about 8% to about 15%, or about 15% to about 30%. In various embodiments, the therapeutic agent is an amount effective to treat or remediate a condition or defect in the tissue or surrounding cells in a subject. For example, the cells comprise a cell type selected from the group consisting of: skin cells, epithelial cells, hematopoietic cells, stem cells, spleen cells, kidney cells, pancreas cells, liver cells, neuron cells, glial cells, endothelial cells, muscle cells, sperm cells, heart cells, lung cells, ocular cells, bone marrow cells, blood cells, leukocyte cells, lymphocyte cells.

The method in a related embodiment further includes manipulating or processing the device, such that processing comprises interlinking the device, thereby forming a structure selected from the group of: a screen, a fabric, a scaffold, a yarn, an implant, and a mesh.

In various embodiments of the method, wet-spinning the polymer material to form the device involves at least one technique selected from the group of: extruding, spinning, winding, intertwining, and layering. In a related embodiment, the method involves using a forming device that interlinks/binds a plurality of devices obtained from wetspinning the polymer material, for example the forming device includes a mandrel, a wheel, an extruder, a rotating body, a beveled body, a spoke, a loom, and a weaver. For example, the forming device is effective for weaving two separate, perpendicular groups of the device, such that the appearance has a symmetric horizontal and vertical appearance, or alternatively the method involves braiding (interlacing three or more separate, perpendicular groups of devices) or twisting.

The method in various embodiments further includes contacting and binding at least one tissue with the device, thereby releasing the therapeutic agent from the device to the tissue over a period extending for hours, days, weeks, and months.

An aspect of the invention provides a kit for treating a subject having a medical condition, the kit including: a device comprising at least one microstructure polymer including a composition, such that the polymer secures or binds the tissue and is selected from the group of: a suture, a strand, a fiber, a filament, and a thread; such that the polymer is a biocompatible ester compound and the composition contains at least one therapeutic agent that forms a complex with the polymer and is characterized by controllable release from the polymer; instructions for use; and, a container.

In an embodiment of the kit, the polymer includes a poly-L-lactic acid, a poly-lactic-co-glycolide, a polyvinylpyrrolidone, or an analog or a derivative thereof.

In various embodiments of the kit, the polymer is further characterized by at least one property selected from the group of: crystalline, amorphous, bio-resorbable, porous, elastic, and sterile.

The therapeutic agent in various embodiments of the kit includes at least one of the group selected from: a low molecular weight drug such as a glucosteroid or a steroid hormone, a protein, a peptide, a sugar, a carbohydrate, and a nucleotide sequence. For example, the protein includes at least one of the group selected from: a growth factor, an immunoglobulin, an enzyme, and an antibiotic. In various embodiments of the kit, the nucleotide sequences is a vector for example a viral vector or a bacterial vector.

In various embodiments of the kit, the therapeutic agent is dexamethasone. In various embodiments, the therapeutic agent comprises at least one of the group selected from: anti-coagulant, anti-tumor, anti-viral, anti-bacterial, anti-mycobacterial, anti-fungal, anti-proliferative, anti-inflammatory, anti-apoptotic, immunosuppressant, and pro-apoptotic.

In a related embodiment of the kit, the therapeutic agent comprises at least one selected from the group of: a lysozyme, an insulin, dexamethasone, a noggin.

In a related embodiment of then kit, the polymer includes a plurality of polymers that is interlinked or bound closely together, wherein the plurality of polymers forms a structure selected from the group of: a screen, a fabric, a scaffold, a yarn, an implant, and a mesh.

In a related embodiment of the kit, the instructions for use include instructions for securing or binding the device to the tissue.

An aspect of the invention provides a fiber composition including a polymer and a drug, such that the polymer and drug are coagulated and crystallized by solvent-induced crystallization (SINC) into a non-solvent to form the fiber composition.

The drug in various embodiments of the composition is dissolvable in the polymer, for example the drug is hydrophobic. For example, the drug is an anti-inflammatory. Alternatively, the drug in the composition includes a region that is hydrophilic, for example the region is an internal portion of the drug.

In a related embodiment, the drug includes a low molecular weight drug. The drug in a related embodiment is a macromolecule. For example, the macromolecule is at least one selected from the group of: a protein, a glycoprotein, a steroid, a peptide, and a nucleic acid. In a related embodiment, the steroid is a glucosteroid for example dexamethasone for reducing inflammation in cells or a tissue.

The polymer in various embodiments of the composition includes a carbonyl functionality. In a related embodiment, the polymer includes an ester functionality. For example, the polymer is a polyester polymer.

In various embodiments of the composition, the drug is encapsulated in a solid solution/complex with the polymer, such that the drug enhances strength, elasticity, and stability of the polymer. For example, the drug increases the strength, elasticity and/or stability about 5-10%. 10%-25%, 25%-50%, 50%-75%, 75%-100%, 100%-200%, 200%-300%, or 300%-400%. In a related embodiment, the drug increases the strength of the polymer about 8 MPa to about 50 MPa, about 50 MPa to about 100 MPa, about 100 MPa to about 200 MPa, or about 200 MPa to about 300 MPa.

The polymer in various embodiments of the composition includes a hydrophilic polymer or a hydrophobic polymer. For example, the polymer includes a poly-L-lactic acid, a poly-lactic-co-glycolide, a polyvinylpyrrolidone, an analog or a derivative thereof, or a combination or ration thereof. In various embodiments, the polymer contains a ratio of different polymers, for example about 1:1 to about 1:3, about 1:3 to about 1:5, about 1:5 to about 1:10, about 1:10 to about 1:20, or about 1:20 to about 1:30 of two different polymers. In various embodiments, the polymer contains about 1:1:0.01 to 1:30:0.01 of three different polymers.

In a related embodiment, a region of the composition is characterized by at least one property selected from the group of: crystalline, amorphous, bio-resorbable, porous, elastic, and sterile. For example, the relative position/location of one of the polymer and/or the drug, or relative percentage of the polymer and/or drug, corresponds to the region of the composition have the at least one property.

In a related embodiment, the polymer and the drug are dissolved in a solvent and interaction and/or are wetspun for the period of time in the non-solvent to enhance the SINC. In various embodiment, the period of time is at least one selected from the group of: one minute, two minutes, six minutes, 15 minutes, 30 minutes, one hour, two hours, four hours, six hours, twelve hours, 15 hours, 18 hours, 20 hours, and 24 hours. For example, the period of time is about: two minutes to six minutes, six minutes to fifteen minutes, fifteen minutes to thirty minutes, thirty minutes to one hour, one hour to two hours, two hours to four hours, four hours to eight hours, eight hours to twelve hours, twelve hours to 16 hours, 16 hours to 20 hours, or 20 hours to 24 hours In a related embodiment, a difference between a solubility parameter of the solvent and the solubility parameter of the non-solvent affects at least one of: SINC, rate of solidification, and a degree of crystallinity. For example, the difference between the solubility parameter of the solvent and the solubility parameter of the non-solvent is selected from one of the following: less than about 12 units, less than 10 units, less than 9 units, less than 8 units, less than 7 units, less than 6 units, less than 5 units, less than 4 units, less than 3 units, less than 2 units and less than 1 unit. In various embodiments, the difference is less than about 2-4 units, less than about 4-6 units, less than about 6-8 units, or less than about 8-10 units. In a related embodiment, the difference enhances porosity, striation, diameter, and physical appearance of the composition and/or polymer.

In a related embodiment, the polymer includes a plurality of polymers. For example, the plurality is at least about three, four, five, six, ten, twelve, or fifteen polymers.

An aspect of the invention provides a method of producing a composition involving/including: mixing a polymer and a drug with a solvent to form a resulting polymer\drug material; and wet-spinning the polymer/drug material by phase inversion using a non-solvent, such that the polymer/drug material undergoes solvent-induced crystallization (SINC), such that the SINC includes forming a solid solution with enhanced strength compared to the polymer alone, thereby producing the composition.

In a related embodiment, the polymer includes a plurality of polymers, and mixing includes the plurality of polymers and the solvent.

The drug in various embodiments of the method, the drug is selected from the group of: a macromolecule, a peptide for example an oligopeptide or a polypeptide, a low molecular weight drug, a protein, a sugar, a carbohydrate, and a nucleotide sequence or nucleic acid.

In various embodiments, the drug includes at least one of the group selected from: anti-coagulant, anti-tumor, anti-viral, anti-bacterial, anti-mycobacterial, anti-fungal, anti-proliferative, anti-inflammatory, anti-apoptotic, immunosuppressant, and pro-apoptotic. In various embodiments the drug includes a therapeutic agent for example a macromolecule, a peptide, a low molecular weight drug, a protein, a sugar, a carbohydrate, or a nucleotide sequence or nucleic acid that encodes a protein having an amino acid sequence.

In a related embodiment, the drug in the composition is hydrophobic. In various embodiments, the drug includes a region that is hydrophilic.

In a related embodiment, the solvent comprises at least one of dichloromethane and tetrahydrofuran. In a related embodiment, the solvent is an organic solvent such as an alcohol or a hydrocarbon.

In a related embodiment of the method, wet-spinning includes loading the polymer/drug material into a syringe, and dispensing the polymer/drug material into a coagulation bath including the non-solvent. In a related embodiment, the coagulation bath comprises petroleum ether, a hydrocarbon, or a heterocarbon.

In a related embodiment, the non-solvent in the method is non-carcinogenic or non-irritating to cells or to a tissue. In various embodiments, the non-solvent is one selected from the group of: petroleum ether, silicon oil, 2-propanol, ethanol, n-heptane, n-hexane, ethanol, water, dirnethylsilanediol, and an analog or a derivative thereof. In a related embodiment, the non-solvent in one selected from the group of: benzene, a toluene, a xylene, an acetonitrile, an acetone, an ethane, a heptane, a dimethyl sulfoxide, a dimethyl formamide, an acetate for example ethyl acetate, a pyridine, and an analog or a derivative thereof.

Wet-spinning in various embodiments of the method includes forming from the polymer/drug material at least one selected from the group of: a fiber, a filament, a thread, a suture, a screen, a fabric, a scaffold, a yarn, an implant, and a mesh.

In a related embodiment, mixing the polymer and the drug occurs during a period of time, for example the period of time is at least about: one minute, two minutes, six minutes, 15 minutes, 30 minutes, one hour, two hours, four hours, six hours, twelve hours, 15 hours, 18 hours, 20 hours, and 24 hours.

In a related embodiment of the method, wet-spinning the polymer/drug material involves/occurs during a period of time, for example the period of time is at least at least one selected from the group of about: one minute, two minutes, six minutes, 15 minutes, 30 minutes, one hour, two hours, four hours, six hours, twelve hours, 15 hours, 18 hours, 20 hours, and 24 hours. In a related embodiment, wet-spinning the polymer/drug material involves about: two minutes to six minutes, six minutes to fifteen minutes, fifteen minutes to thirty minutes, thirty minutes to one hour, one hour to two hours, two hours to four hours, four hours to eight hours, eight hours to twelve hours, twelve hours to 16 hours, 16 hours to 20 hours, or 20 hours to 24 hours. In a related embodiment of the method, wet-spinning the polymer/drug material further includes at least one selected technique selected from the group of: extruding, drawing, twisting, spinning, winding, intertwining, and layering.

In a related embodiment, mixing includes disintegrating, breaking up, or dispersing the drug, such that the drug dissolves in the polymer. For example, mixing involves using a solvent and in various embodiments the solvent includes at least one selected from the group of: petroleum ether, silicon oil, 2-propanol, ethanol, n-heptane, n-hexane, ethanol, water, dimethylsilanediol, and an analog or a derivative thereof.

BRIEF DESCRIPTIONS OF THE DRAWINGS

FIG. 1 panels A-D are scanning electron microscopy photomicrographs of surface and cross-sectional morphology of control and drug loaded PLLA microfibers fabricated by wet spinning Scale bars: panels A and C, 30 µm (×1000 magnification); panels B and D, 30 µm (×1300 magnification); and (insets) 5 µm (×5000 magnification).

FIG. 1 panel A columns I and II respectively are: scanning electron microscopy photomicrographs of surface morphology of control and drug loaded PLLA microfibers after fabrication.

FIG. 1 panel B columns I and II respectively are: scanning electron microscopy photomicrographs of cross-sectional morphology of control and drug loaded PLLA microfibers after fabrication.

FIG. 1 panel C columns I and II respectively are: scanning electron microscopy photomicrographs of surface morphology of control and drug loaded PLLA microfibers after eight weeks of incubation in phosphate buffered saline (PBS).

FIG. 1 panel D columns I and II respectively are: scanning electron microscopy photomicrographs of cross-sectional morphology of control and drug loaded PLLA microfibers after eight weeks of incubation in PBS.

Figure 2A:
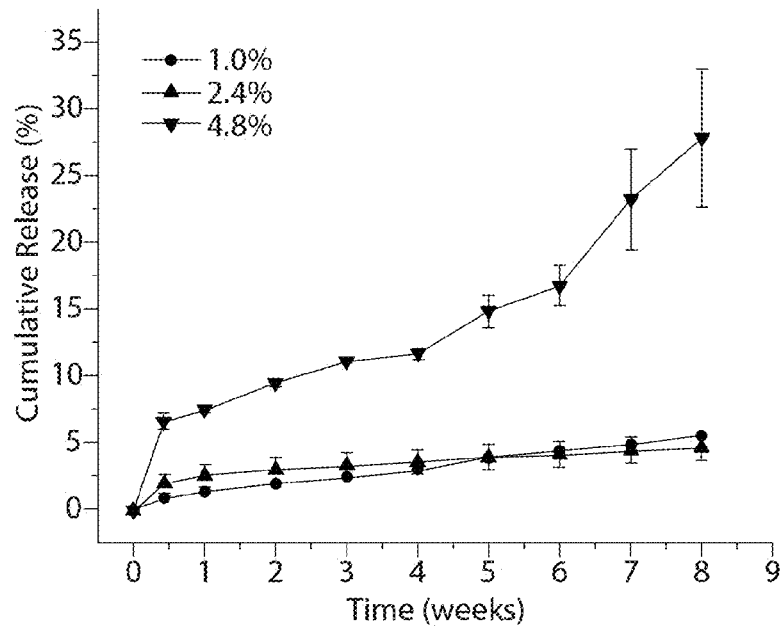
Figure 2B:
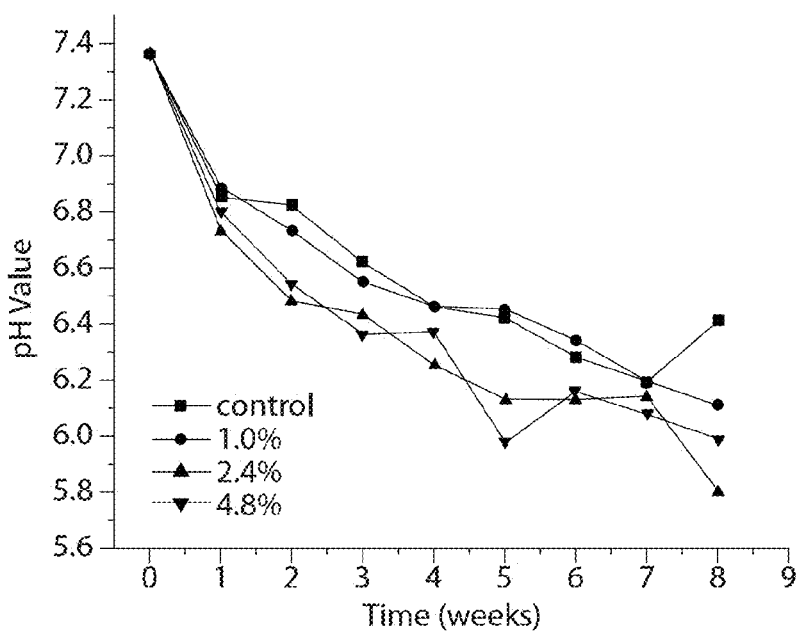

FIG. 2 panels A and B are line graphs of drug release as a function of time (eight weeks) of wet spun PLLA microfibers loaded with Dexamethasone (DXM).

FIG. 2 panel A is a graph of percent cumulative release (ordinate) of wet spun PLLA microfibers loaded with 1.0%, 2.4%, and 4.8% (w/w) DXM. Mean±SEM (Standard error of the mean) are presented.

FIG. 2 panel B is a graph of change in supernatant pH values as a function of degradation time of PLLA microfibers loaded with increasing amounts of DXM in comparison to control microfibers without drug.

Figure 3A:
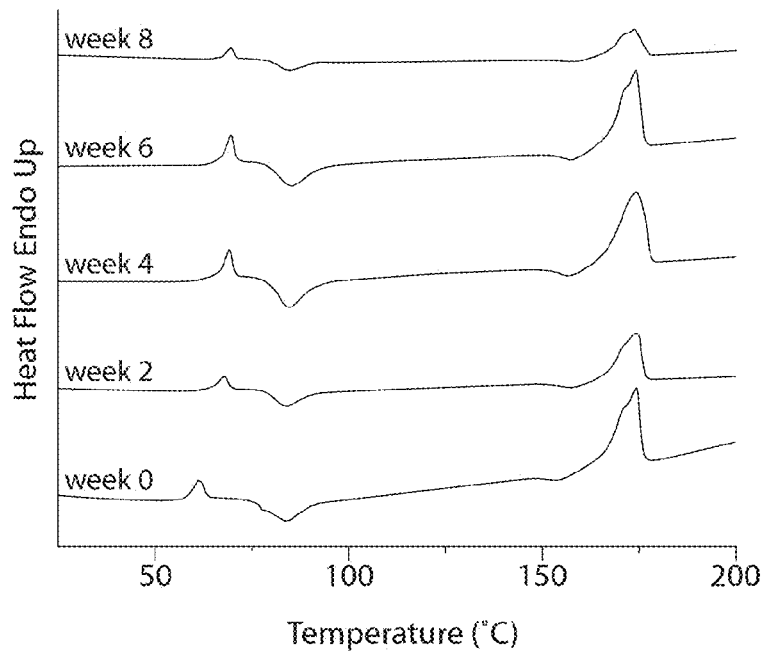
Figure 3B:
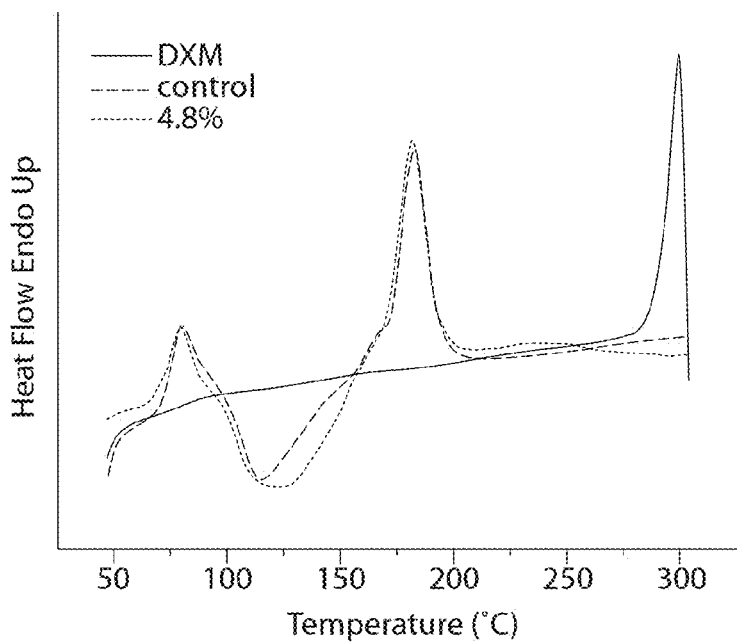

FIG. 3 panel A is a scan of representative differential scanning calorimetry (DSC) thermograms of wet spun in vitro 4.8% (w/w) DXM loaded PLLA microfibers at two week intervals.

FIG. 3 panel B compares Hyper DSC thermograms of control and 4.8% (w/w) DXM-loaded microfibers, and free DXM. No melting endotherm was present at 300° C. for drug-loaded microfibers.

Figure 4A:
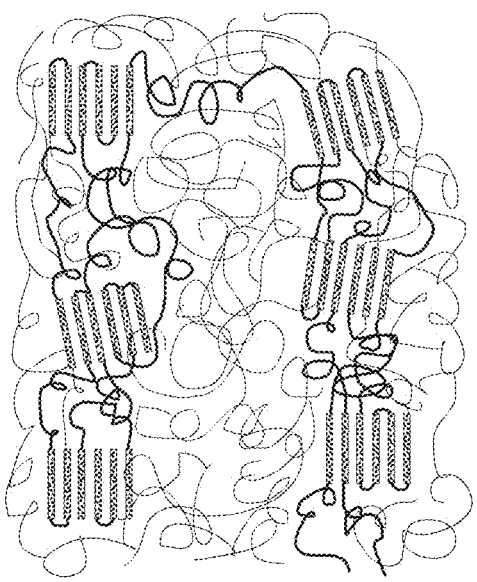
Figures 4B, 4C:
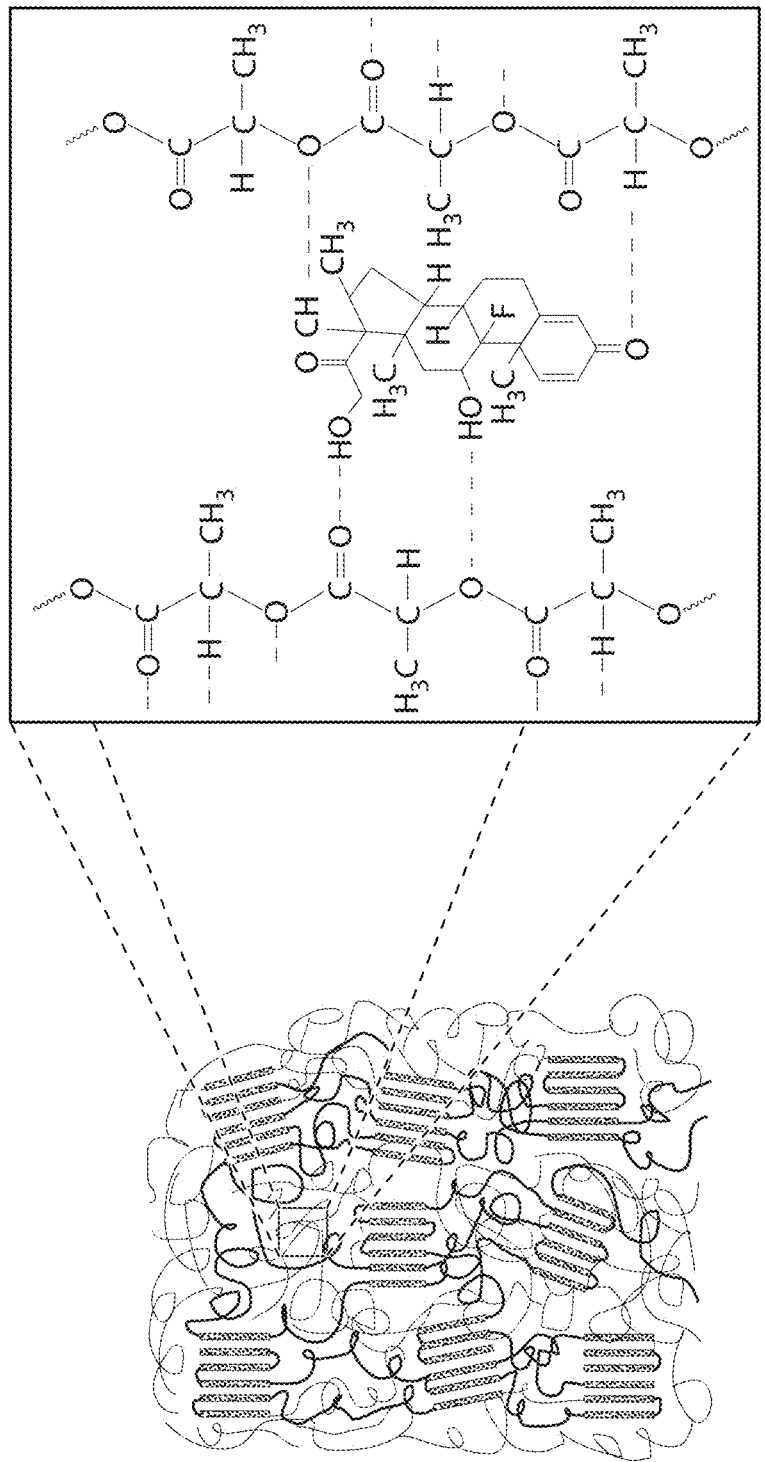

FIG. 4 panel A is a drawing of structure of a semi-crystalline wet spun polymer. The dark and ordered regions are crystalline and light tangled regions are amorphous.

FIG. 4 panel B is a drawing of formation of new crystalline areas during solvent-induced crystallization (SINC).

FIG. 4 panel C illustrates chemical structural secondary interactions between DXM and PLLA creating a reinforced composite material.

Figure 5:
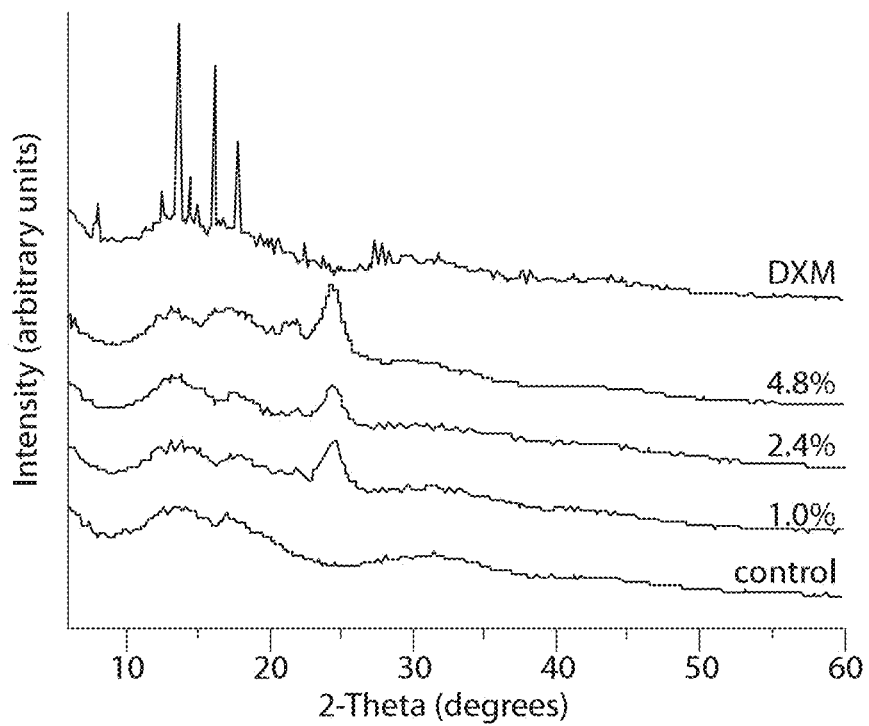

FIG. 5 is a graph of X-ray diffraction pattern traces of control (0%), DXM-loaded PLLA microfibers, and free DXM. No crystalline DXM was detected in any of the microfiber formulations. As the amount of DXM loaded was increased a new crystalline peak appeared in the diffraction pattern.

Figure 6A:
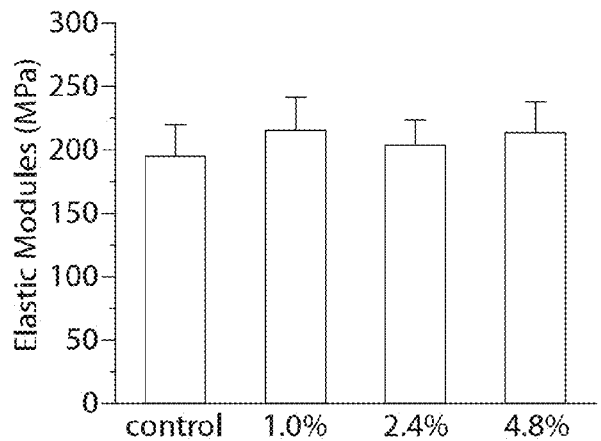
Figure 6B:
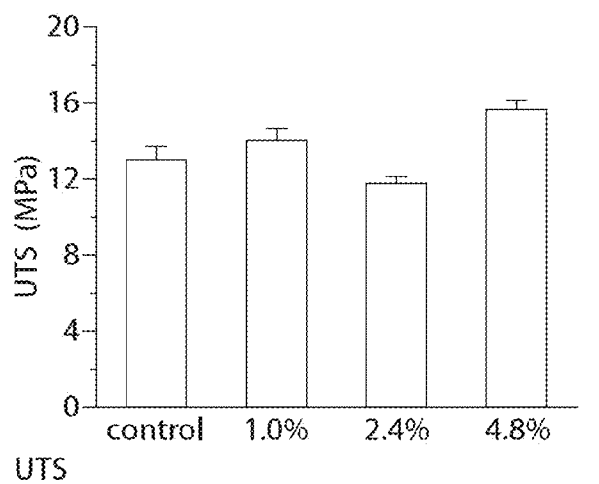
Figure 6C:
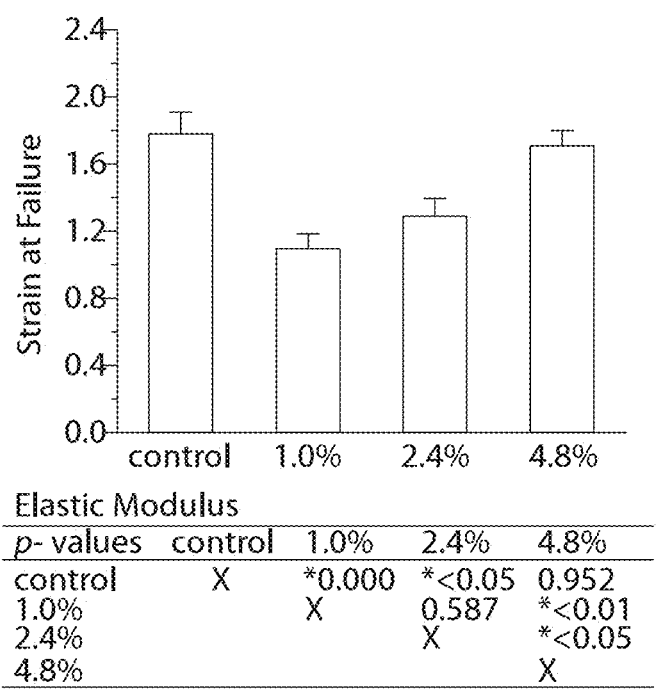
Figure 7A:
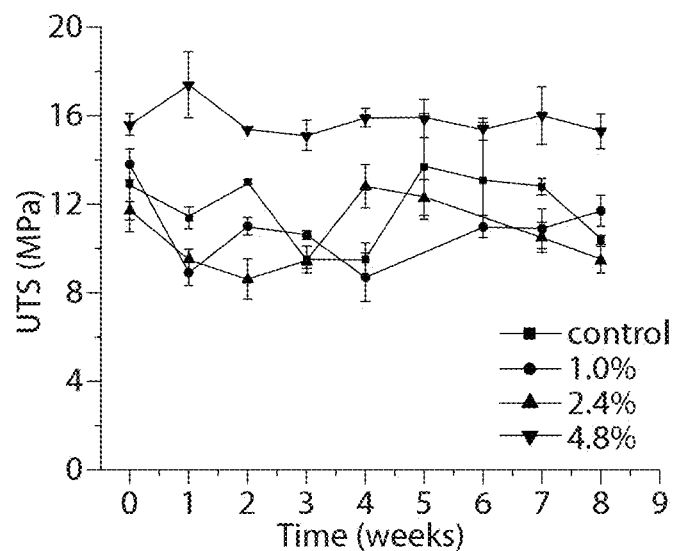
Figure 7B:
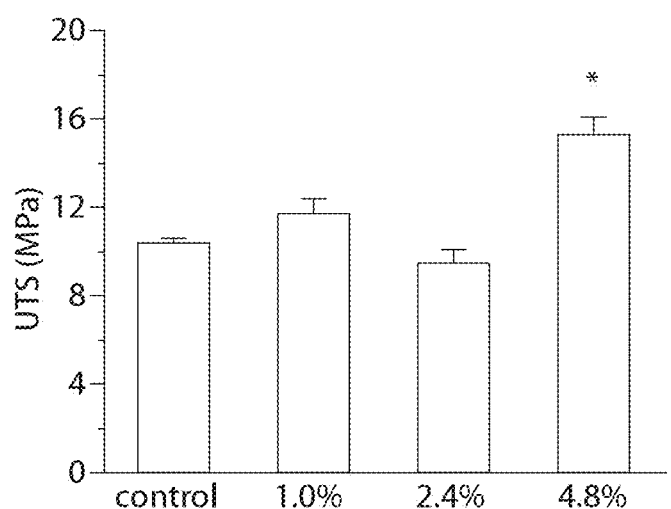
Figure 7C:
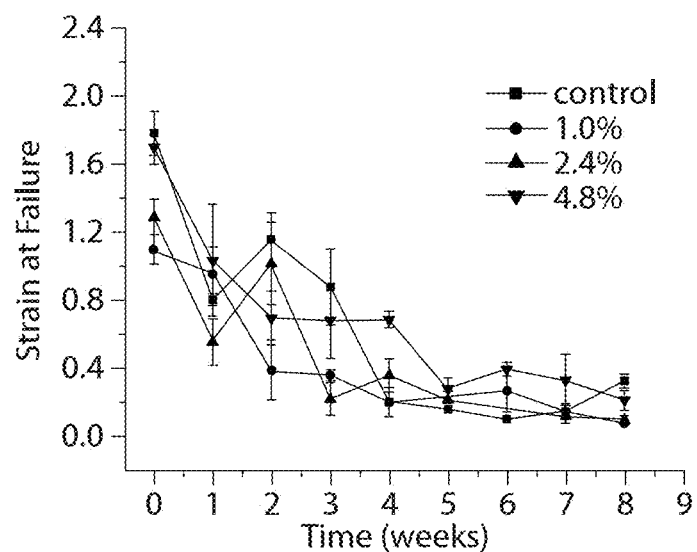
Figure 7D:
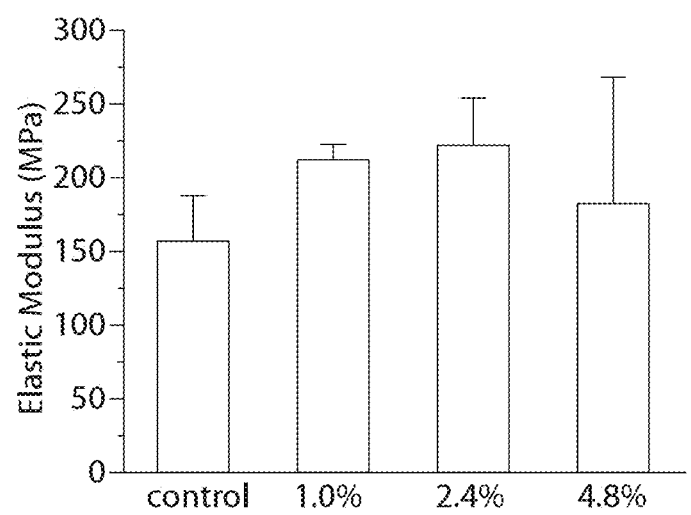

FIG. 6 panel A is a bar graph of elastic moduli of DXM-loaded PLLA microfibers loaded with 1.0%, 2.4% and 4.8% (w/w) DXM, and control. Values are presented as mean±SEM. *p<0.05 by one-way analysis of variance (ANOVA)

FIG. 6 panel B is a bar graph of ultimate tensile strength (UTS) of DXM-loaded PLLA microfibers loaded with 1.0%, 2.4% and 4.8% (w/w) DXM, and control. Values are presented as mean±SEM. *p<0.05 by ANOVA FIG. 6 panel C is a bar graph of strain at failure of DXM-loaded PLLA microfibers loaded with 1.0%, 2.4% and 4.8% (w/w) DXM, and control. Values are presented as mean±SEM. *p<0.05 by ANOVA FIG. 7 panel A is a graph of changes in UTS of DXM-loaded PLLA microfibers loaded with 1.0%, 2.4% and 4.8% (w/w) DXM as a function of time. Values are presented as mean±SEM. *p<0.05 by ANOVA FIG. 7 panel B is a graph of comparison of UTS of DXM-loaded PLLA microfibers and control microfibers at eight weeks of incubation in PBS. Values are presented as mean±SEM. *p<0.05 by ANOVA FIG. 7 panel C is graph of changes in strain at failure of DXM-loaded PLLA microfibers loaded with 1.0%, 2.4% and 4.8% (w/w) DXM as a function of time. Values are presented as mean±SEM. *p<0.05 by ANOVA FIG. 7 panel D is graph of comparison of elastic moduli of DXM-loaded PLLA microfibers and control microfibers at eight weeks of incubation in PBS. Values are presented as mean±SEM. *p<0.05 by ANOVA FIG. 8 panels A and B are polarized light photomicrographs of 4.8% (w/w) DXM-loaded PLLA microfibers. Scale bars (panels A and B) 50 µm; (insets) 10 µm.

Figure 8A:
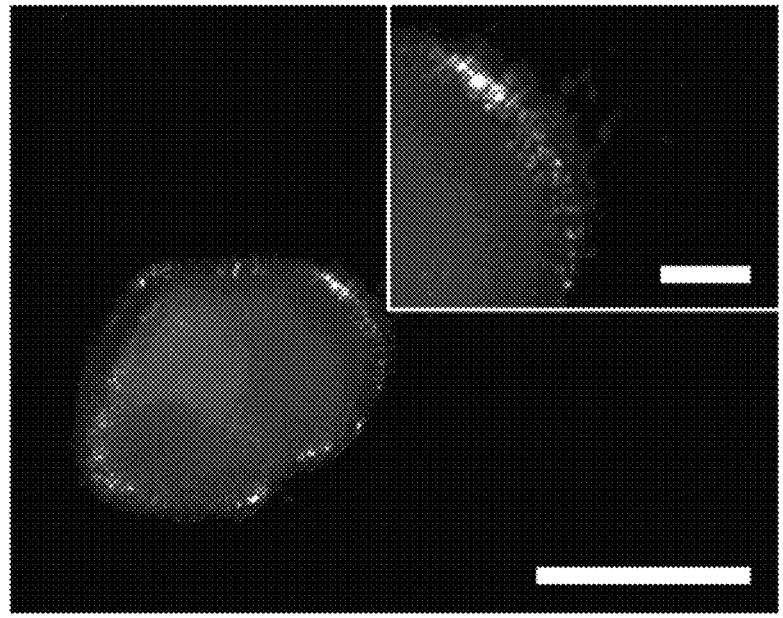
Figure 8B:
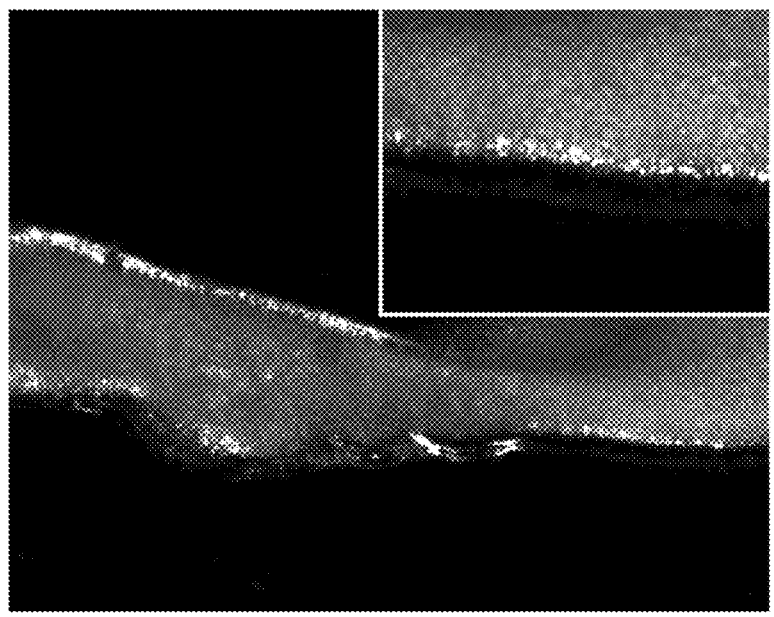

FIG. 8 panel A is an axial cross-section.

FIG. 8 panel B is an orthogonal cross-section.

Figure 9:
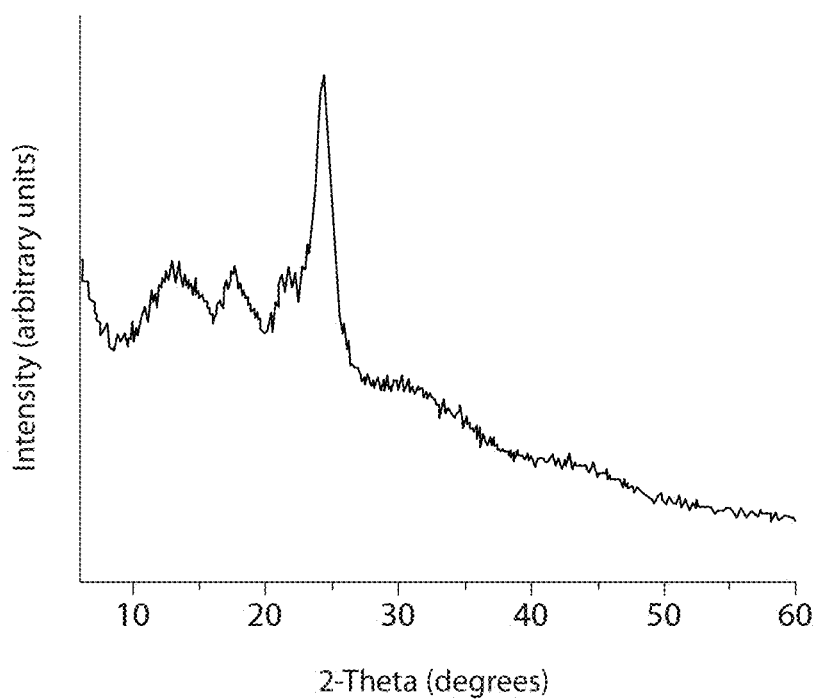
Figure 10A:
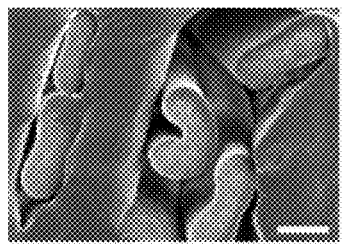
Figure 10B:
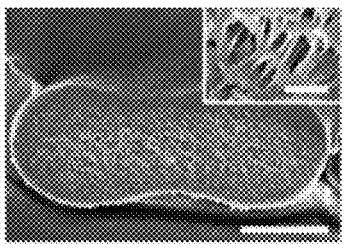
Figure 10C:
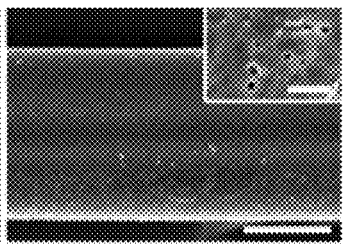
Figure 10D:
Figure 10E:
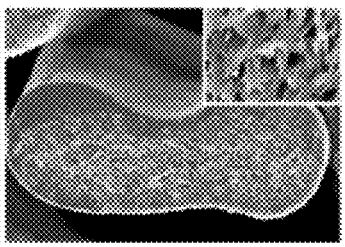
Figure 10F:
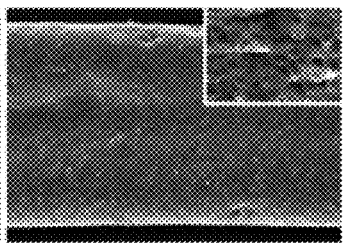
Figure 10G:
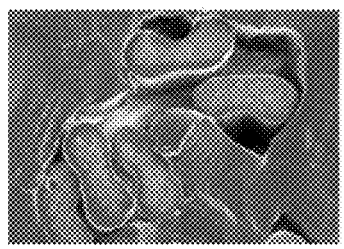
Figure 10H:
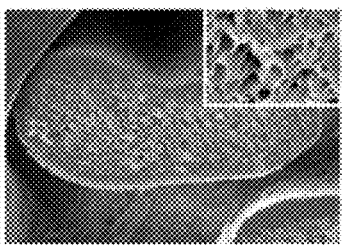
Figure 10I:
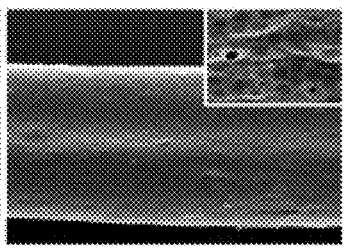
Figure 10J:
Figure 10K:
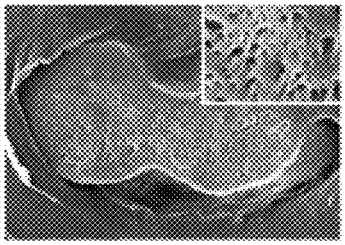
Figure 10L:
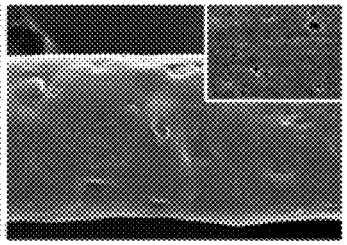
Figure 11A:
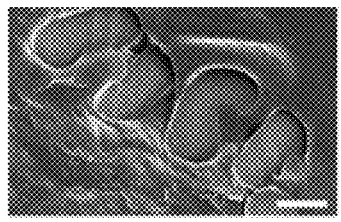
Figure 11B:
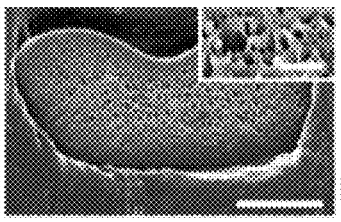
Figure 11C:
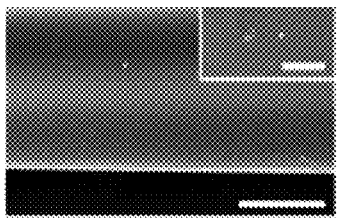
Figure 11D:
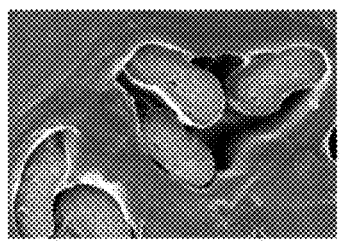
Figure 11E:
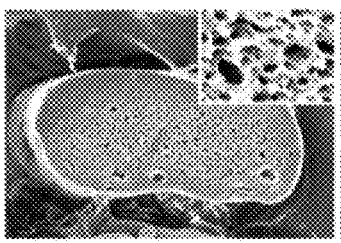
Figure 11F:
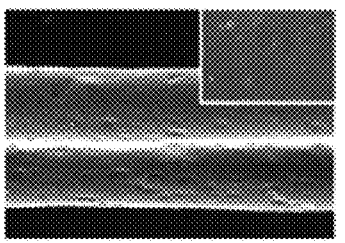
Figure 11G:
Figure 11H:
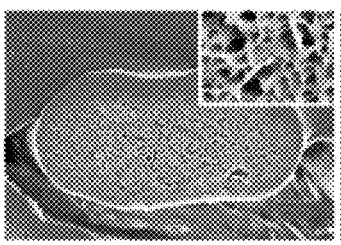
Figure 11I:
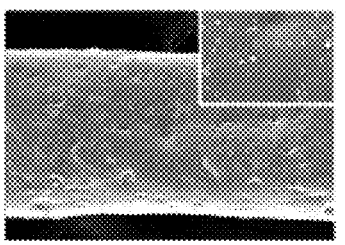
Figure 11J:
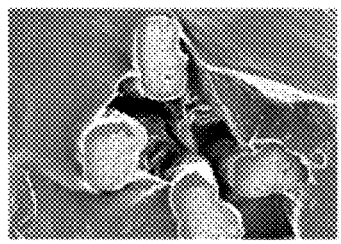
Figure 11K:
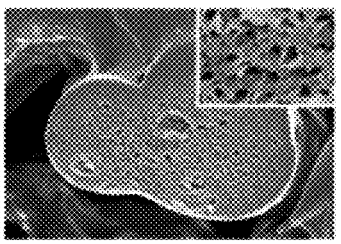
Figure 11L:
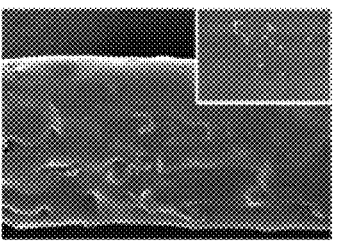

FIG. 9 is a trace of an X-ray diffraction pattern of control PLLA microfibers fabricated using a residence time of 1.5 hours.

FIG. 10 panels A-L are scanning electron micrographs of PLGA microfibers as a function of protein loading. Scale bar for panels A, D, G and J is as in panel A, 50 µm (350× magnification). Scale bar for panels B, E, H and K is as in panel B, 30 µam (1000× magnification). Scale bar for panels C, F, I and L is as in panel C, 50 µm (600× magnification). Insert scale bar for panels B, C, E, F, H, I, K and L is 3 µm (5000× magnification).

FIG. 10 panel A: a cross-sectional morphology of control PLGA microfibers.

FIG. 10 panel B: a cross-sectional morphology of an individual control PLGA microfiber.

FIG. 10 panel C: a surface morphology of an individual PLGA microfiber.

FIG. 10 panel D: a cross-sectional morphology of PLGA microfibers loaded with insulin (INS).

FIG. 10 panel E: a cross-sectional morphology of an individual PLGA microfiber loaded with INS.

FIG. 10 panel F: a surface morphology of an individual PLGA microfiber loaded with INS.

FIG. 10 panel G: a cross-sectional morphology of PLGA microfibers loaded with lysozyme (LZ).

FIG. 10 panel H: a cross-sectional morphology of an individual PLGA microfiber loaded with LZ.

FIG. 10 panel I: a surface morphology of an individual PLGA microfiber loaded with LZ.

FIG. 10 panel J: a cross-sectional morphology of PLGA microfibers loaded with bovine serum albumin (BSA).

FIG. 10 panel K: a cross-sectional morphology of an individual PLGA microfiber loaded with BSA.

FIG. 10 panel L: a surface morphology of an individual PLGA micro fiber loaded with BSA.

FIG. 11 panels A-L are scanning electron micrographs of PLLA microfibers loaded with proteins. Scale bar for panels A, D, G and J is as in panel A, 50 µm (350× magnification). Scale bar for panels B, E, H and K is as in panel B, 30 µm (1000× magnification). Scale bar for panels C, F, I and L is as in panel C, 50 µm (600× magnification). Inset scale bar for panels B, C, E, F, H, I, K and L is 3 µm (5000× magnification).

FIG. 11 panel A: a cross-sectional morphology of control PLLA microfibers.

FIG. 11 panel B: a cross-sectional morphology of an individual control PLLA microfiber.

FIG. 11 panel C: a surface morphology of an individual control PLLA microfiber.

FIG. 11 panel D: a cross-sectional morphology of PLLA microfibers loaded with INS.

FIG. 11 panel E: a cross-sectional morphology of an individual PLLA microfiber loaded with INS.

FIG. 11 panel F: a surface morphology of an individual PLLA microfiber loaded with INS.

FIG. 11 panel G: a cross-sectional morphology of PLLA microfibers loaded with LZ.

FIG. 11 panel H: a cross-sectional morphology of an individual PLLA microfiber loaded with LZ.

FIG. 11 panel I: a surface morphology of an individual PLLA microfiber loaded with LZ.

FIG. 11 panel J: a cross-sectional morphology of PLLA microfibers loaded with BSA.

FIG. 11 panel K: a cross-sectional morphology of an individual PLLA microfiber loaded with BSA.

FIG. 11 panel L: a surface morphology of an individual PLLA microfiber loaded with BSA.

Figure 12:
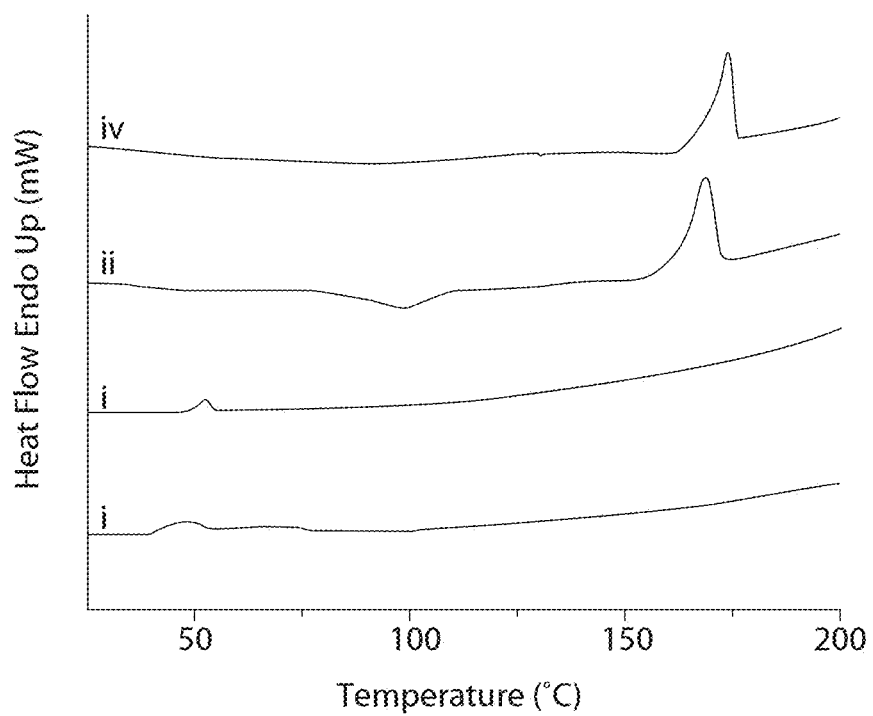

FIG. 12 is a graph of thermal analysis of wet spun microfibers. The curves are representative DSC thermograms of: (i) control PLGA microfibers after fabrication, (ii) control PLGA microfibers after fabrication and incubation in phosphate buffered saline (PBS) for 63 days, (iii) control PLLA microfibers after fabrication, and (iv) control PLLA microfibers after fabrication and incubation in PBS for 63 days.

Figure 13A:
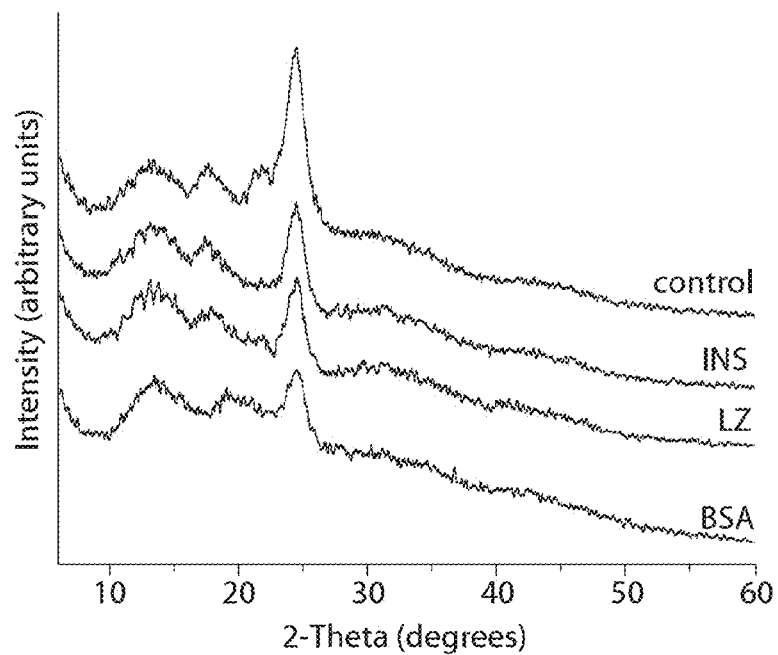
Figure 13B:
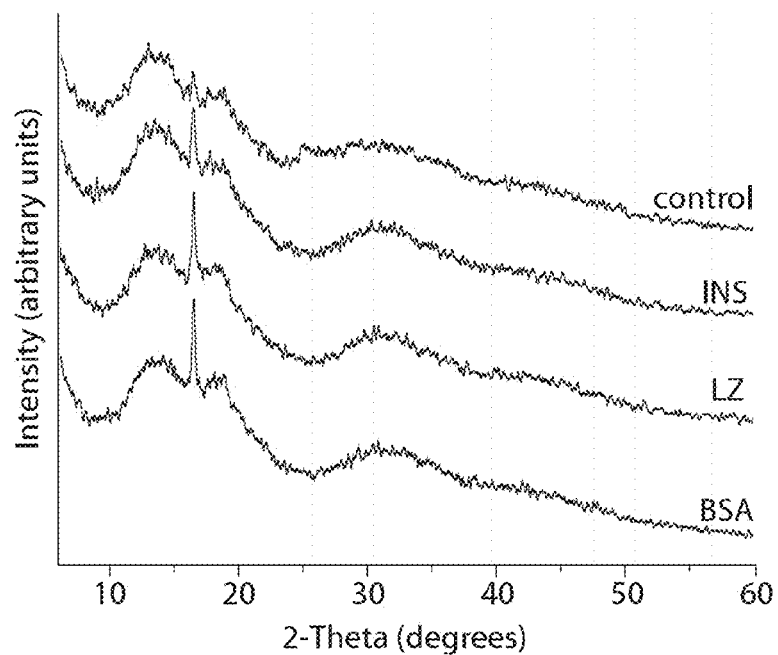
Figure 14A:
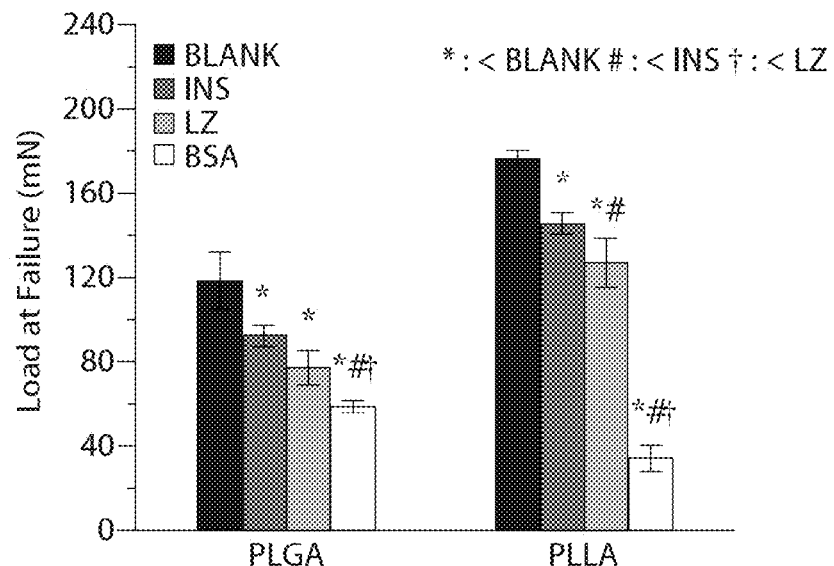
Figure 14B:
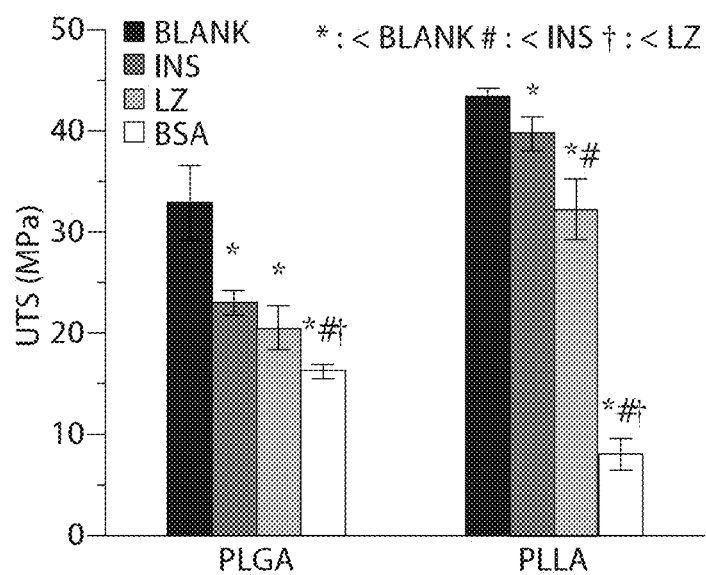
Figure 14C:
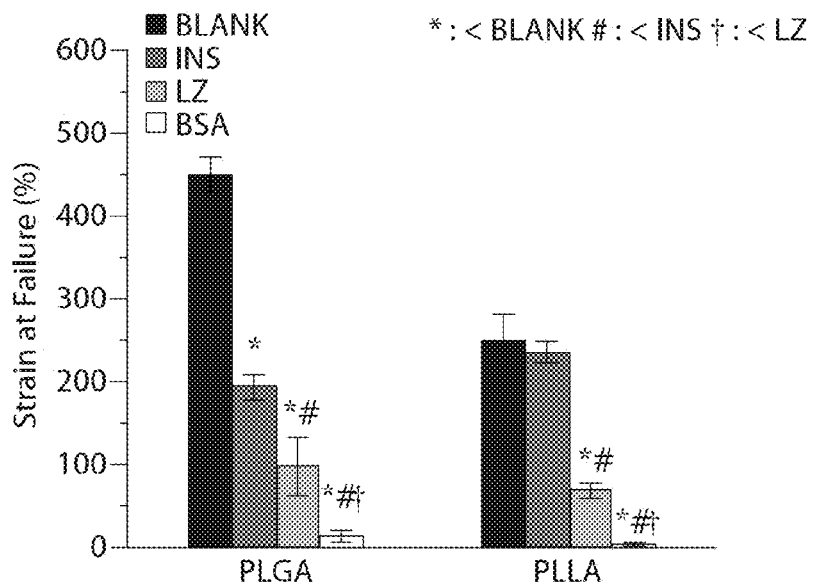
Figure 14D:
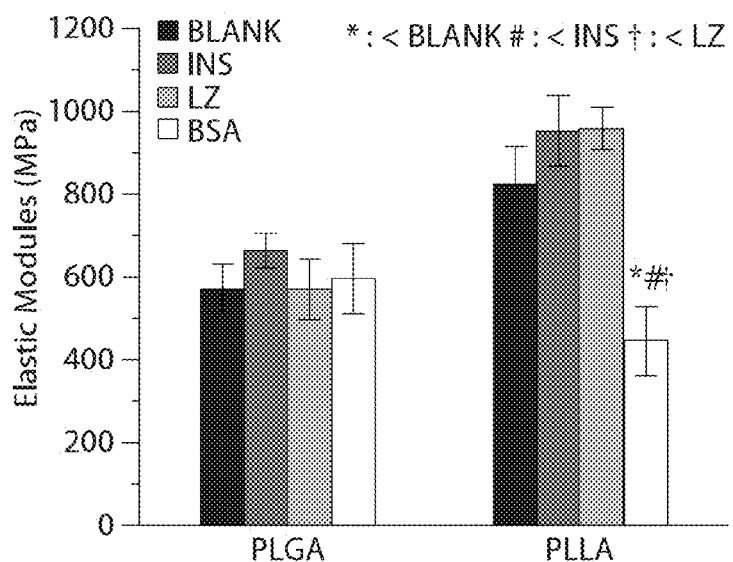
Figure 15A:
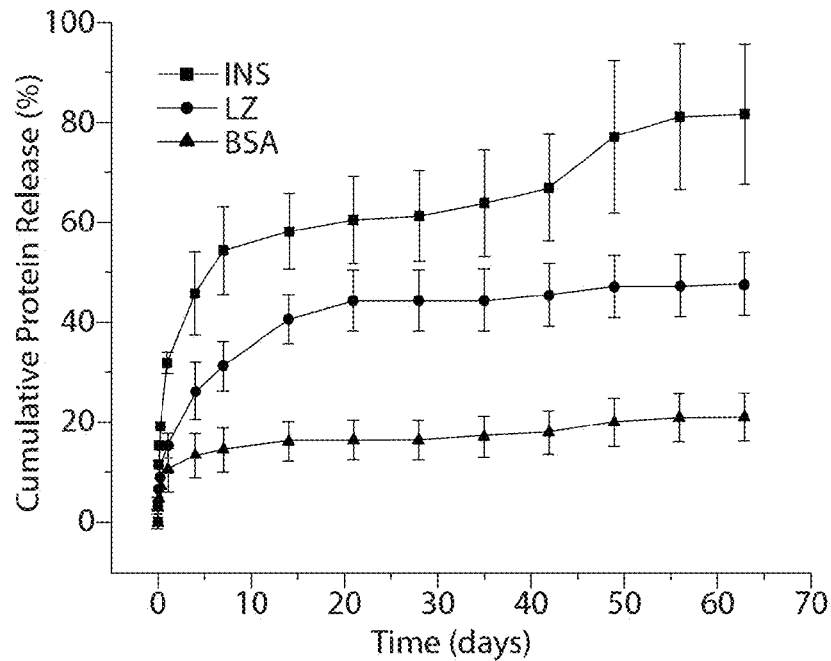
Figure 15B:
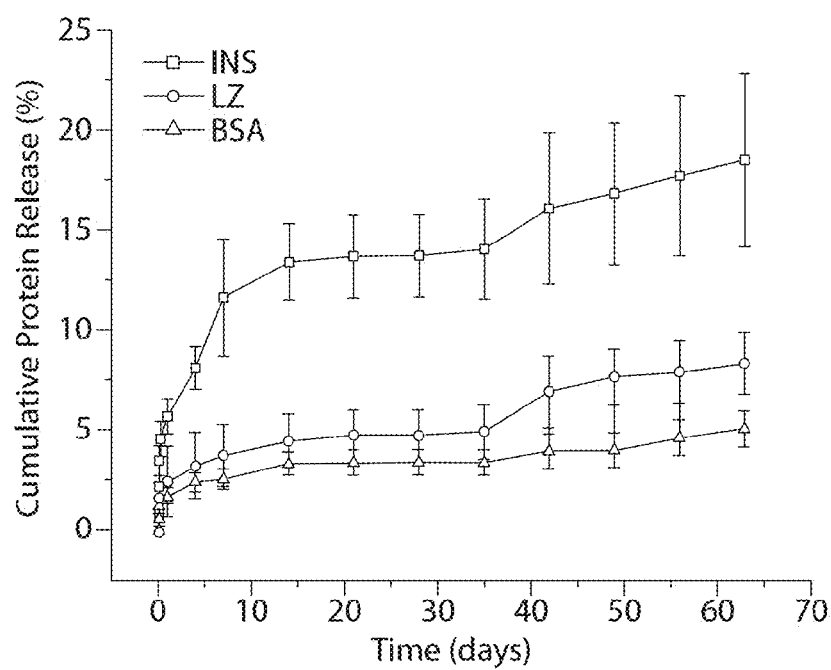
Figure 15C:
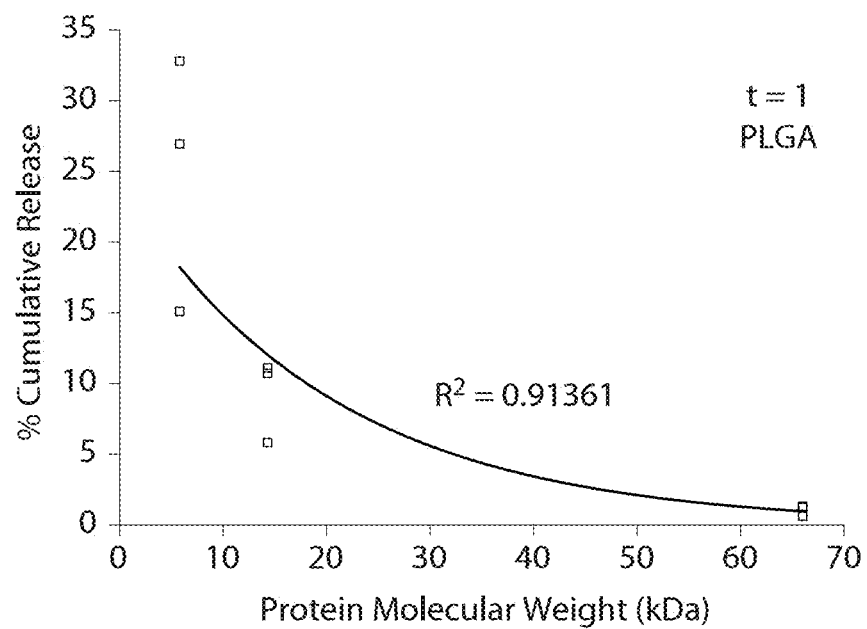
Figure 15D:
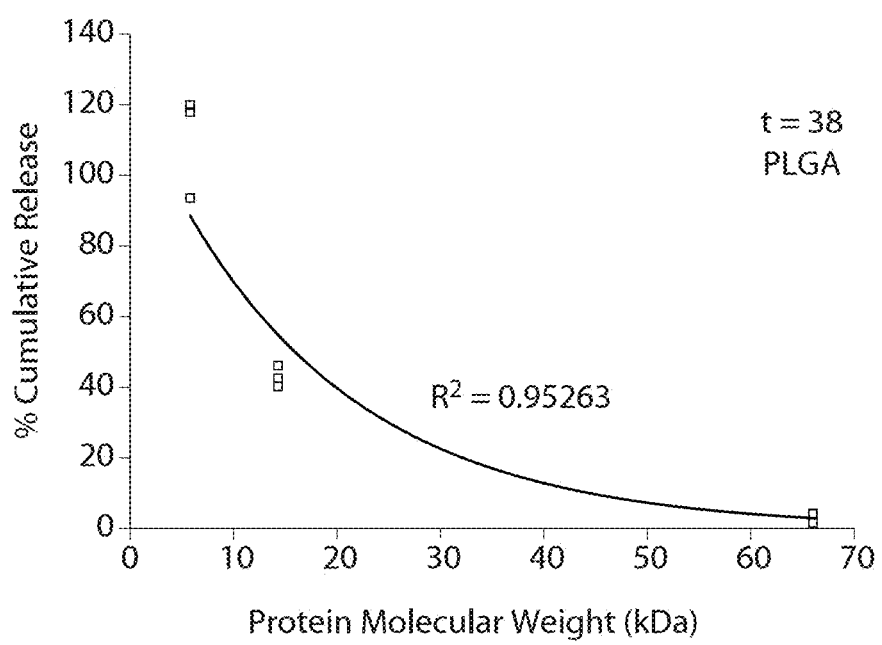
Figure 15E:
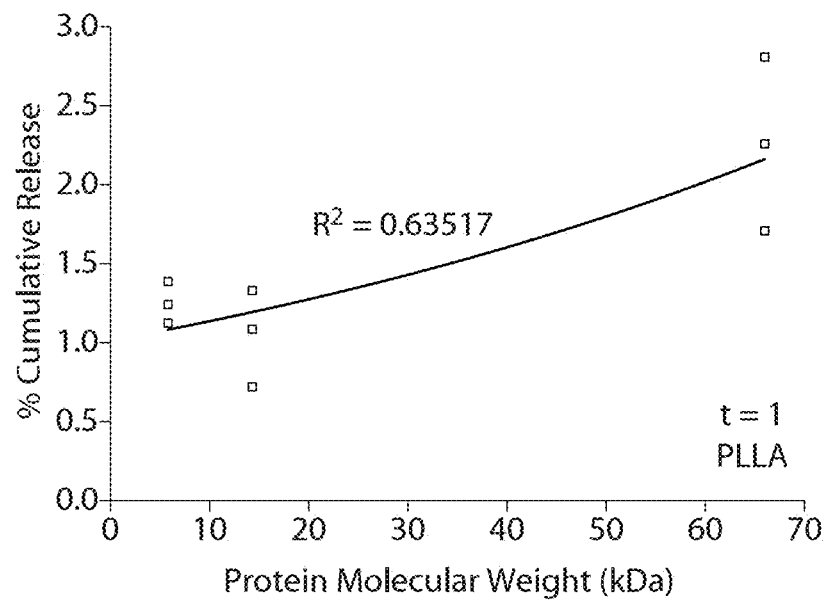
Figure 15F:
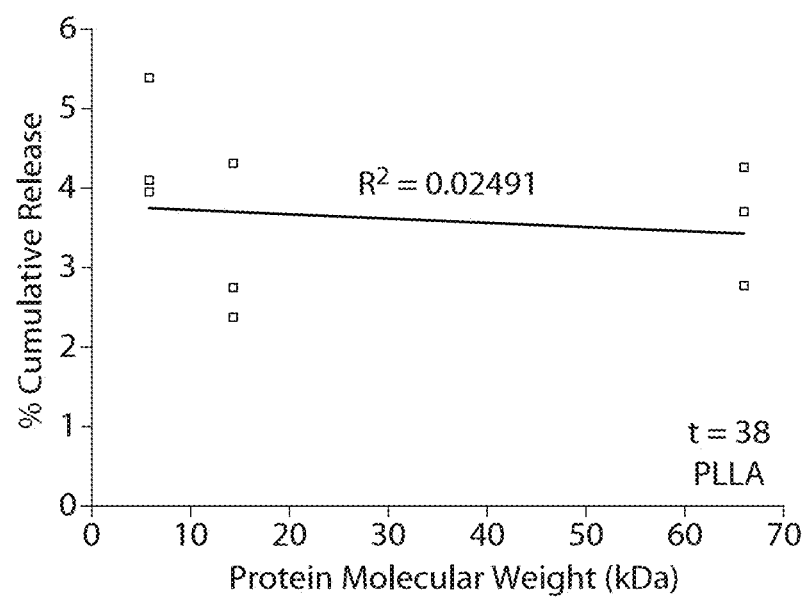

FIG. 13 panels A and B are: X-ray diffractograms of control (no protein), INS, LZ, and BSA-loaded PLLA microfibers.

FIG. 13 panel A: diffractograms obtained after fabrication, and FIG. 13 panel B: diffractograms obtained at 63 days incubation.

FIG. 14 panels A-D are bar graphs of mechanical analyses of wet spun PLGA and PLLA microfibers as a function of protein-loading and polymer type. Mean±S.D (standard deviation). are presented (n=5). Symbols *, #, †: significant in one-way ANOVA with Tukey post hoc multiple comparisons tests. Control (blank) and protein loaded PLGA and PLLA microfibers are represented by black (control/blank), dark (INS-loaded), light (LZ loaded), and white (BSA-loaded).

FIG. 14 panel A: load at failure measurements of PLGA and PLLA microfibers.

FIG. 14 panel B: ultimate tensile strength measurements of PLGA and PLLA microfibers.

FIG. 14 panel C: strain at failure measurements of PLGA and PLLA microfibers.

FIG. 14 panel D: elastic modulus measurements of PLGA and PLLA microfibers.

FIG. 15 panels A-F are line graphs of protein release profiles of cumulative percent release from loaded wet spun PLGA and PLLA microfibers. In panels A and B cumulative percent release is presented as mean±S.D. for duplicate batches of each formulation (n=6). In panels C-F, the correlation coefficient ($R^2$) is shown with the exponential regression, $y=Ar^x$ for each time point.

FIG. 15 panel A: cumulative percent release of proteins by PLGA microfibers loaded with INS (squares), LZ (circles) and BSA (triangles) as a function of time.

FIG. 15 panel B: cumulative percent release of proteins by PLLA microfibers loaded with INS (squares), LZ (circles) and BSA (triangles) as a function of time.

FIG. 15 panel C: cumulative percent release of proteins from PLGA fibers after fabrication at day one as a function of protein molecular weight.

FIG. 15 panel D: cumulative percent release of proteins from PLGA fibers after fabrication at day 38 as a function of protein molecular weight. Release kinetics from PGLA fibers was observed to exponentially decrease with increased protein molecular weight.

FIG. 15 panel E: cumulative percent release of proteins from PLLA fibers after fabrication at day one as a function of protein molecular weight.

FIG. 15 panel F: cumulative percent release of proteins from PLLA fibers after fabrication at day 38 as a function of protein molecular weight. PLLA fibers encapsulating proteins exhibited sustained release rates independent of molecular weight over the course of 38 days.

Figure 16A:
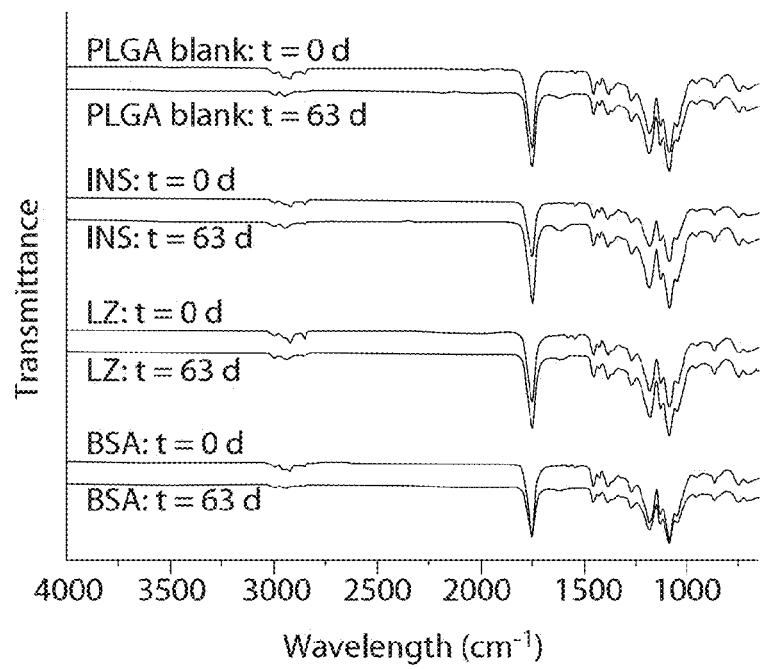
Figure 16B:
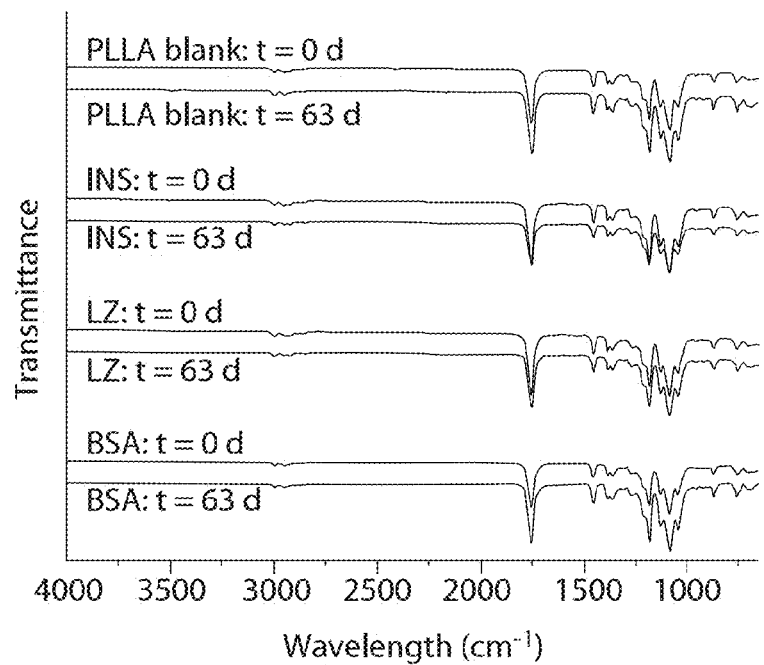

FIG. 16 panels A and B are FT-IR spectra of PLGA and PLLA formulations at fabrication (0 day) and at 63 day incubation. Each trace represents the average spectra of 16 scans per sample. FT-IR spectra were offset for clarity.

FIG. 16 panel A: FT-IR spectra of PLGA microfiber formulations of proteins INS, LZ and BSA or blank control (no protein) at fabrication and at 63 days.

FIG. 16 panel B: FT-IR spectra of PLLA microfiber formulations having no protein (blank) or proteins INS, LZ and BSA, or blank control (no protein) at fabrication and at 63 days.

Figure 17A:
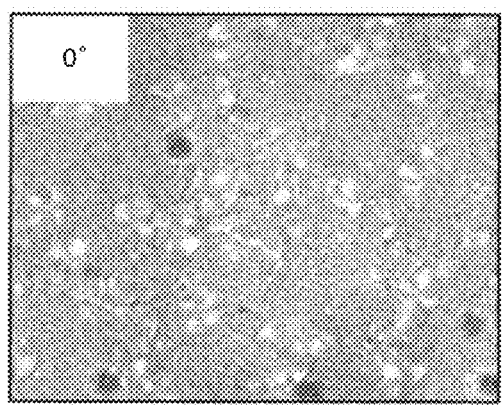
Figure 17B:
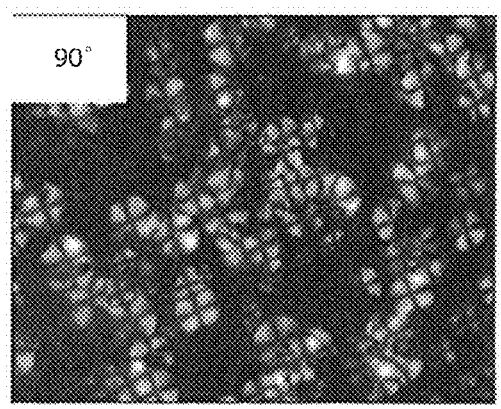

FIG. 17 panels A and B are cross-polarized optical micrographs of a PLLA:PLGA (1:1) phase separated film (magnification 20×) at 0° and 45° angles respectively.

Figure 18A:
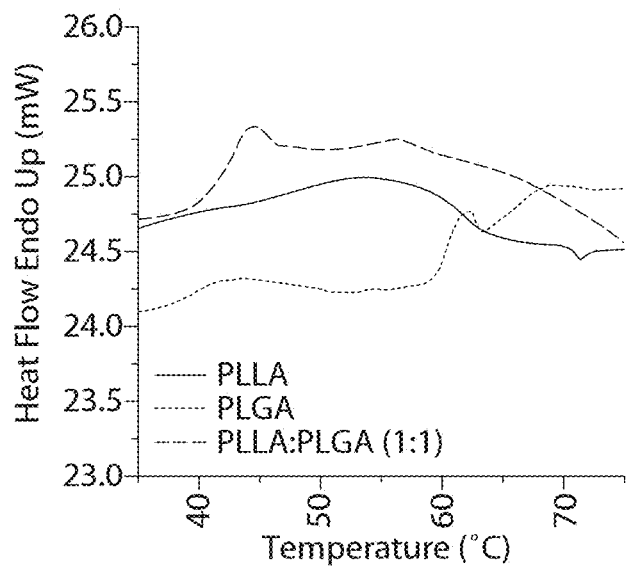
Figure 18B:
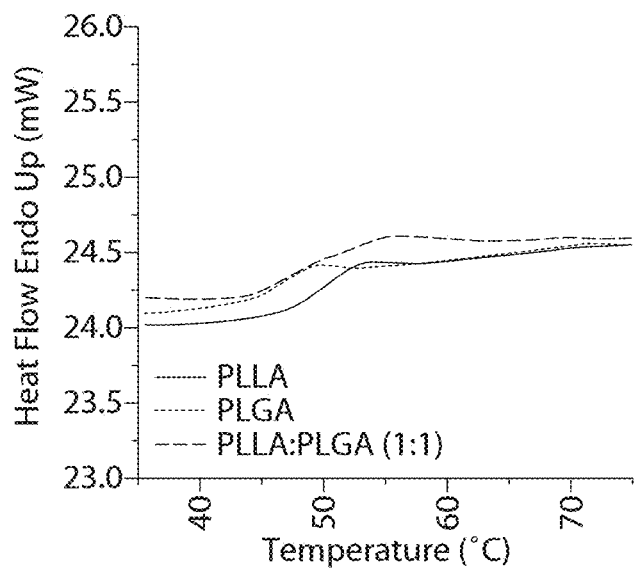
Figure 19A:
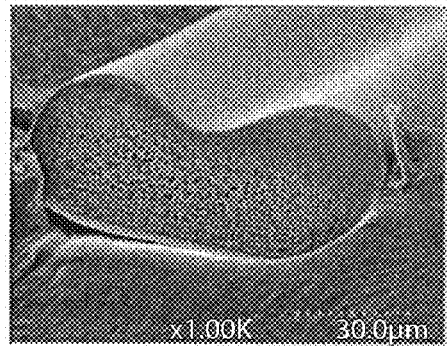
Figure 19B:
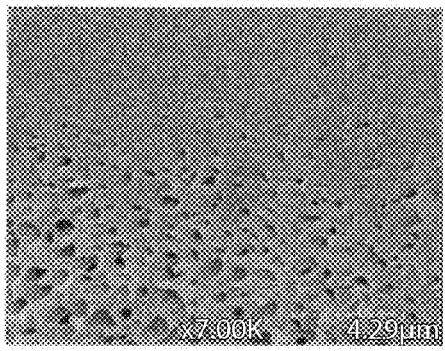
Figure 19C:
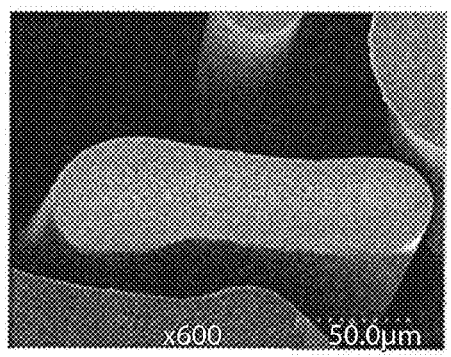
Figure 19D:
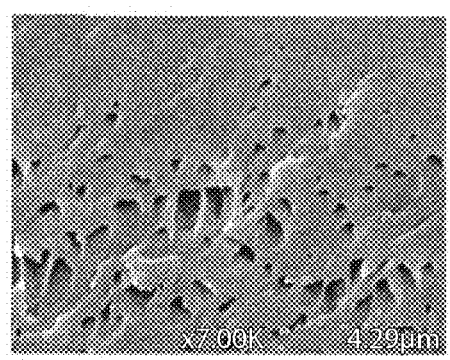
Figure 19E:
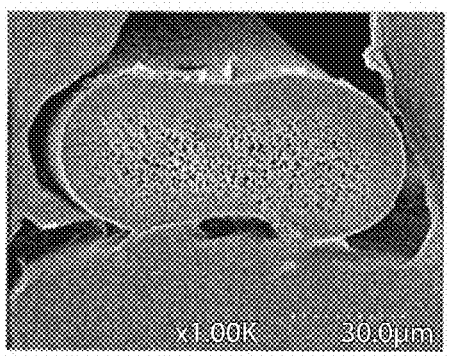
Figure 19F:
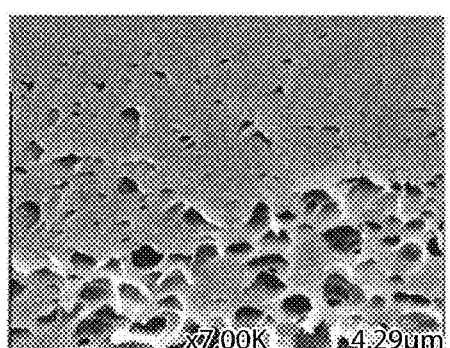

FIG. 18 panels A and B are graphs of DSC thermograms of PLLA, PLGA and PLLA:PLGA (1:1) microfibers. Two glass transitions were observed, each representative of PLLA and PLGA controls.

FIG. 18 panel A is a graph of DSC thermogram of PLLA:PLGA (1:1) microfibers obtained from first heating scan.

FIG. 18 panel B is a graph of DSC thermogram of PLLA:PLGA (1:1) microfibers obtained from second heating scan.

FIG. 19 panels A-F are scanning electron micrographs of cross-sectional morphology of binary phase PLLA:PLGA and control PLLA and PLGA microfibers.

FIG. 19 panels A and B are scanning electron micrographs of cross-sectional morphology of PLLA microfibers at low and high magnifications, respectively.

FIG. 19 panels C and D are scanning electron micrographs of cross-sectional morphology of PLGA microfibers at low and high magnifications, respectively.

FIG. 19 panels E and F are scanning electron micrographs of cross-sectional morphology of 1:1 PLLA:PLGA microfibers at low and high magnifications, respectively.

Figure 20A:
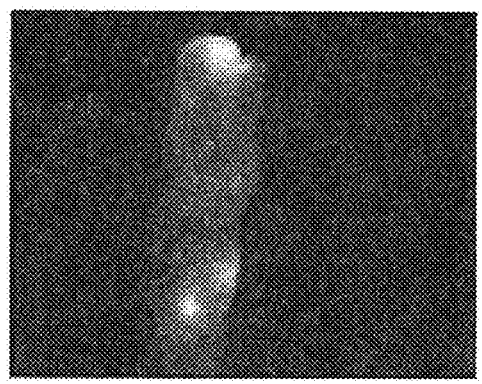
Figure 20B:
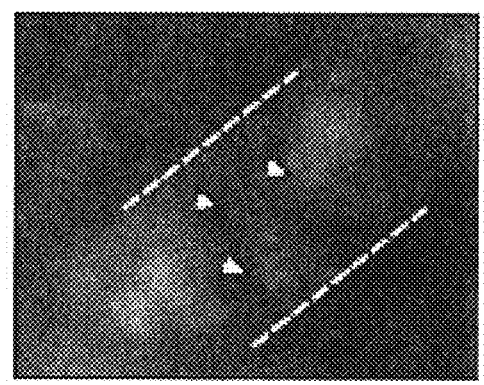

FIG. 20 panels A and B are fluorescent images of top and side views, respectively of 1:1 PLLA:PLGA binary phase composite microfibers encapsulating 0.3% w/w FITC (Fluorescein isothiocyanate)-dextran.

Figure 21A:
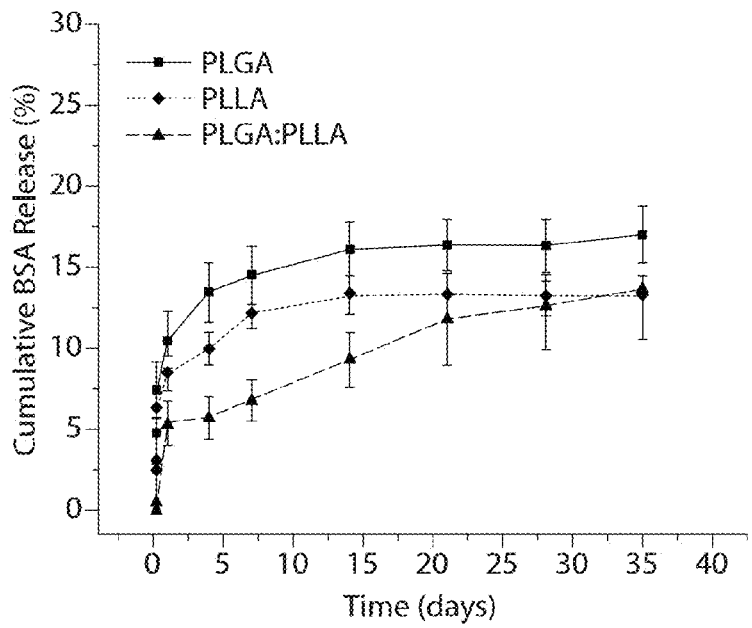
Figure 21B:
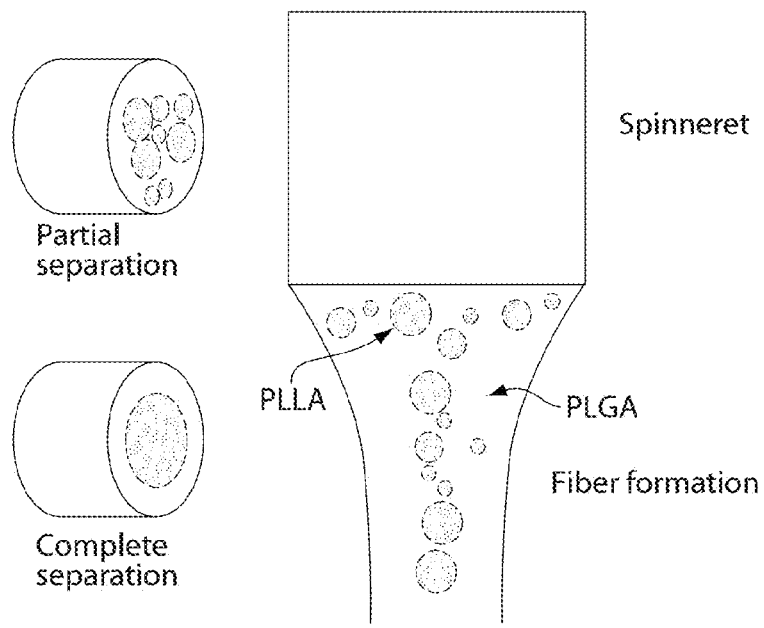

FIG. 21 panel A is a line graph of cumulative release kinetics of PLGA, PLLA and PLLA:PLGA (1:1) microfibers loaded with BSA. Fibers with PLLA:PLGA (1:1) exhibit reduced burst effect in comparison to PLGA and PLLA only fibers.

FIG. 21 panels B is a schematic diagram of phase separated spin dope solutions in the fabrication of binary phase composite microfibers.

Figure 22A:
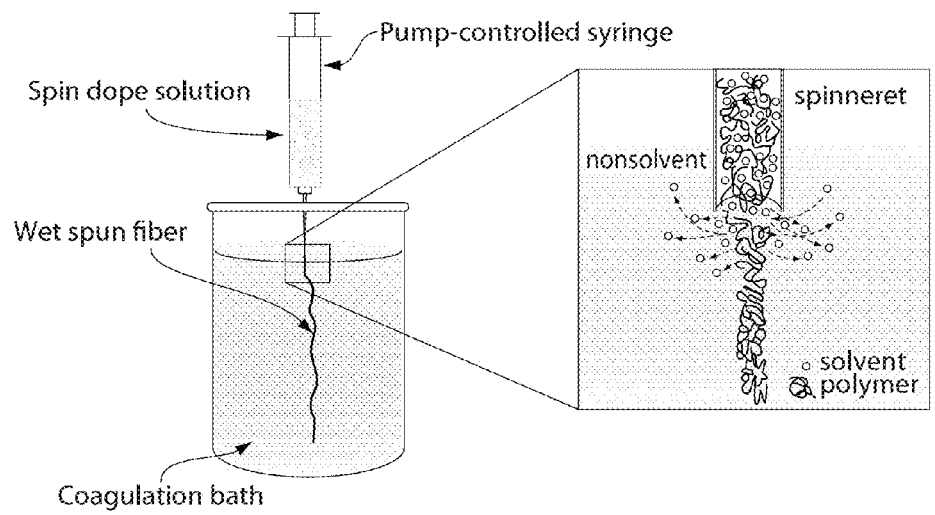
Figure 22B:
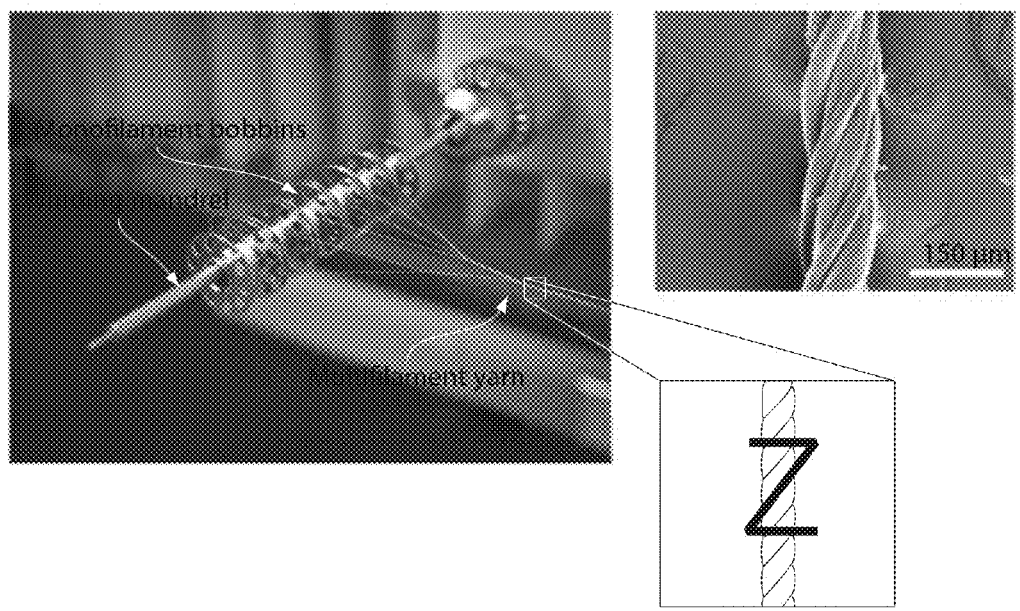
Figure 23A:
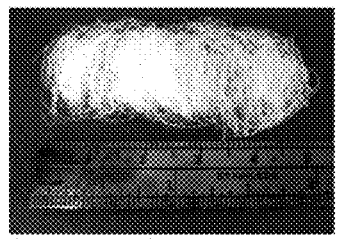
Figure 23B:
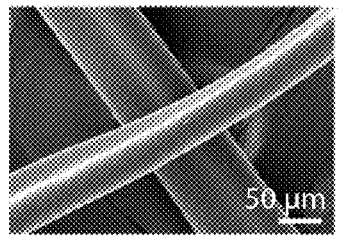
Figure 23C:
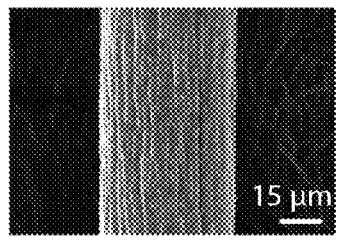
Figure 23D:
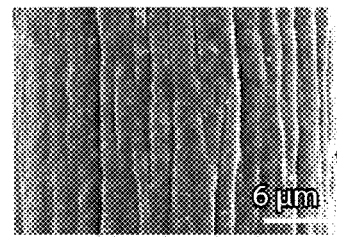
Figure 23E:
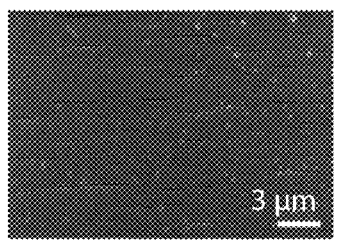
Figure 23F:
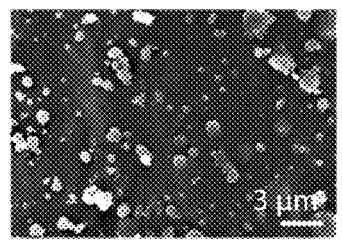
Figure 23G:
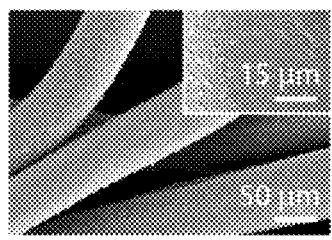
Figure 23H:
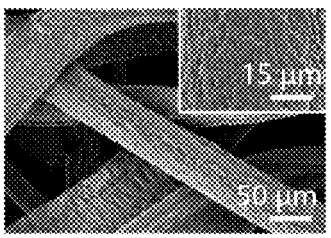
Figure 23I:
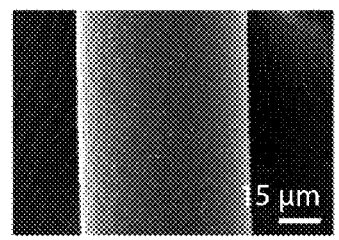
Figure 23J:
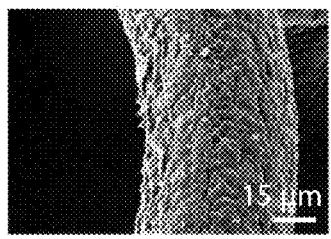
Figure 24A:
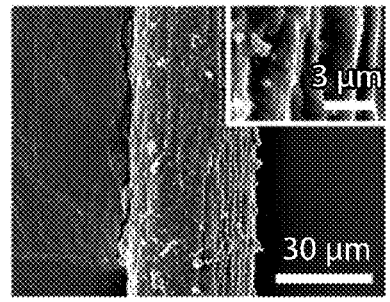
Figure 24B:
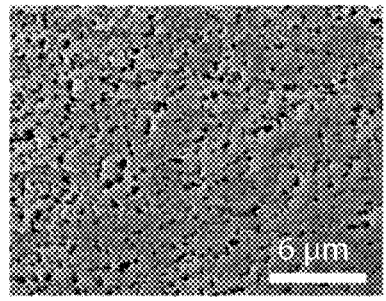
Figure 24C:
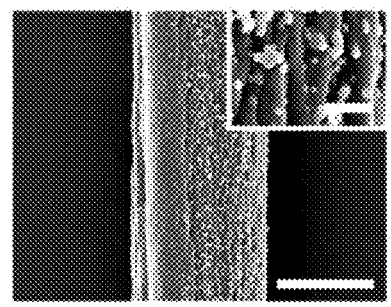
Figure 24D:
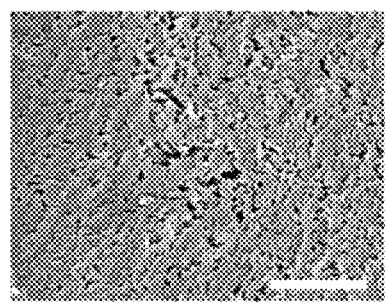
Figure 24E:
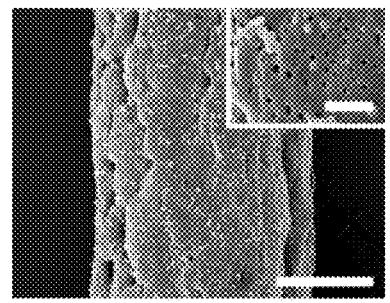
Figure 24F:
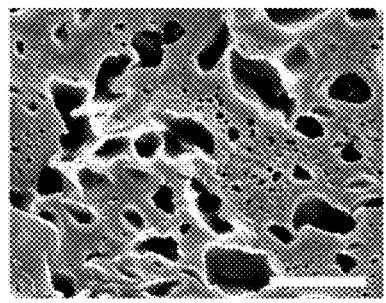
Figure 24G:
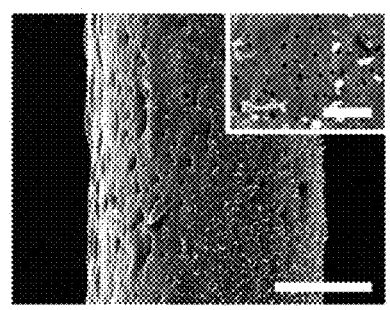
Figure 24H:
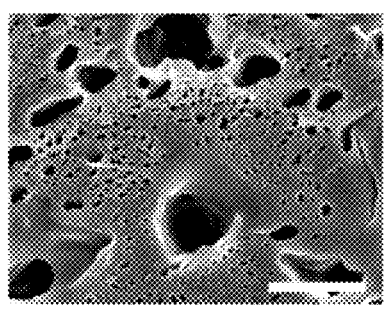

FIG. 22 panel A is a schematic representation of a spinning apparatus for wet spinning of polymer into fibers.

FIG. 22 panel B is a photograph of an apparatus for multifilament yarn production (left), a scanning electron micrograph of a multifilament yarn twisted along the longitudinal axis in 'Z' direction (right top), and a schematic representation of a multifilament yarn twisted along the longitudinal axis in 'Z' direction.

FIG. 23 panels A-J are a photograph and scanning electron micrographs of wet spun monofilaments with diverse surface structures.

FIG. 23 panel A is a photographic image of as-spun 3D fiber bundle of 20% (w/v) PLGA extruded into petroleum ether.

FIG. 23 panel B is a scanning electron micrograph of fibers in panel A.

FIG. 23 panel C is a scanning electron micrograph of a post-drawn 7.5% (w/w) $PLLA_{0.94}$ fiber extruded into a 75:25 ratio of 2-propanol to petroleum ether.

FIG. 23 panel D is a scanning electron micrograph of the fiber in panel C at higher magnification.

FIG. 23 panel E is a scanning electron micrograph of 15% (w/v) PLLA fibers extruded into a petroleum ether coagulation bath.

FIG. 23 panel F is a scanning electron micrograph of 10% (w/v) PLLA fibers extruded into a petroleum ether coagulation bath.

FIG. 23 panel G is a scanning electron micrograph of 7.5% (w/v) PLLA fibers extruded into a 50:50 ratio of petroleum ether to 2-propanol coagulation bath.

FIG. 23 panel H is a scanning electron micrograph of wet spun 7.5% (w/v) $PLLA_{0.94}$ fibers extruded into a 50:50 ratio of petroleum ether to 2-propanol coagulation bath.

FIG. 23 panel I is a scanning electron micrograph of PLLA/PLGA composite fiber extruded into a petroleum ether coagulation bath.

FIG. 23 panel J is a scanning electron micrograph of PLLA/PLGA composite fiber extruded into a 50:50 ratio of petroleum ether to 2-propanol coagulation bath.

FIG. 24 panels A-H are scanning electron micrographs of post-drawn composite fibers.

FIG. 24 panels A and C are scanning electron micrographs of surface structures of blank and DXM-loaded post-drawn composite fibers, respectively, spun from 10% (w/v) spin dope solution. These fibers were observed to have longitudinal striations with many spherulites.

FIG. 24 panels E and G are scanning electron micrographs of surface structures of blank and DXM-loaded post-drawn composite fibers, respectively, spun from 20% (w/v) spin dope solution. These fibers were observed to have nanoporous surfaces, and fewer spherulites compared to composite fibers in panels A and C.

FIG. 24 panels B and D are scanning electron micrographs of cross-sectional morphology of blank and DXM-loaded post-drawn composite fibers, respectively, spun from 10% (w/v) spin dope solution.

FIG. 24 panels F and H are scanning electron micrographs of cross-sectional morphology of blank and DXM-loaded post-drawn composite fibers, respectively, spun from 20% (w/v) spin dope solution. These fibers were observed to have greater porosity compared to fibers shown in B and D.

Figure 25A:
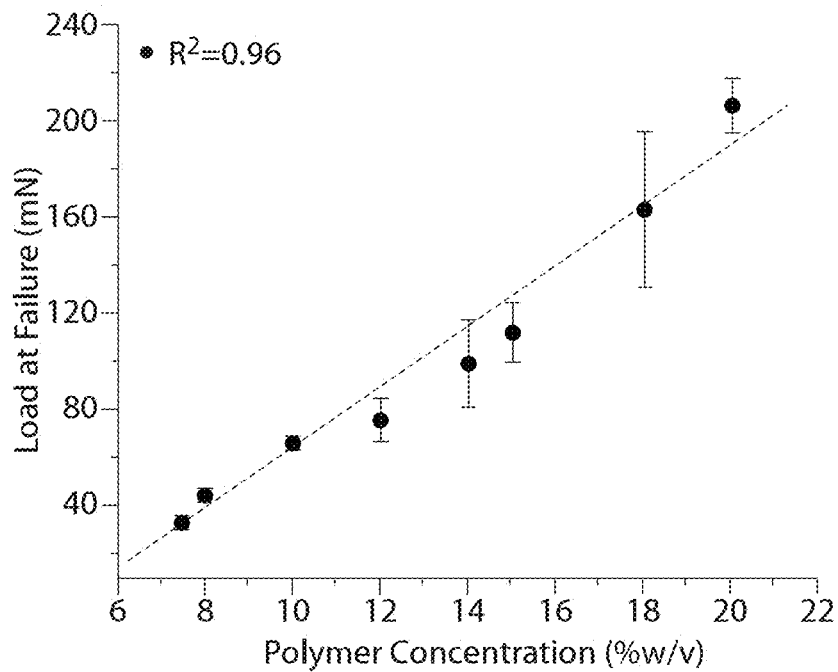
Figure 25B:
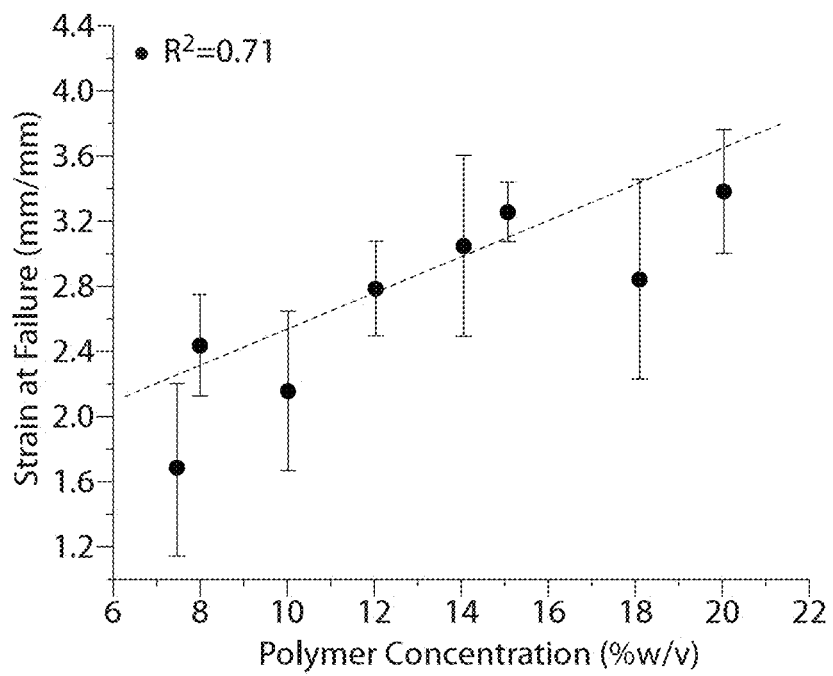

FIG. 25 panel A is a line graph of load at failure (strength) of blank wet spun PLLA fibers as a function of polymer concentration.

FIG. 25 panel B is a line graph of strain at failure (ductility) of blank wet spun PLLA fibers as a function of polymer concentration.

Figure 26A:
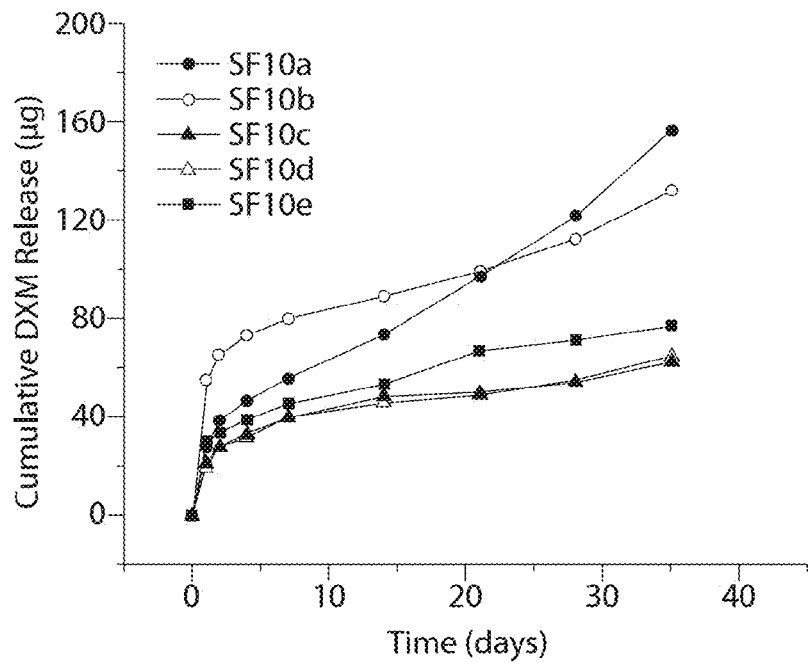
Figure 26B:
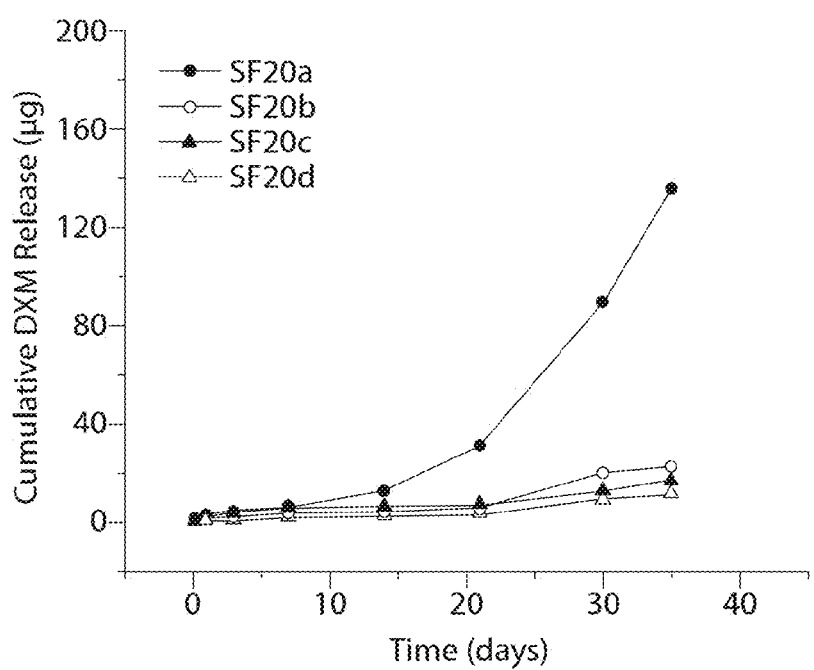

FIG. 26 panels A and B are line graphs of modulation of drug release kinetics by composite fibers made with different polymer compositions. The various composite fibers are: PLLA/PLGA (SF-10a), PLLA/PLGA/PVP (polyvinylpyrolidone; SF-10b), PLLA/$PLLA_{0.94}$ (SF-10c), PLLA/$PLLA_{0.94}$/PVP (SF-10d), and PLLA/PVP (SF-10e).

FIG. 26 panel A is a line graph of drug release profiles of 10 mg wet spun composite monofilaments prepared from 10% (w/v) polymer solution loaded with 2.6% (w/w) DXM.

FIG. 26 panel B is a line graph of drug release profiles of 10 mg wet spun composite monofilaments prepared from 20% (w/v) polymer solution loaded with 1.5% (w/w) DXM.

Figure 27A:
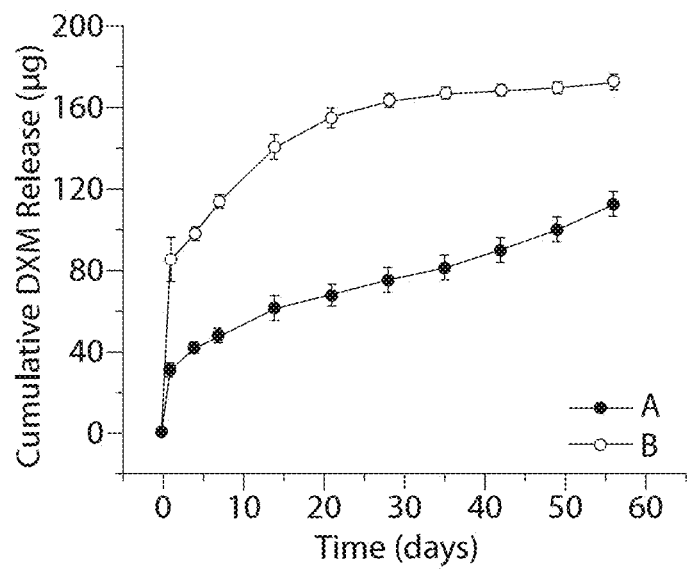
Figure 27B:
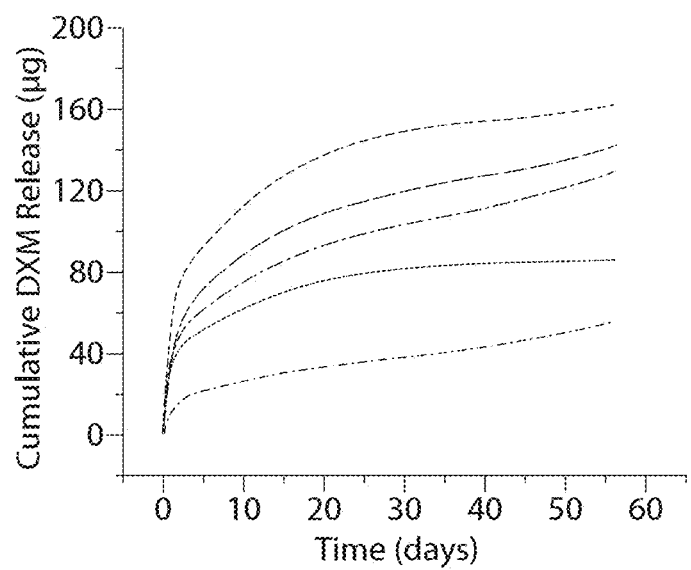
Figure 27C:
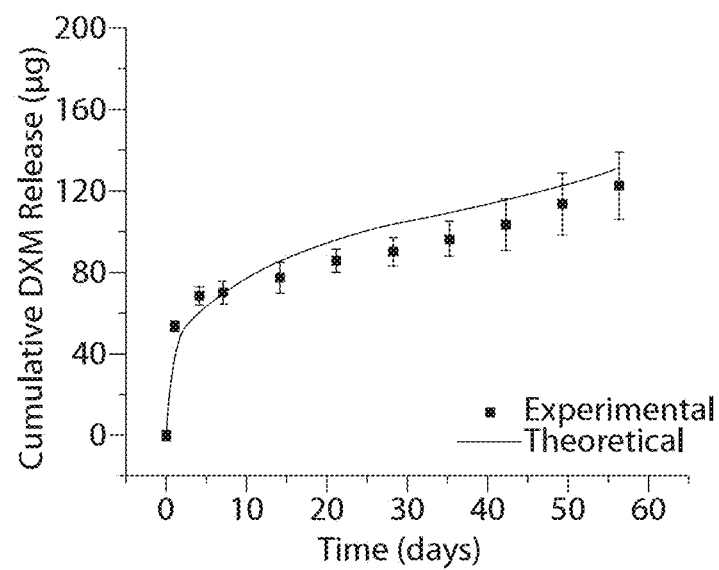

FIG. 27 panels A-C are line graphs of release kinetics of DXM from multifilament yarns.

FIG. 27 panel A is a line graph of drug release profile traces of 10 mg wet spun composite monofilaments prepared from 10% (black circles) and 20% (open circles) (w/v) polymer solutions loaded with 2.8 and 2.4% (w/w) DXM, respectively. Mean S.D. are represented.

FIG. 27 panel B is a line graph of multiple theoretical predictions (traces) of drug release kinetics of DXM-loaded multifilament yarns as a function of composition of single monofilament. Each monofilament is a 6-ply yarn combination made of formulations 'A', which is a 10% (w/v) polymer composite, and 'B', which is a 20% (w/v) polymer composite. From top to bottom the monofilament compositions are: 1A+5B, 5A+1B, 4A+2B, $3A_{blank}$+3B, and $3A+3B_{blank}$.

FIG. 27 panel C is a plot of drug release profiles of 10 mg 6-ply multifilament yarns produced by 'Z' twisting 4 monofilaments of formulation 'A' and 2 filaments of formulation 'B' (black squares) in comparison to the predicted release calculated using equation 7.

Figure 28:
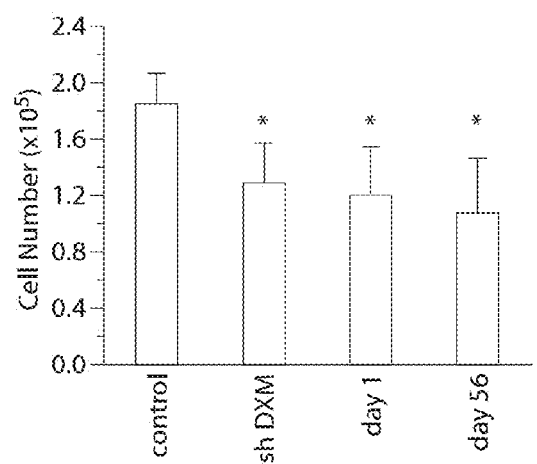

FIG. 28 is a bar graph of biological activity of eluted dexamethasone from multifilament yarns. Dexamethasone treatment inhibits proliferation of human aortic valve interstitial cells (hVICs). Cell number was determined after treatment with $10^{-7}$ mol $L^{-1}$ DXM for 72 hours. DXM eluted from 6-ply multifilament yarns after 1 day and 56 days were observed to have the same biological activity as fresh, unencapsulated drug. Mean±S.D. are presented; *$p<0.05$ compared to control by ANOVA.

Figures 29A, 29B, 29C:
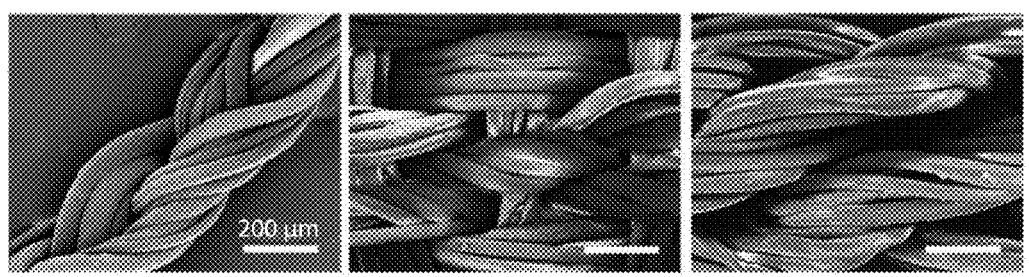

FIG. 29 panels A, B, and C are scanning electron micrographs, respectively of braided, woven, and complex geometry knitted wet spun multifilament yarns.

Figure 30:
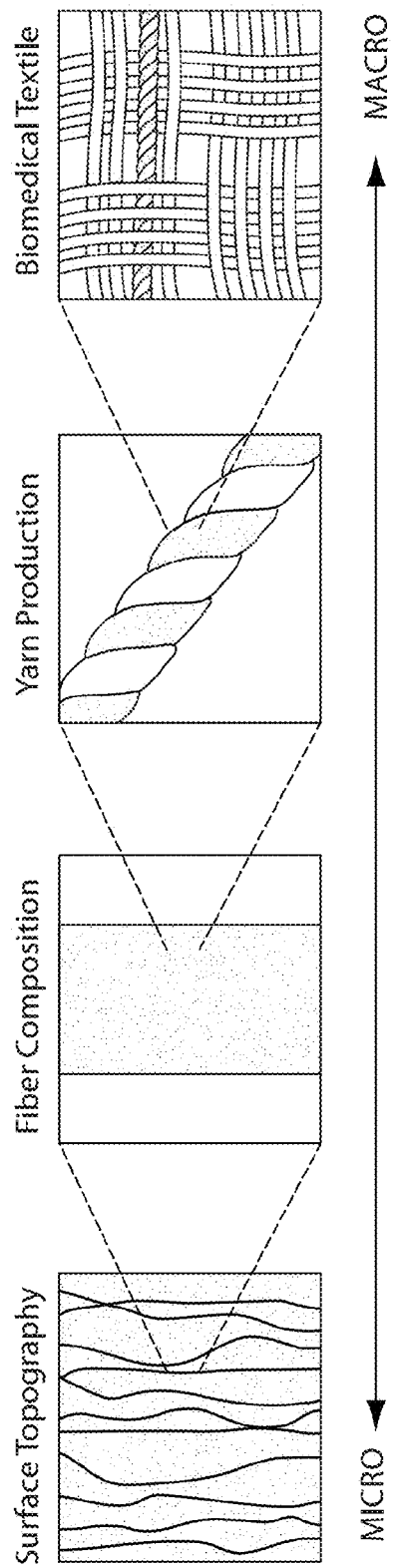

FIG. 30 is a drawing of four different levels of hierarchy in the design of therapeutic biomedical textiles. A bottom-up approach (left to right) is demonstrated for fabrication of wet spun filaments as simple building blocks (micro) for the formation of macro-level scaffolds.

DETAILED DESCRIPTION

Drug loaded micron-scale fibers and methods for their production provided herein are useful for a variety of applications, for example, surgical reconstruction. Local, tunable drug diffusion is useful for constructing anti-neoplastic or immune-privileged boundaries, for example, in the context of reconstructive surgeries and control of local wound healing, fibrosis, scaring, and injury responses including calcification. In vascular reconstructions, modulation of anastamotic healing offers potential to improve patency rates for microvascular repairs, and their presence in blood vessels opens the possibility for prolonged, regional, systemic delivery of therapeutic molecules via the circulation for targeted downstream effects.

Polymeric fibers are used in the design of many biomedical implants such as vascular implants, soft tissue implants, surgical sutures, implants for hernia and nerve repair, dialysis devices, therapeutic implants, wound dressings and tissue engineering (TE) scaffolds. Over 25 million people in United States rely on implanted medical devices, and demand for therapeutic implants increase by 8% annually (Selvam et al. Biomaterials, 2011; 32, 7785-7792). Further sutures are known to increase the risk of infection (Katz et al. Ann Surg 1981; 194, 35-41). Advances in polymer and drug delivery sciences have led to the evolution of engineered fibers for use as drug delivery vehicles. Design of pharmacologically active fibers has increased (Shibuya et al. Laryngoscope 2003; 113 (10:1870-1884; Kim et al. J Control Release 2004; 98(1):47-56; Zurita et al. Macromol Biosci 2006; 6(9):767-775; Yilgor et al. Biomaterials 2009; 30(21):3551-35). Drug eluting fibers have the potential to be knitted, woven, or braided into biotextiles for the release of a multitude of therapeutics with micron-scale accuracy (Tuzlakoglu et al. Tissue Eng Part B Rev 2009; 15(0:17-27).

Polymeric fibers may be fabricated using melt spinning, dry spinning, wet spinning or electrospinning. Melt spinning requires processing temperatures as high as 270° C. Dry spinning is restricted to polymers that dissolve in volatile solvents. Wet spinning is a technique in which a polymer dissolved in a solvent is extruded through a spinneret and into a non-solvent. Although, the solvent is miscible with the non-solvent, the polymer is not, and the polymer precipitates in the non-solvent in a continuous stream turning into a solid filament (Gupta et al. 2007 Prog Polym Sci 32(4):455-482). Electrospinning is suitable for ultrafine nano fibers which have insignificant mechanical strength.

Polymer fiber delivery systems by impregnating therapeutics into the core of hollow fibers, entrapping therapeutics within fibers, and chemically crosslinking or adsorbing therapeutics to the surfaces of fibers have been attempted. High surface area to volume ratio of fibers is advantageous for mass transfer and efficient drug release. Release of a model protein, bovine serum albumin (BSA), from the hydrogel cores of co-extruded wet spun PLLA fibers fabricated by Crow et al. exhibited sustained delivery up to eighty days in vitro (Crow et al. Biopolymers 2006; 81(6): 419-427). Sustained delivery of a model hydrophilic anti-cancer drug, 5-fluorouracil, was obtained by impregnating the drug within wet spun PLLA fibers for up to twenty-one days in vitro (Gao et al. J Control Release 2007; 118(3): 325-332). Jung et al. showed that the delivery of cell-permeable gene complexes from PLLA scaffolds improved the transfection of stem cells attached to the surfaces of fibers in comparison to bolus delivery strategies (Jung et al. J Control Release 2011; 152(2): 294-302).

Little is known about the effects of drug incorporation on mechanical integrity of the fibers (Chang et al. J Biomed Mater Res A 2008; 84(1): 230-237; Mack et al. J Control Release 2009; 139(3): 205-211; Rissanen et al. J Appl Polym Sci 2010; 116(4):2174-2180; Williamson et al. Tissue Eng 2006; 12(1):45-51). "Smart" fiber delivery systems are needed that are multi-functional, and provide both physical and pharmaceutical support.

An aspect of the invention provides a composition for delivering a therapeutic agent including: a multi-layer polymeric microstructure including the therapeutic agent, such that the therapeutic agent is located or compartmentalized in an inner core of the microstructure and is characterized by controllable release from the composition. In an embodiment of the composition, the microstructure comprises poly-1-lactic acid (PLLA) and poly-lactic-co-glycolide (PLGA). In an embodiment of the composition, the composition is porous.

In various embodiments of the composition, the therapeutic agent includes at least one selected from the group of: a drug, a protein, a sugar, a carbohydrate, and a nucleotide sequence. In a related embodiment of the composition, the protein includes at least one of the group selected from: a growth factor, an immunoglobulin (antibody), an enzyme, and an antibiotic. In an embodiment of the composition, the nucleotide sequences include a vector. In an embodiment of the composition, the vector comprises a viral vector or a bacterial vector. In an embodiment of the invention, the therapeutic agent includes dexamethasone. In an embodiment of the composition, the therapeutic agent includes a glycoprotein such as a Nog (Noggin) protein.

In an embodiment of the composition, the composition includes at least one selected from the group of: a fiber, a suture, a sphere, an implant, and a scaffold.

An aspect of the invention provides a method of producing a binary phase composition including: mixing a plurality of polymers with a solvent to form a resulting polymer\solvent material; and wet spinning the material by phase inversion, thus producing the binary phase composition. In an embodiment of the method, prior to mixing the plurality of polymers with the solvent, the method includes contacting the plurality with a therapeutic agent.

In an embodiment of the method, the therapeutic agent comprises at least one of the group selected from: a drug, a protein, a sugar, a carbohydrate, and a nucleotide sequence. In an embodiment of the method, the therapeutic agent is at least one of the group selected from: anti-coagulant, anti-tumor, anti-viral, anti-bacterial, anti-mycobacterial, anti-fungal, anti-proliferative, anti-inflammatory, anti-apoptotic, immunosuppressant, and pro-apoptotic. In a related embodiment of the method, the anti-inflammatory is selected from: a steroid and a non-steroidal anti-inflammatory agent (NSAID). For example the steroid is selected from the group of: a cortisone compound for example a dexamethasone; and a sex-related hormone.

In an embodiment of the method, the solvent includes at least one selected from the group of: chloroform, dichloromethane, ethyl acetate, diethyl ether, acetic acid, hexane, ethanol, methanol, acetone, tetrahydrofuran, toluene, dimethyl sulfoxide, acetonitrile, and a combination thereof. In various embodiments of the method, wet spinning includes loading the material into a syringe, and dispensing the material into a coagulation bath including a non-solvent for example petroleum ether. In an embodiment of the method, the coagulation bath includes petroleum ether. In various embodiments of the method, a difference between the solubility parameter of the solvent and the solubility parameter of the non-solvent affects the rate of solidification and the degree of crystallinity of the microstructure. The difference between the solubility parameter of the solvent and the solubility parameter of the non-solvent is selected from one of the following: less than about 12 units, less than 10 units, less than 9 units, less than 8 units, less than 7 units, less than 6 units, less than 5 units, less than 4 units, less than 3 units, less than 2 units and less than 1 unit. In various embodiments, the difference is less than about 2-4 units, less than about 4-6 units, less than about 6-8 units, or less than about 8-10 units. In various embodiments, the difference is varied to modulate rate of crystallization of the composition. In a related embodiment, the plurality of polymers includes a polymer matrix or a composite material. For example, the polymer matrix is bioabsorbable.

An aspect of the invention provides a method of treating a subject having a medical condition including: contacting the subject with a composition including a multi-layer polymeric microstructure including a therapeutic agent, such that the therapeutic agent is located in an inner core of the microstructure and is characterized by controllable release from the composition.

In a related embodiment of the method, the composition includes at least one selected from the group of: a fiber, a suture, a sphere, an implant, and a scaffold. In various embodiments of the method, the medical condition is at least one selected from the group of: a burn, a cut, an abrasion, a laceration, a pathology, a cancer, and an infection. In a related embodiment of the method, the microstructure includes poly-1-lactic acid (PLLA) and poly-lactic-co-glycolide (PLGA). In an embodiment of the method, the therapeutic agent comprises at least one of the group selected from: a drug, a protein, a sugar, a carbohydrate, and a nucleotide sequence. In various embodiments of the method, the protein includes at least one of the group selected from: a growth factor, an immunoglobulin, an enzyme, and an antibiotic. In an embodiment of the method, the nucleotide sequence includes a vector. In a related embodiment of the method, the vector includes a viral vector or a bacterial vector. In an embodiment of the method, the therapeutic agent is a corticosteroid for example a dexamethasone.

An embodiment of the invention provides a kit for treating a subject in need of medical treatment including: a composition for delivering a therapeutic agent including a multi-layer polymeric microstructure including the therapeutic agent, such that the therapeutic agent is located in an inner core of the microstructure and is characterized by controllable release from the composition; instructions for use; and, a container.

In related embodiments of the kit, the microstructure includes poly-1-lactic acid (PLLA) and poly-lactic-co-glycolide (PLGA). In an embodiment of the kit, the therapeutic agent includes at least one selected from the group of: a drug, a protein, a sugar, a carbohydrate, and a nucleotide sequence. In various embodiments of the kit, the protein includes at least one selected from the group of: a growth factor, an immunoglobulin, an enzyme, and an antibiotic. In an embodiment of the kit, a nucleotide sequence includes a vector. In a related embodiment of the kit, the vector includes a viral vector or a bacterial vector. In an embodiment of the kit, the therapeutic agent includes dexamethasone. In an embodiment of the kit, the composition includes at least one selected from the group of: a fiber, a suture, a sphere, an implant, and a scaffold.

The composition and methods described herein are provided for drug encapsulation and processing conditions that affect the mechanical integrity of microfibers, including producing microfibers that perform a surgical mechanical function and simultaneous drug delivery. Drug-drug and drug-polymer interactions were evaluated herein using wet spun PLLA microfibers loaded with 1.0, 2.4, and 4.8% (w/w) DXM. In the spinning of semi-crystalline polymers, the crystalline regions of the polymer contribute to strength. PLLA was selected herein for wet spinning because of its material properties. PLLA contains ester groups and DXM contains two carbonyl and three hydroxyl groups. Without being limited by any particular theory or mechanism, hydrogen bonding occurs between the carbonyl oxygen atoms in PLLA chains and the hydroxyl hydrogen atoms in DXM. Hydrogen bonding during incubation is enabled as the amorphous regions of the polymer become more mobile.

Wet spinning is a technique that is here applied to drug delivery technologies with advantages of ambient temperatures manufacture. Wet spinning is initiated by dissolving a polymer in solvent. The dissolved solution is extruded through a spinneret and into a non-solvent coagulation bath. The solvent is miscible with the non-solvent, and the polymer in solution is not, and a continuous polymer stream precipitates into a solid filament (Gupta et al. 2007 Prog Polym Sci 32(4):455-482). Wet spinning is used also for encapsulation of water-soluble drugs since both the solvent and coagulant can be non-aqueous, which produces a hydrophobic environment, thereby significantly reducing the leaching of water-soluble drugs from during the encapsulation process. A broad range of bioactive agents including antibiotics, heparin, proteins, growth factors, genes, and even viruses have been successfully wet spun into fibers for many biomedical applications (Blaker et al. Biomaterials 2004 25(7-8): 1319-1329; Pasternak et al. Int J Colorectal Dis 2008; 23(3): 271-276; Hirano et al. J Biomed Mater Res 2001; 56(4): 556-561; Cronin et al. J Biomed Mater Res A 2004; 69(3): 373-381; Hwang et al. Langmuir 2008; 24(13): 6845-6851; Crow B B et al. Biopolymers 2006; 81(6): 419-427; Jung et al. J Control Release 2011; 152(2): 294-302; Chiang et al. Adv Mater 2007; 19(6): 826-827).

PLGA and PLLA are biodegradable materials and have FDA approval for many medical applications. Three proteins of different molecular weights, insulin (5.8 kDa), lysozyme (14.3 kDa), and bovine serum albumin (66.0 kDa) were encapsulated in PLGA and PLLA microfibers to analyze the effect of protein molecular weight and polymer type on release kinetics and intrinsic material properties of wet spun microfibers. The optimal protein loading of 2% (w/w) was determined based on the maximum amount of BSA that was loaded into 20% (w/v) polymer concentrations without disrupting the continuous formation of fibers. Therapeutics with molecular weights higher than BSA are envisioned to be incorporated into fibers by increasing the concentration of the spin dope, increasing the molecular weight of the polymer, or by decreasing the theoretical loading of the protein. Other polymers are fabricated into wet spun microfibers by selecting the appropriate solvents and nonsolvents.

Fibers prepared from cryogenic emulsions were observed to have non-circular skin-core structure consistent with the wet extrusion process. Fiber shape is in part a result of solvent and nonsolvent counter-diffusion. If the rate of solvent diffusing out is higher than the rate of nonsolvent diffusing in, the fiber structure collapses and non-circular shapes such as lobed 'kidney' and 'dog bone' are formed (Sobhanipour P et al., Thermochim Acta, 2011; 518:101-106). Rapid surface coagulation during phase inversion leads to the entrapment of solvent and nonsolvent within the precipitating microfilament (Rissanen M et al., J Appl Polym Sci, 2008; 110:2399-2404). Porous structure is formed by evaporation of solvent and nonsolvent after microfilament solidification. PLGA and PLLA microfibers prepared using methods herein have significantly less voids than poly(L,D-lactic acid) fibers prepared from water-in-oil (W/O) emulsions by Rissanen et al. (Rissanen M et al., J Appl Polym Sci, 2010; 116:2174-2180). Pores were attributed to air bubbles from emulsion formation and rapid phase separation during filament precipitation in the spin bath. Cryogenic emulsion process described herein reduces the potential for large voids by removing the water phase from the primary W/O spin dope. Void formation was reduced by encapsulating drugs as solid particles within wet spun microfibers (Gao H et al., J Control Release, 2007; 118:325-332), and hydrophilic drugs encapsulated were not micronized and thus were characterized by large particles imbedded within the fibers and on the surfaces of fibers.

Thermal analyses of fibers (t=0) showed that the glass transition temperatures of PLGA formulations did not substantially decrease with protein loading, nor did the relative crystallinity of PLLA formulations. These results indicated that the long duration (~1.5 h) of the fibers in the nonsolvent bath induced solvent-induced crystallization (SINC). An increase in glass transition temperature was observed among formulations with incubation (t=63). The increase in glass transition temperature was due to increased amorphous chain mobility at the incubation temperature (37° C.) and potential formation of ordered structures. Similar thermal induced crystallization with incubation were observed in the preparation of DXM-loaded PLLA microfibers.

X-ray diffraction studies were used to further evaluate the molecular morphology of wet spun fibers. The PLLA samples in Examples herein, including blank fibers, had similar x-ray diffraction patterns, and SINC was persistent despite the presence of the encapsulated protein. In the degraded PLLA formulations, the peak at 24.4° disappeared at 63 day incubation due to hydration and re-orientation of the polymer. The new sharp peak that appeared at 16.5° corresponded to amorphous chain restructuring of low molecular weight chains in the polymer with incubation. Re-ordering of shorter oligomers and strong secondary interactions between proteins and polymers further contributed to this effect.

The molecular weight of the protein and polymer structure also influenced the physical properties of wet spun microfilaments. Both polymers exhibited significantly reduced tensile strength with increased protein molecular weight and PLLA microfibers loaded with BSA were observed to have the greatest tensile loss. Without being limited by any particular theory or mechanism, the reduced tensile strength is in part a result of the differences in polymer structure between PLGA and PLLA. PLLA is a semi-crystalline polymer whereas PLGA is amorphous. In general, the amorphous regions of a polymer require less force to deform in comparison to the crystalline regions. At high protein loading with BSA, the material properties of PLGA and PLLA microfibers were significantly weakened possibly due to protein particles acting as material defects within the polymer lattice during elastic deformation. The fusion of BSA particles also contributed to these results, as was observed with scanning the electron micrographs (FIGS. 10 and 11). However, BSA-PLGA microfibers were observed to have higher tensile strengths and elongations until failure than BSA-PLLA formulations. The amorphous PLGA appeared to reduce the tensile loss and embrittlement of BSA-loaded microfibers to a lesser degree relative to BSA-loaded PLLA formulations. Differences between amorphous PLGA and semi-crystalline PLLA were reflected in elastic moduli. PLGA microfibers had similar resistance to deformation regardless of protein loading. PLLA is semi-crystalline, therefore low protein loading provided slightly increased resistance to deformation likely due to protein particles reinforcing the amorphous regions of the polymer. Protein-polymer interactions at the molecular level also affect the physical properties of the microfiber. Strong secondary interactions between proteins and polymers, such as hydrogen bond formation and ionic interactions helped to maintain the material properties of polymeric microfibers with INS and LZ loading. Encapsulation of small molecules decreased wet spun fiber strength and ductility (Mack B C et al., J Control Release, 2009; 139:205-211; Williamson M R et al., Biomaterials, 2004; 25:5053-5060; Chang H I et al., J Biomed Mater Res Part A, 2008; 84:230-237). In examples herein, the effect of three proteins on protein-loaded microfibers was evaluated, and protein particle size was observed to play a critical role in the tensile strength of polymeric wet spun microfibers.

Protein release from wet spun microfibers was found to depend on protein molecular weight. These data show that the amount of protein released is controlled primarily by diffusion. Three phases were seen in the release of INS from PLGA and PLLA formulations, indicating that some degradation was occurring. In the degradation of polyesters, random cleavage of ester linkages along the polymer backbone breaks long polymer chains into short fragments that may not be water-soluble. A reduction in the molecular weight increases hydrophilicity, and additional release of INS with little polymer degradation was observed by DSC and FT-IR analyses, due to slow degradation of wet spun aliphatic polyesters with similar molecular weights (Crow B B et al., Tissue Engineering, 2005; 11:1077-1084; Nelson K D et al., Tissue Engineering, 2003; 9:1323-1330).

The dynamic mechanical properties of drug-eluting wet spun fibers in vitro were evaluated in Examples herein. Dexamethasone (DXM), a synthetic anti-inflammatory glucocorticoid was used in compositions, methods and kits herein as the model hydrophobic drug. Local delivery of DXM from microspheres has been shown to reduce cellular immune response to medical implants (Hickey et al. J Biomed Mater Res 2002; 61(2): 180-187; Patil S D et al. Diabetes Technol Ther 2004; 6(6): 887-897; Barcia et al. Exp Eye Res 2009; 89(2):238-245). Therefore, DXM elution as described herein is beneficial for reducing unwanted inflammatory responses of fibrous implants. Examples herein analyzed the drug-polymer interactions and the effects of DXM loading and release on the material properties of wet spun PLLA fibers.

Wet spinning by phase inversion was found in Examples herein to produce durable dexamethasone-eluting PLLA fibers that had prolonged release of drug and retained high mechanical strength. It was observed that these microstructures are useful as a fiber delivery system. Sustained release of drug from wet spun PLLA fibers has been a unfulfilled goal of researchers and industry, and Examples herein are the first to report a stable and controlled fiber based delivery system with linear release of <28% total encapsulated drug after eight weeks in vitro. Methods and systems herein produced fibers that have been woven or knitted into tissue-engineering TE scaffolds. Without being limited by any particular theory or mechanism of action, it is here envisioned that dexamethasone included in microstructure compositions (e.g., fibrous scaffolds) reduced innate immune response and resulted in the mechanical support suitable for tissue integration. Furthermore, the addition of an inert hydrophobic molecule, such as dexamethasone, into wet spun fibers resulted in the mechanical properties of microfilaments, and decreased the burst release of hydrophilic therapeutics. A stable delivery system using a porous polymeric microstructure composition was obtained that is physically manipulatable/easily shaped, and delivers controlled release of therapeutics and maintains mechanical strength. The compositions, methods, and kits using a multi-layer polymeric microstructure are useful for many therapeutic applications including regenerative medicine and tissue engineering.

Fabrication of biologically active fibers for integrating into existing biomedical implants, for instance, local, controlled delivery of anti-inflammatory drugs to surrounding tissues would function to reduce unwanted inflammatory cell infiltrates and increase the longevity of implanted biomaterials. A bench-top technique for the scale up of monofilaments into multifilament yarns was developed to enhance the handling capabilities of wet spun filaments and to demonstrate the ability to tune drug release kinetics.

The wet spinning technique in Examples herein is a versatile method for the production of continuous micron-sized fibers. The surface topography of wet spun filaments was manipulated by altering wet spinning parameters. In general, quick quenching yields fibers with smooth surfaces (Xiang H B et al., Macromol Res, 2011; 19:645-653). Therefore, it was possible to create fibers with micrometer-range features such as grooves, ridges, and spherical protrusions by decreasing the polymer solution concentration, slowing the counter-diffusion of solvent and nonsolvent, altering the residence time in the coagulation bath, or simply applying tension through solution- and post-drawing methods. Altering the surface topography of wet spun fibers is beneficial for host tissue integration and wound healing by enhancing contact guidance and cellular attachment (Cao H et al., J Biomed Mater Res Part A, 2010; 93:1151-1159).

To demonstrate the ability to modulate drug release from wet spun filaments, fibers with varying polymer compositions were produced, including compositions having excipients such as PVP, and by using different polymer concentrations. Drug-loaded formulations were as-spun, solution-drawn or post-drawn, depending on the rate of precipitation and counter-diffusion of solvent and nonsolvent. Each of these processes was developed to determine whether wet spun fibers can be used to design hybrid devices, ones that perform a mechanical function and simultaneously deliver drugs. Examples herein show the complexity of designing a wet spun delivery system and the scale up of monofilaments into multifilament yarns.

Overall, DXM release of wet spun filaments of similar polymer concentration was dependent on the hydrophilicity of the composite formulation. For 10% (w/v) solution-drawn composite formulations, the highest drug release rates were achieved by adding PLGA and PVP. Since PVP is a water-soluble polymer, increased drug release was attributed to pore formation from the solubilization of PVP in buffer solution. After the initial burst period, the release of drug from solution-drawn 10% (w/v) formulations was favored by the swelling capability of the fibers. As-spun formulations with 20% (w/v) solutions containing PLLA and PLGA also showed the release of DXM was dependent on the hydrophilicity of the filaments. A substantial difference in drug release kinetics of 20% (w/v) composite fibers was achieved with the addition of 50% PLGA content. The ability to prolong the release of drug was also apparent by increasing the polymer concentration from 10% to 20% (w/v).

Post-drawn composite formulations selected for multifilament yarn production were observed to have increased DXM release with increased PLGA and PVP addition, despite differences in overall polymer concentration. Fibers spun from 10% (w/v) solutions were observed to have reduced DXM burst release in comparison to fibers spun from 20% (w/v) solutions. For these formulations, variations in DXM release kinetics were attributed to processing conditions. The PVP content in 10% (w/v) formulations was less than that in 20% (w/v) formulations, which resulted in the decrease in the initial burst release of DXM. Nano-sized pores on the surfaces of 20% (w/v) composite solutions also modulated drug release by increasing buffer penetration. Surface pore formation is a result of the rapid evaporation of solvent entrapped within the precipitating fiber during winding. Filaments spun from 10% (w/v) solutions also displayed a dense cross-sectional morphology. Cross-sectional pores are caused by the entrapment of solvent during spin dope solution precipitation. Composite fibers from 10% (w/v) solutions were observed to have less polymer concentration to block the counter-diffusion of solvent and nonsolvent, resulting in significantly less cross-sectional porosity in comparison to 20% (w/v) solutions. While both 10% and 20% (w/v) composite fibers experienced similar forces during drawing, 10% (w/v) solutions were observed to have less resistance to deformation as judged by the grooved surface topography.

The therapeutic range of DXM delivery to treat post-operative inflammation from various biomaterials has been evaluated in a number of animal models (Barcia E et al., Exp Eye Res 2009; 89:238-245; Dang T T et al., Biomaterials, 2011; 32:4464-4470; 39; Hickey T et al., J Biomed Mater Res, 2002; 61:180-187; Patil S D et al., Diabetes Technol Ther, 2004; 6:887-897; Selvam S et al., Biomaterials, 2011; 32:7785-7792). Hickey et al. evaluated the potential of localized DXM delivery from PLGA microspheres to suppress inflammatory responses to cotton threads implanted subcutaneously in rats (Hickey T et al., J Biomed Mater Res, 2002; 61:180-187). They showed DXM treatment was most effective when delivered as a burst release followed by a slow release (3-30 µg day-1) over the course of 30 days in vivo. Microspheres and hydrogel composites have been evaluated by others for the continuous release of DXM to treat biomaterial-driven inflammation and release rates of 0.17-7.2 µg day$^{-1}$ were found to be effective in modulating host immune responses (Barcia E et al., Exp Eye Res 2009; 89:238-245; Patil S D et al., Diabetes Technol Ther, 2004; 6:887-897). Real-time inflammatory response to biomaterial implants has been investigated using non-invasive fluorescence imaging techniques (Dang T T et al., Biomaterials, 2011; 32:4464-4470; Selvam S et al., Biomaterials, 2011; 32: 7785-7792). These results showed that local delivery of DXM from PLGA microspheres was successful in significantly reducing biomaterial-driven inflammatory responses continuing until one month in vivo.

To engineer fibers with various release profiles of biologically active drug post-drawn filaments were scaled up into 6-ply multifilament yarns. Yarn production did not affect the predicted release of DXM from individual filaments (FIG. 27 panel C). The biological activity of eluted drug also was preserved until 56-day incubation. Drug-eluting yarns were formed from a combination of several types of individual monofilaments for the prolonged release of a multitude of therapeutics with retained biological activity. Drug release profiles were further tuned to meet specific clinical needs by altering the polymer composition, molecular weight and concentration as previously discussed. Additionally, wet spun fibers were used as conduits for the long-term delivery of other biologically active drugs and/or proteins.

The tensile properties of post-drawn monofilaments and 'Z' twisted multifilament yarns were characterized to evaluate their use as multifunctional delivery systems. Increasing the polymer concentration did not result in increased tensile properties as was found with blank fibers spun from PLLA only (FIG. 25). Polymer chains align in the direction of shear flow during spinning (Graessley W W, J Chem Phys, 1965, 43:2696-2703). Dilute polymer solutions have less polymer chains and more mobility to align in the direction of flow, promoting a higher degree of chain orientation along the fiber axis. Thus, it is possible that the molecular orientation and crystalline morphology of post-drawn 10% and 20% (w/v) fibers are different. Post-drawing increases the degree of orientation, density and fiber crystallinity (Arbab S et al., Polym Bull, 2011; 66:1267-1280; Williamson M R and Coombes A G, Biomaterials, 2004; 25:459-465). Longitudinal striations on the surfaces of 10% (w/v) fibers indicated that post-handling processes also influenced molecular orientation during fiber drawing. When fibers are under tension, such as in filament drawing, the amorphous units of the polymer begin to unfold, allowing for a reduction in free volume and amorphous polymer chain alignment until fracture.

Monofilaments spun from 10% (w/v) solutions were observed to have similar ductility as compared to 20% (w/v) solutions. One would expect increased polymer concentration to lead to increased strain at failure (FIG. 25). However, the cross-sectional morphology of composite fibers was very different, unlike the as-spun fibers made from PLLA only. The residence time of post-drawn composite fibers prepared for multifilament yarn fabrication was ~6 min, whereas as-spun PLLA fibers remained in the coagulation bath until the spin dope was extruded, yielding a residence time of about 1.5 hours. Reduced duration of residence in the coagulation bath leads to more porous fibers by decreasing the growth rate of voids, and time available for growth during phase separation. Drug encapsulation did not considerably affect the material properties of monofilaments.

The United States Pharmacopeia (USP) determines the standards specifying test procedures and product specifications for surgical sutures including the knot-pull tensile strength for bioresorbable sutures. The average maximum tensile stress for DXM-loaded multifilament yarns was approximately 450 mN, or 0.05 kgf, equivalent in strength to a 9-0 (0.030-0.039 mm diameter) absorbable synthetic suture (United States Pharmacopeia and National Formulary (USP 34-NF 29), United States Pharmacopeial Convention, Rockville, Md., 2010). The multifilament yarns are much larger in diameter than 9-0 sutures and their handling capabilities demonstrate the potential to hybridize wet spun fibers with existing surgical sutures to meet tensile strength specifications. Using textile industry embroidery technologies, it is possible to weave, braid, or knit drug-eluting yarns with or around existing sutures. Since there was much strain left in the fibers after the wet spinning process, it is envisioned that mechanical properties of drug-eluting filaments can be improved through industrial-scale post-drawing techniques. Multifilament drug-eluting yarns described in Examples herein stretched over 100% of their initial length before failure. Mechanical stretching is envisioned to be useful to decrease the ductility of yarns and increase tensile strength. Stretching is similarly envisioned to be applied to individual fibers prior to multifilament yarn formation.

A multifilament yarn with tunable DXM release kinetics that is controllable through the combination of constituent monofilaments is described. The spatiotemporal release of therapeutics is further controlled by the location of specific yarns within a 3-dimensional biomedical implant. Examples herein show that the encapsulation of dexamethasone within wet spun fibers does not weaken mechanical strength or lead to fiber embrittlement. Drug-eluting yarns were not as strong as conventional melt spun sutures, and were capable of physical manipulation and have the potential to be incorporated into existing biomedical textiles. Compositions and methods herein demonstrated the feasibility of making micron-scale alterations to the surface topography of wet spun fibers by applying stretch and varying wet spinning processing conditions. The potential to alter the surface topography of monofilaments, tune the release kinetics of a biologically active therapeutics, and enhance the load bearing strength of wet spun fibers through multifilament twisting, makes wet spun yarns extremely valuable for many biomedical and drug delivery applications (FIG. 30). The diverse release kinetics achieved in Examples herein show an ideal release profile of potential therapeutics to decrease non-specific inflammatory responses to implanted biomaterials.

Methods and compositions herein include a therapeutic agent for example a vector or an antibody. Methods use construction of expression vectors containing a sequence encoding a protein operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to contain and express a protein encoding sequence. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989. Exemplary viral vectors include adenovirus vectors, lentivirus vectors, adeno-associated virus (AAV) vectors, and helper-dependent adenovirus vectors.

General methodologies for antibody production, including criteria to be considered when choosing an animal for the production of antisera, are described in Harlow et al. (Antibodies, Cold Spring Harbor Laboratory, pp. 93-117, 1988). For example, animals of suitable size such as goats, dogs, sheep, mice, or camels are immunized by administration of an amount of immunogen, such as the intact protein or a portion thereof containing an epitope from human protein, effective to produce an immune response. The technique of in vitro immunization of human lymphocytes is used to generate monoclonal antibodies. Techniques for in vitro immunization of human lymphocytes are described in Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Pharmaceutical Compositions

An aspect of the present invention provides pharmaceutical compositions or devices that contain a polymeric microstructure comprising a therapeutic agent. In related embodiments, the pharmaceutical microfiber composition is formulated sufficiently pure for administration to a human subject, e.g., to an abdomen, an eye, or an appendage of a human subject.

In certain embodiments, the therapeutic agent or agents are selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid.

In other embodiments, the agent is a compound, composition, biological or the like that potentiates, stabilizes or synergizes the effects of a microfiber on a cell or tissue. In some embodiments, the drug includes without limitation anti-tumor, antiviral, antibacterial, anti-mycobacterial, anti-fungal, anti-proliferative or anti-apoptotic agents. Drugs for inclusion in the microfiber are described in Goodman & Gilman's The Pharmacological Basis of Therapeutics, 9th Ed., Hardman, et al., eds., McGraw-Hill, 1996, the contents of which are herein incorporated by reference herein.

Therapeutically Effective Dose

Methods provided herein involves contacting a subject with a pharmaceutical microfiber composition, for example, administering a therapeutically effective amount of a pharmaceutical composition having an active agent within a polymeric microstructure comprising a therapeutic agent, to a subject in need thereof, in such amounts and for such time as is necessary to achieve the desired result.

The compositions, according to the method of the present invention are administered using an amount and route of administration effective for treating a subject. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., age, weight and gender of the patient; diet, time and frequency of administration; route of administration; drug combinations; reaction sensitivities; and tolerance/response to therapy. Long acting pharmaceutical compositions might be applied only once, for example as a suture or at convenient intervals such as every week, or every other week, once every month, or semi-annually, or annually depending on half-life and clearance rate of the microfiber device.

A therapeutically effective dose refers to that amount of active agent that ameliorates the symptoms or prevents progression of pathology or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population) and by release from the microfiber composition or device. The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

Administration of a source of expression of a protein is administration of a dose of a viral vector or a nucleic acid vector, such that the dose contains for example at least about 50, 100, 500, 1000, or at least about 5000 particles per cell to be treated.

Administration of Pharmaceutical Compositions

As formulated with an appropriate pharmaceutically acceptable carrier in a desired dosage, the pharmaceutical composition provided herein is administered to humans and other mammals topically such as ocularly (as by a microfiber application), nasally, bucally, orally, rectally, parenterally, intracisternally, intravaginally, or intraperitoneally.

Dosage forms for topical or transdermal administration of a microfiber inventive pharmaceutical composition include ointments, pastes, creams, lotions, gels, sprays, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes delivery devices, surgical devices, audiological devices or products which contain disclosed microfiber compositions (e.g., as supplied as a portion of gauze bandages or strips), and methods of making or using such devices or products. These devices may be coated with, impregnated with, bonded to or otherwise treated with the active agent as described herein.

Transdermal patches have the added advantage of providing controlled delivery of the active ingredients to the body. Such dosage forms can be made by dissolving or dispensing the active agent in the polymer. Absorption enhancers can also be used to increase the flux of the compound across the skin. The rate can be controlled by either providing a rate controlling membrane or by dispersing the compound in a polymer matrix or gel.

Compositions for rectal or vaginal administration are preferably microfiber suppositories which can be prepared by mixing the active agent(s) of the invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, and granules in which the microfiber device is manufactured in a form or size appropriate to be swallowed or maintained within the oral cavity A skilled person will recognize many suitable variations of the methods to be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. Therefore, it is contemplated to cover the present embodiments of the invention and any and all modifications, variations, or equivalents that fall within the true spirit and scope of the basic underlying principles disclosed and claimed herein.

Portions of the data described herein have been published as three articles, "Multifunctional polymeric microfibers with prolonged drug delivery and structural support capabilities", co-authors Lavin D M, Stefani R M, Zhang L, Furtado S, Hopkins R A, Mathiowitz E. *Acta Biomater.* 2012 May; 8(5): 1891-900; "A novel wet extrusion technique to fabricate self-assembled microfiber scaffolds for controlled drug delivery", co-authors Lavin D M, Harrison M W, Tee L Y, Wei K A, Mathiowitz E. *J Biomed Mater Res A.* 2012 October; 100(10): 2793-802; and "Effects of protein molecular weight on the intrinsic material properties and release kinetics of wet spun polymeric microfiber delivery systems", co-authors Lavin D M, Zhang L, Furtado S, Hopkins R A, Mathiowitz E. *Acta Biomater* 2013 January; 9(1):4569-78, which are hereby incorporated herein by reference in their entireties.

The invention having now been fully described, it is exemplified by the following examples and claims which are for illustrative purposes only and are not meant to be further limiting.

EXAMPLES

Example 1

Polymers and Reagents

Poly(L-lactic acid) (PLLA, $M_w$~120,000) was purchased from Lactel Biodegradable Polymers (Birmingham, Ala.).

Poly(D,L-lactic-co-glycolic acid) (PLGA) was purchased from Durect, (Cupertino, Calif.). Dexamethasone (DXM) and HPLC grade acetonitrile were purchased from Sigma-Aldrich (St. Louis, Mo.). Analytical grade petroleum ether (PE), dichloromethane (DCM), tetrahydrofluran (THE), and glacial acetic acid were purchased from Fisher Scientific (Pittsburgh, Pa.). PLLA (i.v.=1.04 dL/g in $CHCl_3$) and PLGA, 75:25 ester terminated (i.v.=0.55-0.75 dL/g in $CHCl_3$) were used in the fabrication of wet spun microfibers. Bovine serum albumin (BSA; Sigma), lysozyme (LZ; Sigma) and bovine zinc insulin (INS; Gibco) were used as model proteins in methods herein. Dichloromethane (Fisher) and petroleum ether (Fisher) were the solvent and nonsolvent used for wet spinning Sorbitan trioleate (Span 85, HLB 1.8) (Sigma) was used in PLGA microfiber formulations. The micro BCA protein assay reagent kit used to detect protein concentration was used according to the manufacturer (Fisher).

Example 2

Fabrication of Dexamethasone-Loaded Microfibers

PLLA (7.5% w/v), DXM-loaded (1.0%, 2.4%, 4.8% w/w) and unloaded (0% w/w) microfibers were wet spun by phase inversion. PLLA (526.9±0.3 mg) was dissolved in a co-solvent ratio of 6:1 (v/v) DCM to THF. DXM was added to the co-solvent solution at varying concentrations up to 3.6 mg/mL, near its maximum solubility. The addition of THF was necessary to increase DXM solubility within the spin dope. The polymer/drug solution was loaded into a 5 mL syringe fitted with a 22-gauge spinneret and placed in a syringe pump with a solution flow rate of 0.06 mL/min. Since DCM and THF are miscible with petroleum ether, the immersion of the spinneret into the coagulation bath resulted in continuous microfiber formation and subsequent encapsulation of DXM. A rotating mandrel placed above the spin bath was used to collect microfibers for further analysis. Each formulation in Examples herein was characterized from multiple regions of meter-long microfiber bundles spun at the same time from one spin dope solution.

Example 3

Methods of Analysis of Microfiber Morphology

Scanning electron microscopy was used to analyze the surface and cross-sectional morphology of wet spun microfibers. Fiber samples were placed on double-sided carbon tape and coated with a 50-100 Å layer of gold-palladium using a sputter coater (Emitech, Kent, England). Scanning electron microscopy was conducted using a Hitachi S-2700 (Tokyo, Japan) microscope with an accelerating voltage of 8 kV and a working distance of 12 mm. Micrographs was collected using a Quartz PCI digital imaging system. The average microfiber diameter was measured using NIH ImageJ software (Bethesda, Md.) from 10 fields of view taken at 100× magnification. The porosity was measured also from cross-sectioned microfibers and calculated as pore area divided by total cross-sectional area.

Example 4

Determination of Microfiber Drug Loading

Drug-loaded and control fiber bundles (5.0±0.3 mg) were dissolved in 5 mL of 6:1 (v/v) DCM to THF until a clear solution was obtained. The encapsulation efficiency of DXM-loaded microfibers was determined by UV absorbance at 239 nm using quartz cuvettes to minimize background noise at the reading frequency. The percentage of drug encapsulated was calculated as the amount of DXM detected in microfibers relative to the total amount of drug added to the spin dope solution. Two samples from each formulation were assayed in duplicate.

Example 5

Dexamethasone Release Analysis

As-spun microfibers from each batch (21.0±2.0 mg) were incubated with 2 mL PBS, pH 7.4 in capped micro centrifuge tubes and kept at 37° C. At each time point, 1 mL of the releasate was removed and replaced with fresh PBS. Prior to release analysis, DXM releasates were lyophilized and reconstituted in a mobile phase of 52:48 (v/v) 2 mM acetate buffer (pH 4.8) to acetonitrile. DXM detection was performed using a 3.9×150 mm Novapack C-18 column with a mobile phase flow rate of 1 mL/min at 240 nm after an average elution time of 2 minutes. Drug concentration was determined by comparing the area under the peak at the expected elution time with a calibration curve constructed from samples of known concentration.

Example 6

Degradation Analysis

PLLA microfibers (23.0±2.0 mg) prepared by wet spinning were weighed in microcentrifuge tubes and incubated in 2 mL PBS (pH 7.4). The tubes were capped and placed at 37° C. The duration of the degradation analysis was eight weeks with weekly terminal time points. At each sampling interval, the PBS solution was removed and the supernatant pH measured using a Corning pH meter (Medfield, Mass.). The remaining microfiber bundles were washed three times in distilled water and lyophilized for 24-48 hours.

Example 7

Differential Scanning Calorimetry (DSC) and Hyper DSC Analysis

The thermal properties of microfibers from terminal time points were analyzed for thermal transitions using a DSC-7 (Perkin Elmer) equipped with an Intracooler 2 intercooling system (Perkin Elmer). Samples were subjected to: cooling to −25° C.; heating to 250° C. at 10° C./min; cooling to −25° C. at 10° C./min; and reheating the sample to the upper limit again at the initial rate. Glass transition temperature, melting temperature, and change in enthalpy of the melt were measured from the resulting thermograms. The percent crystallinity ($X_c$) was also calculated using equation 1:

$$X_c = \frac{\Delta H_m}{\Delta H_{PLLA}} \times 100 \tag{1}$$

in which $\Delta H_m$ is the enthalpy of melting of the samples and $\Delta H_{PLLA}$ (93.7 J/g) is specific heat of melting of a 100% crystalline PLLA as reported in the literature (Fischer E W et al., Kolloid Z Z Polym, 1973; 251:980-990). The dispersion of solid drug particles not solubilized within the polymer matrix was also analyzed using a DSC-8500 (Perkin Elmer) capable of hyper DSC. Samples were subjected to heating from 20° C. to 310° C. at 200° C./min and compared to the thermogram of free DXM from the manufacturer.

Example 8

X-Ray Diffraction (XRD) Analysis

The structural properties of PLLA microfiber formulations were determined using an automated X-ray diffractometer (Siemens Diffraktometer D5000) with a Cu Kα (λ=1.54 Å) radiation. The diffraction angles (2θ) ranged from 6° to 60° with sampling intervals of $0.02° \, s^{-1}$. Diffraction signal intensity was monitored and processed using DiffracPlus Software (Bruker AXS).

Example 9

Mechanical Properties of PLLA Microfibers

Uniaxial tensile testing was used to characterize the mechanical properties of wet spun PLLA microfibers. Tests were performed at ambient temperature, humidity, and pressure using an Instron materials testing machine (Model 4442). Gauge length and elongation rate were defined in accordance to United States Pharmacopeia standards for absorbable sutures (The United States Pharmacopeia and The National Formulary 2011. Baltimore, Md.: United Book Press, Inc.; 2010 2011. Baltimore, Md.: United Book Press, Inc.; 2010). Microfibers were secured onto paper frames (25 mm×25 mm) with precut windows to define gauge length and region of loading. After clamping samples into the crossheads of the machine, the edges of each frame were cut leaving microfibers intact. Samples were loaded to failure at a constant elongation rate of 50 mm/min. Load cell measurements and displacement data from crosshead extension were converted into stress-strain data. Ultimate tensile strength, strain at failure, and elastic modulus were calculated from the resulting stress-strain curves. The ultimate tensile strength σ was calculated from the maximum force to failure F divided by the cross sectional area A, using the initial diameter of the fiber obtained from scanning electron micrographs with equation 2:

$$\sigma = FA^{-1} \quad (2)$$

Strain at failure ε was defined as the change in gauge length ΔL at fiber fracture over the original length of the fiber $L_o$ using equation 3:

$$\epsilon = \Delta L L_o^{-1} \quad (3)$$

Elastic modulus E was calculated within the linear elastic regime of the stress-strain curve using Hooke's law, whereby strain is linearly proportional to tensile stress using equation 4:

$$E = \sigma \epsilon^{-1} \quad (4)$$

Example 10

Statistical Analysis

One-way analysis of variance (ANOVA) tests were performed on mechanical data for wet spun microfibers using SPSS v.19 statistical software (Chicago, Ill.). Post hoc analyses were carried out using the Tukey multiple comparisons test. A p value of less than 0.05 was considered to be significant.

Example 11

Microfiber Extrusion and Morphology

PLLA spin dope solutions extruded into the petroleum ether coagulation bath underwent phase inversion within centimeters of the spinneret, forming an opaque white microfilament. Residence time was 5-10 seconds before microfibers were collected around a rotating mandrel placed above the spin bath. Samples were strong and spun easily, indicating quite fast and effective curing within this short time span. Representative scanning electron micrographs of microfibers are shown in FIG. 1 panels A and B. Wet spinning conditions produced 64.3±7.0 μm diameter microfibers with skin-core structures. Skin-core structure is common to wet spinning, and is caused by rapid surface coagulation leading to the entrapment of solvent and nonsolvent within the precipitating microfilament (Rissanen M et al., J Appl Polym Sci, 2008; 110: 2399-2404). Porous structure is formed once solvent and nonsolvent are evaporated after microfilament solidification. The solvents involved in the formation of the fiber play a major role in further crystallizing the polymer by solvent-induced crystallization (SINC). DXM-loaded and control microfibers were observed to have round cross-sectional geometry and relatively porous morphology with similar interconnectivity.

The average percent porosity of microfibers was observed to be 17.0±1.3 with an average pore size area of 1.26±0.06 $\mu m^2$ as determined from the micrographs of cross-sectioned microfibers. Microfibers displayed micron-rough surface topography with spherical protrusions similar to studies by Nelson et al. (Nelson K D et al., Tissue Eng, 2003; 9: 1323-1330). Spherical structures were observed, such as spherulites (FIG. 1) forming as the polymer is cured (Cohen Y et al., Acs Sym Ser, 1987; 350:181-98; Sukitpaneenit P et al., J Membrane Sci, 2009; 340:192-205; Teuji H et al., Macromolecules, 1992; 25:2940-2946). Maltese cross patterns were observed under cross-polarized light (FIG. 8).

Incubation time was observed to have no significant effect on microfiber shape and cross-sectional morphology (FIG. 1 panels C and D). Diameters did not change more than 5.0 μm after incubation in PBS for eight weeks. The average microfiber diameters of 0% (control), and 1.0%, 2.4%, and 4.8% (w/w) DXM-loaded samples throughout the degradation analysis were observed to be 62.8±6.8 μm, 65.7±5.8 μm, 65.6±5.8 μm, and 62.9±8.3 μam, respectively. An occasionally large pore was observed among sample cross sections. The overall porosity of fibers did not change with time. At eight weeks of incubation, microfibers had an average percent porosity of 18.3±3.1 and an average pore size area of 1.24±0.09 $\mu m^2$. These data indicate that little PLLA microfiber degradation had occurred during the incubation period.

Example 12

Dexamethasone Encapsulation and In Vitro Release Kinetics

To determine the encapsulation efficiency and drug distribution within wet spun microfibers, two separate regions of microfiber bundles collected from the coagulation bath were assayed. DXM 1.0-4.8% (w/w) was encapsulated with relatively high efficiency (76-93%) as shown in Table 1. DXM and PLLA were dissolved in 6:1 (v/v) DCM to THF before precipitation in the petroleum ether bath. The coagulation rate of fibers was nearly instantaneous, resulting in little overall drug loss during polymer solidification. DXM-loaded microfibers at 4.8% (w/w) were observed to have slightly decreased encapsulation efficiency in comparison to 1.0% and 2.4% (w/w) formulations. The observed decrease with 4.8% (w/w) drug loading was due to obtaining the limit for drug loading of 7.5% (w/v) PLLA microfibers; drug loadings greater than 4.8% (w/w) resulted in significant drug loss as shown with 10% (w/w) theoretical DXM loading in Table 1. For these reasons, formulations with 1.0%, 2.4% and 4.8% (w/w) theoretical loading were used in Examples herein. No significant variations in drug loading were observed among different sampling regions of meter-long microfibers bundles indicating that the drug was homogeneously distributed.

TABLE 1

Encapsulation efficiency of microfibers prepared by wet spinning. Data are represented as mean ± S.D.

| DXM loading of dope solution (% w/w) | DXM loading of wet spun microfiber (% w/w) | DXM encapsulation efficiency (%) |
|---|---|---|
| 1.0 | 0.9 | 89.0 ± 0.036 |
| 2.4 | 2.2 | 92.9 ± 0.084 |
| 4.8 | 3.6 | 75.8 ± 0.002 |
| 10.0 | 1.0 | 9.9 ± 0.010 |

Release profiles of DXM-loaded fibers are shown in FIG. 2 panel A. Each fiber formulation exhibited little burst, followed by linear cumulative percent DXM release starting at day 3 and continuing to eight-week incubation ($R^2$=0.92–1.0). Formulations with 0.9% and 2.2% (w/w) actual DXM loading released less than 1% and 2% of total drug encapsulated during the first three days. In contrast, 3.6% (w/w) DXM-loaded fibers released 5% of total drug encapsulated during the first three days and maintained a faster rate of drug release throughout the course of the analysis. Greater initial release of DXM from 3.6% (w/w) actual drug-loaded fibers was due to drug located near the surface of microfibers. Increased drug loading led to an overall increase in drug release, with lower loadings displaying similar release rates as a function of time. These data indicate that at lower loadings, the drug was well encapsulated within the polymer matrix with little drug near the surfaces of microfibers. The cumulative percent DXM released after eight weeks was 5.54±0.12 for 0.9% (w/w) actual drug loading, 4.62±1.08 for 2.2% (w/w) actual drug loading, and 27.82±5.13 for 3.6% (w/w) actual drug loading.

An absence of morphological changes was observed by scanning electron microscopy. These data indicated that drug release was not predominately controlled by polymer degradation, and rather by dissolution and diffusion of drug into the supernatant. At low loadings, drug release was associated with dissolution of the drug, and at higher loadings, drug release was associated with a combination of dissolution and diffusion. Since the 3.6% (w/w) actual drug-loaded microfibers released 202.5 µg after eight weeks, nearly ten times the amount of drug relative to the 2.2% (w/w) formulation that released 20.6 µg, a significant portion of drug release was due to diffusion. Mack et al. have also studied release of DXM from microfibers (Crow B B et al., Biopolymers, 2006; 81:419-427; Mack B C et al., J Control Release, 2009; 139: 205-211). At eight weeks, wet spun PLGA (50:50) microfibers released 60-90% total encapsulated drug primarily due to polymer degradation. According to the manufacturer, the degradation rate of the raw PLLA used in Examples herein is greater than 24 months. Therefore, the release behavior from microfiber delivery system observed herein over the course of eight-week incubation was predominantly due to the hydrophobic nature of DXM.

The controlled, sustained release of dexamethasone constitutes a clinically important therapeutic modality for biomaterial-driven inflammation. Local, targeted delivery of dexamethasone over extended periods of time (months) reduces immune responses to implanted biomedical devices and polymeric biomaterials (Hickey T et al., J Biomed Mater Res, 2002; 61:180-187; Patil S D et al., Diabetes Technol Ther, 2004; 6:887-897; Dang T T et al., Biomaterials, 2011; 32:4464-4470; Selvam S et al., Biomaterials, 2011; 32:7785-7792). The effective therapeutic ranges of drug evaluated in previous studies ranged from 0.17 to 30 µg/day, depending on the size and material of the implant. The average daily release rates after initial burst for 20 mg microfiber bundles from compositions and methods observed herein were approximately 1-2 µg/day for 0.9 and 2.2% actual DXM loading, and 15 µg/day for 3.6% actual DXM loading. These data indicate an ability to tune DXM release rates within the therapeutic ranges of drug treatment by combining multiple formulations into multifilament yarns and by altering scaffold architecture (Leung V et al., Polym Advan Technol, 2011; 22:350-365). For example, weft-knitted scaffolds use more yarn material in the assembly of macrometric structures and thus are capable of delivering a greater dose of therapeutics than warp-knitted scaffolds of similar dimensions.

Example 13

Supernatant pH Characteristics of DXM-Loaded PLLA Microfibers

Diffusion of PLLA oligomer was analyzed by measuring the supernatant pH over degradation time. Degradation of PLLA (Mathiowitz E., Encyclopedia of controlled drug delivery. New York: Wiley; 1999) yields L(+)-lactic acid, a naturally occurring stereoisomer of lactic acid. The lactic acid monomers from hydrolytic de-esterfication of PLLA enter the carboxylic acid cycle and are excreted as water and carbon dioxide. For this reason PLLA is widely used in drug encapsulation.

The supernatant pH of terminal time points was determined to compare the relative changes of DXM-loaded microfibers in comparison to control microfibers with no drug. Formulations displayed similar decrease in pH (FIG. 2 panel B). At eight-week incubation, 0% (control), 1.0%, 2.4% and 4.8% (w/w) formulations decreased in pH by 0.95, 1.25, 1.56 and 1.37, respectively. Inclusion of DXM potentially increases the hydrophobicity of microfibers, resulting in little pH changes as a function of time. The PBS was not changed and each time point was terminal for this Example only. Crow et al. measured supernatant pH changes as a function of bovine serum albumin (BSA) release from wet spun PLLA microfibers (Crow B B et al., Tissue Eng, 2005; 11:1077-1084) and observed that at 15-week incubation, control microfibers decreased in pH by 1.70, with buffer changes occurring at each time point. Data herein indicated that DXM release from microfiber was not mediated by PLLA degradation.

Example 14

Thermal Analysis of DXM-Loaded PLLA Microfibers

The morphology of blank and degraded microfibers was analyzed using DSC. Representative DSC traces of control microfibers after fabrication and throughout degradation are presented in FIG. 3 panel A. Thermal transitions calculated from the first heating scan are listed in Table 2. It was observed that relative PLLA crystallinity, as a result of wet spinning, was substantially increased. Extrusion of PLLA alone increased relative crystallinity by 17% in comparison to raw polymer from the manufacturer. Drug-loaded microfibers also increased in relative crystallinity by 13-16% after wet spinning. Several factors contributed to this effect, including the solvents, nonsolvent, and residence time during fabrication, leading to SINC (FIG. 4 panel B) (Neogi P., Diffusion in polymers. New York: Marcel Dekker; 1996). Many polymers undergo SINC, and as a polymer (semi-crystalline) is exposed to a solvent between the $T_g$ and the $T_m$, crystallization becomes kinetically favorable. The choice of the solvents and the solubility parameters of solvent [$\delta_{DCM}$=20.2 megapascals$^{1/2}$ (MPa$^{1/2}$), $\delta_{THF}$=18.6 MPa$^{1/2}$] and nonsolvent ($\delta_{PE}$=14.8 MPa$^{1/2}$) in our system affected the rate of solvent removal, solidification, and eventually the degree of crystallinity of PLLA ($\delta_{PLLA}$=20.7 MPa$^{1/2}$) microfilaments. In wet spinning, an initially homogeneous polymer solution is extruded into a coagulation bath that induces phase inversion by counter-diffusion of solvent and nonsolvent. Phase separation of the polymer solution is then initiated and the liquid spin dope stream begins to precipitate into a solid microfilament. In general, it is possible to associate the counter-diffusion of solvent and nonsolvent with the thermodynamic stability of extruded spin dope solutions (Sukitpaneenit P et al., J Membrane Sci, 2009; 340:192-205); the precipitation of polymeric solutions is typically faster with a higher diffusion of solvent in nonsolvent. Wet spun microfibers with similar residence time prepared by Rissanen M et al by phase inverting PLDLA ($\delta_{PLDLA}$=23.3 MPa$^{1/2}$) dissolved in DCM into an ethanol (EtOH) spin bath ($\delta_{EtOH}$=26.6 MPa$^{1/2}$) resulted in a 29% decrease in crystallinity (Rissanen M et al., J Appl Polym Sci, 2009; 113:2683-2692). The difference in the solubility parameter between the solvent/non-solvent, in the last Example, was about 6 units, which indicating that ethanol is a better nonsolvent for the microfiber than petroleum ether. Thus, slower precipitation is optimal for SINC.

No significant differences in glass transition temperature after fabrication were observed between the 1.0% and 2.4% (w/w) DXM-loaded samples in comparison to control microfibers (Table 2). Surprisingly, 4.8% (w/w) DXM-loaded samples showed a slight decrease in glass transition temperature. This indicates that DXM did not act as plasticizer and interacts with the polymer matrix, or that too little drug was present to detect changes in glass transition temperatures. Since there appeared to be little DXM interaction with the amorphous regions of the polymer, as judged by the minor changes in glass transition, Hyper DSC was used to analyze the dispersion of solid drug within wet spun microfibers. Conventional DSC techniques limit the sensitivity to measure the drug melting temperature (Gramaglia D et al., Int J Pharm, 2005; 301:1-5). Slow heating scan rates of 10° C./min allot sufficient time for molecules within the crystal lattice to respond to thermal transitions and further solubilize within the polymer matrix. Hyper DSC uses scanning rates of >100° C./min to inhibit further solubilization of drug within the matrix. Therefore, the fraction of drug solubilized within the matrix does not contribute to the melting endotherm associated with the dispersed drug fraction. Hyper DSC thermograms revealed no melting point at 300° C. for DXM (FIG. 3 panel B), indicating the drug was either amorphous or formed a solid solution within PLLA microfibers and precipitated in an amorphous state. The results of Hyper DSC thermograms indicate that the drug was dispersed at the molecular level since the glass transition of the highest drug loaded fiber, 4.8% was lower than the blank spun fibers. XRD analysis (Example 15) also showed no crystalline content of DXM in the nanoparticles.

TABLE 2

Summary of thermal properties and crystallinity from the first DSC heating scan of degraded microfibers

| Degradation time (weeks) | $T_g$ (° C.) | $T_m$ (° C.) | $\Delta H_m$ (J/g) | $X_c$ (%) |
|---|---|---|---|---|
| Control (0% DXM) | | | | |
| 0 | 57.4 | 174.2 | 60.5 | 64.6 |
| 2 | 61.6 | 174.3 | 60.6 | 64.7 |
| 4 | 63.0 | 174.2 | 60.6 | 64.6 |
| 6 | 63.1 | 174.2 | 60.9 | 65.0 |
| 8 | 64.3 | 173.5 | 59.2 | 63.2 |
| 1% DXM | | | | |
| 0 | 59.5 | 173.7 | 59.2 | 63.2 |
| 2 | 55.9 | 173.4 | 59.2 | 63.1 |
| 4 | 63.3 | 174.7 | 56.0 | 59.8 |
| 6 | 63.8 | 174.0 | 61.1 | 65.2 |
| 8 | 62.2 | 173.9 | 61.4 | 65.5 |
| 2.4% DXM | | | | |
| 0 | 59.7 | 173.4 | 56.4 | 60.1 |
| 2 | 62.9 | 173.3 | 59.0 | 63.0 |
| 4 | 62.6 | 174.2 | 57.8 | 61.7 |
| 6 | 62.4 | 173.9 | 60.8 | 64.9 |
| 8 | 64.4 | 173.5 | 59.8 | 63.8 |
| 4.8% DXM | | | | |
| 0 | 54.3 | 173.7 | 57.0 | 60.8 |
| 2 | 59.4 | 174.0 | 57.5 | 61.4 |
| 4 | 62.2 | 174.0 | 58.9 | 62.8 |
| 6 | 63.2 | 173.4 | 58.4 | 62.4 |
| 8 | 63.6 | 174.0 | 57.9 | 61.8 |
| Unprocessed PLLA | | | | |
| n/a | 52.6 | 174.7 | 44.5 | 47.4 |

$T_g$, glass transition temperature; $T_m$, melting temperature; $\Delta H_m$, endothermic enthalpy of the melting peak; $X_c$, crystallinity degree.

The polymer crystallinity and glass transition temperatures of degraded samples taken from terminal time points were also evaluated using DSC. If major degradation had occurred, the amorphous regions would mostly be expected to disappear, leaving fragmented samples with very high crystallinity. Thus, an increase in crystallinity would be expected. However, DXM-loaded samples were observed to have minimal changes in crystallinity as a function of time, signifying minor polymer degradation.

The glass transition temperature of the microfibers slightly increased with incubation. Table 2. Polymers which are annealed display an increase in glass transition which is related to a reduction in free volume and possibly segmental rearrangement. The glass transition temperature for the second heating scan of the raw polymer was observed to be 47.6° C. Since the glass transition temperature of the second heating scan is close to the incubation temperature (37° C.), the mobility of the polymer chains had increased with incubation time. An increase in chain mobility would result in the formation of crystalline structures (Zong X et al., Biomacromolecules, 2003; 4:416-423). Constrained amorphous chains from thermally induced crystallization resulted in the increase in glass transition temperature with incubation. Secondary DXM-polymer interactions already existing from fabrication would have further increased as some of the polymer degraded. Even minor PLLA degradation during incubation resulted in free carboxylic and hydroxylic groups that are capable of forming secondary interactions with the drug (FIG. 4 panels B and C), contributing to amorphous chain restructuring and a reduction in free volume. Additionally, the specific interactions between PLLA and DXM contributed to the slow release of drug from this delivery system.

Example 15

X-Ray Diffraction (XRD) Analysis of DXM-Loaded PLLA Microfibers

XRD was used to further investigate the physical state of the drug in wet spun microfibers. No crystalline DXM was detected in the four microfiber formulations namely control (0%), 1.0%, 2.4% and 4.8% w/w DXM-loaded PLLA microfibers (FIG. 5). The absence of the specific diffraction of DXM in the x-ray diffractogram of drug-loaded PLLA microfibers demonstrated that DXM was present as either an amorphous drug or as solid solution within the amorphous regions of the polymer (molecular dispersion). Evaluation of the formulations herein showed that control microfibers without drug had a less ordered state than microfibers loaded with drug.

As drug loading was increased a new crystalline peak appeared in the diffraction pattern as shown with 1.0, 2.4, and 4.8% drug loading in FIG. 5. Wet spinning conditions resulted in 13-17% increase in crystallinity of microfibers compared to unprocessed polymer or a control polymer prior to wet spinning (Table 3). Since microfibers had short residence time (5-10 seconds) in the nonsolvent, residual solvent was likely present within the precipitating filament after it was collected from the spin bath. SINC is associated with the increase in the AH, of the blank (control) fibers compared to pure polymer. The change in the PLLA XRD morphology with the drug-loaded samples resulted from the solvent-drug interaction during SING that keeps the glass transition lower for a longer time, thus allowing for further crystallization to take place after the precipitation has started. The control fibers left in the nonsolvent bath for a longer residence time revealed the same third peak (FIG. 9) and the higher degree of crystallinity observed in drug-loaded microfiber formulations described herein.

TABLE 3

Change in crystallinity of polymeric fiber with addition of DXM

| Formulation (% DXM added) | Relative crystallinity (%) | Enhanced crystallinity (%) |
|---|---|---|
| Control polymer prior to wet spinning (0%) | 47.4 | |
| Polymer after wet spinning (0%) | 64.6 | 17.2 |
| (1%) | 63.2 | 15.8 |
| (2.4%) | 60.1 | 12.7 |
| (4.8%) | 60.8 | 13.4 |

Example 16

Mechanical Properties of DXM-Loaded PLLA Microfibers

To characterize the mechanical properties of wet spun micro fibers, samples were loaded in uniaxial tension until failure. The results of mechanical analysis are shown in FIG. 6 and summarized in Table 4. Stress-strain curves for microfibers from each formulation displayed large plastic deformation until failure. Formulations were observed to have similar elastic moduli (FIG. 6 panel A). Differences in ultimate tensile strength (UTS) and the total elongation before tensile failure (strain at failure) were observed between drug-loaded samples compared to control samples without drug. Microfibers with the highest drug loading, 4.8% (w/w) were observed to have the greatest tensile strength (15.6±0.5 MPa) of drug-loaded formulations and were significantly stronger (p<0.01) than control microfibers (FIG. 6 panel B). Drug encapsulation at low loadings, 1.0% and 2.4% (w/w), resulted in similar tensile strengths in comparison to control microfibers. Strain at failure for formulations containing drug was significantly different, with increased drug encapsulation resulting in increased plastic deformation until fracture (FIG. 6 panel C). The highest drug loading, 4.8% (w/w) displayed similar elongation until failure as control microfibers containing no drug.

TABLE 4

Summary of the mechanical properties of wet spun fibers, mean ± SEM

| DXM loading of dope solution (%) | Tensile strength UTS (MPa) | Elastic modulus (MPa) | Strain at Failure mm/mm |
|---|---|---|---|
| 0 | 12.9 ± 0.8 | 195 ± 25.5 | 1.78 ± 0.13 |
| 1.0 | 14.0 ± 0.6 | 215 ± 26.1 | 1.09 ± 0.09 |
| 2.4 | 11.7 ± 0.4 | 204 ± 20.0 | 1.29 ± 0.10 |
| 4.8 | 15.6 ± 0.5 | 213 ± 24.8 | 1.70 ± 0.10 |

Necking during the macroscopic plastic deformation of wet spun microfibers was observed to grow stronger due to the alignment of polymer chains with increasing stress. In semi-crystalline polymers, the amorphous regions of the polymer required less force to deform in comparison to the crystalline regions of the polymer. Increased strength and strain with the 4.8% (w/w) formulation was associated with dexamethasone reinforcing the amorphous regions of the polymer. The process of wet spinning resulted in a marked increase in crystallinity as determined by DSC. Without being limited by any particular theory or mechanism of action, with closely packed and parallel polymer chains, i.e. polymers with increased crystallinity, mechanical strength increased in the presence of drug due to enhanced secondary bonding. During incubation, dexamethasone molecules (392.8 Da) formed secondary interactions within the amorphous phase of the polymer, creating a reinforced composite material (FIG. 4 panel C). With small amounts of encapsulated dexamethasone, the strain was observed to decrease until sufficient drug was encapsulated to exhibit similar strain at failure as control microfibers. Without being limited by any particular theory of mechanism of action it was envisioned that drug particles acted as material defects at low encapsulation loading. Increasing DXM loading increased drug-drug and drug-matrix interactions. Therefore, mechanical properties were influenced by the secondary interactions, namely hydrogen bonds between the polymer lattice and the drug particles.

To further elucidate the effect of drug loading and release on microfibers, mechanical properties were characterized throughout the degradation analysis. Tensile loss profiles of each formulation were generated from stress-strain profiles of terminal time points (FIG. 7 panel A). Microfibers with the highest drug loading, 4.8% (w/w), maintained 97.3% of initial tensile strength and were statistically stronger (p<0.05) after eight weeks in vitro (FIG. 7 panel B). Control, 1.0% and 2.4% (w/w) microfibers were observed to have decreased tensile strength in the first week, and then to have maintained strength. At the end of eight weeks, the breaking strength retention for control, 1.0%, and 2.4% (w/w) was observed to be 80.9%, 80.0%, and 81.3%, respectively. Formulations displayed a decrease in plastic deformation and strain at failure as a function of time (FIG. 7 panel C) independent of drug content, see measurement of the specific heats reported in Table 2. The crystallinity of wet spun microfibers increased as a function of time, causing microfiber embrittlement. Elastic moduli of samples and resistance to deformation under load were conserved as a function of time (FIG. 7 panel D). Dexamethasone drug particles at 4.8% (w/w) were observed to contribute to mechanical strength by secondary bonding adding to physical reinforcement. DXM also was observed to preserve the structure of microfibers as a function of time due to drug stabilizing the lattice, and decreasing the permeation rate due to hydrophobic drug content.

Studies with melt spun PLLA microfibers encapsulating a small anti-inflammatory drug, curcumin (368.4 Da), have also shown preservation of mechanical properties with drug loading (Su S H et al., J Biomat Sci-Polym, E 2005; 16:353-370). Curcumin impregnation at 10% (w/w) increased fiber tensile strength at failure for periods up to 36 days in vitro in comparison to control microfibers with no drug. Although melt spun microfibers produced higher tensile strengths than that of wet spun microfibers in Examples herein, curcumin loaded microfibers maintained only 57% of their initial tensile strength at 25-day incubation. The processing conditions of wet spun microfibers fabricated by Mack et al. also possessed higher initial tensile strength than those used in Examples herein (Mack B C et al., J Control Release, 2009; 139:205-211). However, wet spun microfibers encapsulating levoxithan and dexamethasone lost nearly all of their tensile strength after only 7-day incubation. Data herein show that dexamethasone incorporation increased mechanical integrity as a function of increased microfiber crystallinity. Melt spinning is known to increase crystallinity due to the manner by which polymer chains group themselves in forming a microfiber and therefore curcumin impregnation helped maintain mechanical properties. Conversely, wet spun microfibers fabricated using DMSO and water as solvent and nonsolvent reported no increase in crystallinity and therefore dexamethasone incorporation did not help maintain mechanical strength. Addition of small hydrophobic drugs (<400 Da) increased mechanical integrity of filaments as crystallinity is increased as a result of fabrication. As the proximity of amorphous and crystalline regions increases, so does the possibility for strong secondary interactions between drug and polymer.

Example 17

Microfiber Fabrication for Encapsulating Proteins

Spin dope solutions were prepared using a modified cryogenic emulsion technique (Mathiowitz E et al., Nature, 1997; 386:410-414). PLGA and PLLA microfibers were loaded with a protein: bovine zinc insulin (INS, 5.8 kDa), lysozyme (LZ, 14.3 kDa), or bovine serum albumin (BSA, 66.0 kDa). Protein in ultra-pure water 0.5 mL (20 mg mL$^{-1}$) was added to 10 mL of polymer in DCM (50 mg mL$^{-1}$), yielding an aqueous to organic phase ratio of 1:20. This two-phase system was vortexed for 60 s to create a meta-stable emulsion. The emulsion was frozen in liquid nitrogen, creating frozen protein droplets dispersed in frozen dichloromethane/polymer solid solution. The frozen emulsion was lyophilized for 48 h at −100° C. This process resulted in proteins particles imbedded in a matrix of a polymer of less than 2 μm. The W/O (water/oil) emulsion micronization method showed that most proteins have a solid size <2 μm at the end of the process regardless of the nature of the protein (reference here is to the physical size of the particle, not the molecular weight of the protein) (Mathiowitz E et al., United States Patent. USA: Brown University Research Foundation; 2006).

The dried polymer and protein product was reconstituted in 2.5 mL DCM at a concentration of 200 mg mL$^{-1}$ and placed into a gas-tight glass syringe fitted with a 22-gauge spinneret. A syringe pump was used to extrude the spin dope solution (0.02-0.06 mL min$^{-1}$) into petroleum ether at a solvent to nonsolvent ratio of 1:400, which resulted in the continuous formation of PLGA and PLLA monofilaments. PLGA formulations required 50 μL of Span 85 to prevent gelation around the spinneret during extrusion. Extruded microfibers were collected from the coagulation bath after the spin dope was extruded (about 1.5 h residence time). Blank microfibers were also fabricated and used as controls. Duplicate batches of each formulation were made and analyzed to ensure the reproducibility and uniformity of release profiles.

Example 18

Analysis of Protein Loaded Microfibers by Scanning Electron Microscopy

Scanning electron microscopy was used to analyze cross-sectional and surface morphology of wet spun microfibers. Lyophilized microfibers were mounted on adhesive metal stubs and sputter-coated with a 50-100 Å layer of gold-palladium (Emitech). Samples were viewed with a Hitachi 5-2700 scanning electron microscope using an accelerating voltage of 8 kV. Micrographs were taken using a Quartz PCI digital imaging system. To determine average cross-sectional area, microfibers were arranged into bundles onto paraffin film and rolled laterally into cylindrical tubes and orthogonally cut into thin discs. Five fields of view (15-22 filaments) of cross-sectioned microfibers were captured at 350× magnification and analyzed using ImageJ software (NIH).

Formulations were observed to have a phase inversion of about 2-4 cm from the spinneret tip, forming a continuous solid white monofilament. Microfibers were observed to have consistent size, and similar cross-sectional area, porosity, and porous interconnectivity. Blank and protein-loaded PLGA microfibers were observed to have lobed 'dog-bone' shape with an average height of 46 μm and width of 105 μm (FIG. 10). Blank and protein-loaded PLLA formulations displayed lobed 'kidney' shape with an average height of 50 μam and width of 102 μam (FIG. 11).

Example 19

Thermal Analysis of Protein Loaded Microfibers by DSC

DSC was used to analyze the thermal properties of PLGA and PLLA microfibers after fabrication (day 0) and the incubation period (day 63). DSC measurements of blank and protein-loaded microfibers after fabrication (day 0) and incubation (day 63) were conducted using a DSC-7 (Perkin Elmer) equipped with an Intracooler 2 intercooling system. Samples were subjected to: cooling to −25° C., heating to 250° C. at 10° C. min', cooling to −25° C. at 10° C. min$^1$, and then reheating to the upper limit again at the initial rate. The crystallinity ($X_c$) of PLLA microfibers was calculated using $$X_c = \frac{\Delta H_m}{93.7} \times 100 \quad (5)$$

in which 93.7 J g$^{-1}$ is the specific heat of melting of a 100% crystalline PLLA (Fischer E W et al., Kolloid Z Z Polym, 1973; 251:980-990).

Representative DSC curves of control PLGA and PLLA microfibers after fabrication and after 63-day incubation are presented in FIG. 12. Table 5 summarizes the thermal transitions of wet spun microfibers from the first DSC heating scan. The glass transition temperature ($T_g$) of blank PLGA microfibers was 40.7° C. The $T_g$ of microfibers slightly increased (1.3-3.7° C.) with protein loading. After 63-day incubation, the PLGA formulations, including blank microfibers exhibited an increase in $T_g$ in the range of 2.4-5.0° C.

TABLE 5

Summary or the thermal properties from an initial DSC heating scan of wet spun microfibers upon fabrication (0 days) and after incubation (63 days). Data are expressed as mean ± S.D. (n = 2).

| Microfiber | Time | $T_g$ (° C.) | $T_m$ (° C.) | $\Delta H_m$ (J g$^{-1}$) | $X_c$ (%) |
|---|---|---|---|---|---|
| PLGA | | | | | |
| Blank | t = 0 | 40.7 ± 0.5 | — | — | — |
|  | t = 63 | 45.3 ± 1.1 | — | — | — |
| INS | t = 0 | 44.4 ± 3.8 | — | — | — |
|  | t = 63 | 46.8 ± 0.6 | — | — | — |
| LZ | t = 0 | 42.4 ± 1.9 | — | — | — |
|  | t = 63 | 47.4 ± 0.7 | — | — | — |
| BSA | t = 0 | 42.0 ± 1.5 | — | — | — |
|  | t = 63 | 46.3 ± 0.4 | — | — | — |
| PLLA | | | | | |
| Blank | t = 0 | 42.1 ± 2.2 | 173.0 ± 0.1 | 24.6 ± 2.4 | 26.2 ± 2.6 |
|  | t = 63 | 58.2 ± 0.7 | 173.3 ± 1.5 | 28.6 ± 1.0 | 30.5 ± 1.1 |
| INS | t = 0 | 40.8 ± 0.4 | 173.0 ± 1.5 | 27.5 ± 0.4 | 29.4 ± 0.4 |
|  | t = 63 | 59.1 ± 0.5 | 172.0 ± 0.6 | 27.5 ± 0.3 | 29.3 ± 0.3 |
| LZ | t = 0 | 42.4 ± 2.5 | 173.0 ± 1.4 | 27.0 ± 0.5 | 28.8 ± 0.5 |
|  | t = 63 | 58.9 ± 0.7 | 172.0 ± 0.0 | 28.4 ± 1.7 | 30.3 ± 1.8 |
| BSA | t = 0 | 40.7 ± 0.6 | 173.3 ± 1.3 | 24.3 ± 0.6 | 25.9 ± 0.6 |
|  | t = 63 | 59.2 ± 0.5 | 171.3 ± 0.6 | 28.4 ± 0.3 | 30.3 ± 0.3 |

Control (blank) PLLA microfibers were observed to have a $T_g$ of 42.1° C., with a $T_m$ of 173.0° C., and relative crystallinity of 26.2%. The $T_g$ of INS- and BSA-loaded microfibers was observed to be slightly decreased by 1.3° C. and 1.4° C. compared to the control; LZ microfibers were similar to the control. A minor increase in relative crystallinity (2.6-3.2%) was observed with INS and LZ-loaded PLLA microfibers compared to blank PLLA microfibers. BSA-loaded microfibers were observed to have the lowest relative crystallinity of 25.9% and $T_g$ of 40.7° C. In contrast to PLGA, PLLA (63 day) microfibers were observed to have substantially increased $T_g$ of about 16.1 to 18.5° C. PLLA microfibers also were observed to have a slight increase in percent relative crystallinity; blank microfibers and BSA-loaded microfibers were observed to have the greatest increase in percent relative crystallinity of 4.3% and 4.4%, respectively. The $T_m$ for microfibers formulated with PLLA was maintained at an unchanged level during the incubation period.

Example 20

X-Ray Diffraction (XRD) Analysis of Protein Loaded Microfibers

XRD was used to determine the crystalline structure of PLLA microfibers. The structural properties of PLLA formulations at the initial time point and at 63 days of incubation were also determined using an automated X-ray diffractometer (Siemens Diffraktometer D5000) with a Cu Kα ($\lambda$=1.54 Å) radiation. Diffraction was measured at diffraction angles (2θ) between 6° and 60° with sampling intervals of 0.02 s$^{-1}$. Diffraction signal intensity was monitored and processed using DiffracPlus Software (Bruker AXS).

X-ray scattering patterns of control (blank) and protein-loaded microfibers before (day 0) and after incubation (63 days) showed two small peaks (13.0° and 17.6°) and one large peak)(24.4° for PLLA microfibers (FIG. 13 panel A). After incubation in PBS at 37° C. for 63 days, the diffraction peak at 24.4° was no longer observed and a new diffraction peak between 16-17° was present, which was significantly enhanced for protein-loaded samples (FIG. 13 panel B).

Example 21

Mechanical Testing of Protein Loaded Microfibers

To determine the effect of protein loading and molecular weight on the mechanical properties of PLGA and PLLA wet spun microfibers, samples were loaded under uniaxial tension until failure. Uniaxial tensile tests were conducted using a materials testing system (Instron Model 4442) in accordance to the United States Pharmacopeia absorbable suture testing standard (United States Pharmacopeia and National Formulary (USP 34-NF 29, Rockville, Md.: United States Pharmacopeial Convention; 2010). Microfibers and yarns were secured to a paper frame (25 mm×25 mm) and loaded into the crosshead clamps of the machine. Prior to loading, the sides of the paper template were cut leaving the sample intact. An elongation rate of 50 mm min$^{-1}$ was applied until failure. The resulting load-displacement data collected by the digital acquisition system was converted to stress-strain data to calculate the ultimate tensile strength (UTS), percent strain to failure, and elastic modulus. The mechanical properties of microfibers were compared in SPSS v.19 (Chicago, Ill.) using ANOVA. Analyses for multiple comparisons were carried out using the Tukey multiple comparisons test. A p value of less than 0.05 was considered statistically significant.

Since microfibers were non-circular, the average cross-sectional areas were calculated from scanning electron microscopy images for mechanical analyses. The mechanical strength of blank PLLA microfibers was observed to be greater than control (blank) PLGA microfibers (FIG. 14). Blank PLLA microfibers were observed to have an average load to failure of 176.4±3.8 millinewtons (mN) and ultimate tensile strength of 43.2±0.9 MPa, compared to blank/control PLGA microfibers that were observed to have an average load to failure of 118.6±14.0 mN and ultimate tensile strength of 32.7±3.8 MPa (FIG. 14 panels A and B). Significant variations in the strain to failure and elastic modulus were also observed among blank formulations. PLGA microfibers had a strain to failure of 12±6% in comparison to PLLA microfibers with a strain to failure of 3±1% (FIG. 14 panel C). PLGA microfibers had an average elastic modulus of 569.7±61.7 MPa whereas PLLA microfibers had an average elastic modulus of 822.4±93.3 MPa (FIG. 14 panel D).

TABLE 6

Protein release from 2% (w/w) loaded microfibers

| Microfiber | Molecular weight (kDa) | Actual loading (%) | Encapsulation efficiency (%) | First phase duration and release | Second (lag) phase duration and release | Third phase duration and release | Total released (%) |
|---|---|---|---|---|---|---|---|
| PLGA | | | | | | | |
| INS | 5.8 | 0.83 | 41.6 | 14 days 57.9% | 14-42 days 8.7% | 42-63 days 14.7% | 81.3 |
| LZ | 14.3 | 0.85 | 42.7 | 21 days 40.4% | 21-63 days 7.1% | None | 47.5 |
| BSA | 66.0 | 0.61 | 30.5 | 21 days 28.1% | 21-63 days 12.3% | None | 40.5 |
| PLLA | | | | | | | |
| INS | 5.8 | 1.46 | 73.0 | 14 days 13.4% | 14-35 days 0.7% | 35-63 days 4.4% | 18.5 |
| LZ | 14.3 | 1.39 | 69.2 | 14 days 4.5% | 14-63 days 3.9% | None | 8.4 |
| BSA | 66.0 | 1.24 | 61.8 | 14 days 3.4% | 14-63 days 1.7% | None | 5.1 | non-Fickian transport, n = 0.89 to case II (relaxational) transport, and n > 0.89 to super case II Protein encapsulation was observed to surprisingly alter the material properties of both PLGA and PLLA microfibers. Protein-loaded microfibers within the same polymer type had significantly lower (p<0.05) load to failure and ultimate tensile strength compared to blank controls (FIG. 14 panels A and B). Among protein-loaded formulations, BSA-loaded PLGA and PLLA microfibers possessed significantly lower (p<0.05) load to failure and ultimate tensile strength compared to INS and LZ-loaded formulations. However, no statistical differences in load to failure and ultimate tensile strength were observed between INS and LZ-loaded PLGA formulations.

Significant differences in strain at failure were also observed within PLGA and PLLA formulations (FIG. 14 panel C). The failure extensions of protein-loaded PLGA microfibers were statistically lower than blank PLGA microfibers (p=0.000). LZ and BSA-loaded PLLA microfibers also had statistically lower elongation until failure compared to blank PLLA microfibers. INS-loading did not significantly decrease the ductility of PLLA microfibers (p=0.659). An exponential relationship was found between parameter of the strain to failure and molecular weight of the protein that was encapsulated in microfibers for each of PLGA ($R^2$=0.9880) and PLLA ($R^2$=−0.9800). No statistical differences in elastic moduli were observed among PLGA formulations (FIG. 14 panel D). However, BSA-loaded PLLA microfibers were observed to have significantly lower elastic modulus in comparison to blank, INS-loaded and LZ-Loaded formulations.

Example 22

Analysis of Protein Release from Microfiber Formulations

To determine protein release kinetics, triplicate samples (10 mg) from each batch were suspended in 1.5 mL of PBS (pH 7.4) in capped microcentrifuge tubes and incubated at 37° C. At each time point, 1 mL of the releasate was removed and replaced with fresh PBS. The pH of the release buffer was 7.2-7.4 throughout the incubation period. The protein concentration of releasates and corresponding protein standards in PBS (1.6-25 µg mL$^{-1}$) were determined using a micro BCA assay kit. Samples and corresponding standards were read at 562 nm. In vitro analyses were performed in triplicate from duplicate batches of each formulation. The release profiles are expressed as the cumulative percent release from each formulation, normalized to the amount of encapsulated protein. Microfibers from each formulation were immersed in 0.1 N NaOH (Sigma St. Louis, Mo.) and incubated at 37° C. until fully dissolved. The encapsulation efficiency was calculated as the actual amount of protein detected with the micro BCA assay relative to the theoretical amount of protein added to spin dope solutions prior to wet spinning.

The data obtained from in vitro protein release was fitted to the Korsmeyer-Peppas kinetic model to determine the mechanism of release. Korsmeyer et al. derived a simple relationship to describe diffusion based drug release from a polymeric system given by $$\frac{M_t}{M_\infty} = kt^n \tag{6}$$

in which $$\frac{M_t}{M_\infty}$$

is a fraction of drug released at time t, k is the release rate constant, and n is the release exponent (Korsmeyer R W et al., Macromolecular and modeling aspects of swelling controlled system. In: Roseman T J, Mansdorf S Z, editors. Controlled release delivery systems. New York: M. Dekker; 1983, 77-101). In this model, the n value is used to characterize the release mechanism. For a cylindrical matrix, n<0.45 corresponds to Fickian diffusion, 0.45<n<0.89 to transport. Data were plotted as log cumulative percentage drug release as a function of log time for the first 60% of drug released.

Three phases of release from microfiber formulations were observed (Table 6). During the first phase, protein release was fastest for INS, followed by LZ and BSA for PLGA formulations (FIG. 15 panel A). Similar patterns were observed for PLLA formulations, but at significantly lower cumulative release percentages (FIG. 15 panel B). The duration of the first phase was characterized by a typical diffusion profile and was found to be dependent on protein molecular weight. For PLGA microfibers, this phase lasted for 14 days for INS, and 21 days for LZ and BSA. The first phase of INS, LZ and BSA release from PLLA fibers was 14 days. A second phase, characterized by slow, linear release was also observed for the PLGA and PLLA formulations. The duration of this phase for INS was 28 days and 21 days for PLGA and PLLA formulations, respectively. LZ and BSA PLGA formulations were observed to have a second phase of 42 days; PLLA formulations were observed to have a second phase of 49 days. A third phase with additional protein release was observed with INS formulations, which lasted 21 days for PLGA and 28 days for PLLA formulations.

To determine the mechanism of protein release from microfibers, in vitro release data were fitted to the Korsmeyer-Peppas kinetic model. The regression coefficient ($R^2$) and release constant (k) values from the release data for each formulation were calculated as shown in Table 7. The regression coefficients for Korsmeyer-Peppas plots were observed to be in a range from 0.9684 to 0.9865. Cumulative protein release (%) of encapsulated proteins from PLGA and PLLA fibers at days one and day 38 after fabrication as a function of protein molecular weight is shown in FIG. 15 panels C-F. Release kinetics from PGLA fibers was observed to decrease exponentially with increased protein molecular weight ($R^2$=0.91-0.98). PLLA fibers having encapsulated proteins exhibited sustained release rates independent of molecular weight during the course of 38 days.

TABLE 7

Release parameters of protein-loaded microfibers

| Microfiber | Korsmeyer-Peppas | | |
|---|---|---|---|
|  | $k(t^{-n})$ | n | $R^2$ |
| PLGA |  |  |  |
| INS | 0.1281 | 0.2805 | 0.9865 |
| LZ | 0.0461 | 0.3430 | 0.9730 |
| BSA | 0.0325 | 0.3419 | 0.9868 |
| PLLA |  |  |  |
| INS | 0.0252 | 0.2708 | 0.9862 |
| LZ | 0.0137 | 0.3180 | 0.9653 |
| BSA | 0.0131 | 0.2441 | 0.9684 |

Example 23

Fourier Transform-Infrared (FT-IR) Spectroscopy Analysis

FT-IR analysis was performed after microfiber fabrication and after 63 days of incubation using a Perkin Elmer (Wellesley, Mass.) Spectrum Once B spectrophotometer with a zinc-selenide (ZnSE) universal attenuated total reflectance (ATR) attachment. Microfibers (2-3 mg) were analyzed in the region between 4000-650 $cm^{-1}$ with a resolution of 2 $cm^{-1}$. FT-IR spectra were taken at the beginning and end points of release to characterize the relative degradation of incubated microfibers. Average spectra from PLGA and PLLA microfiber formulations after fabrication (0 days) and at 63 days of incubation are shown in FIG. 16. The FT-IR spectra remained unchanged throughout the degradation analysis. The three observed absorption peaks characteristic of the Ester bonds are the ester aliphatic C=O stretch at 1750 $cm^{-1}$, aliphatic ester C—O stretch at 1260 $cm^{-1}$, and the v(C—C) mode of the C—COO of the polymer chain at 860 $cm^{-1}$. These peaks were observed to be undiminished at 63 days of incubation. No appearance of peaks indicative of lactic and glycolic acid i.e. the carboxylic acid v(C=O) stretch at 1700 $cm^{-1}$ and the wide v(O—H) bend at 3200 $cm^{-1}$ was observed;

Example 24

Microencapsulation Efficiencies

Microencapsulation efficiencies of protein loaded microfibers were determined (Table 6). PLGA formulations were observed to have lower average loading efficiencies of 38.3±6.7% compared to PLLA efficiencies of 68.0±5.7%. Protein loss is attributed to protein adsorption to conical tubes during the micronization process and differences in spin dope precipitation strength during phase inversion. PLLA solutions precipitated visibly faster than PLGA solutions, accounting for increased encapsulation efficiency among PLLA formulations. A reduced protein loss is envisioned in scale-up to larger batch sizes.

Example 25

Single Step Fabrication of Wet Spun Binary Phase Composite Microfibers

A single step method to fabricate a polymeric microfiber delivery system for controlled delivery of therapeutics and minimal initial burst is described using phase separated binary blends of PLLA and PLGA (75:25 ester terminated), which were wet spun by phase inversion. Polarized light microscopy, DSC, scanning electron microscopy and fluorescence microscopy were used to assess formation of composite microfibers.

To determine the conditions for phase separation of PLLA and PLGA solutions, 20% w/v 1:1, 1:2, and 1:3 w/w ratios of each of the polymers were made in DCM. Solutions were mixed for 1 h and were incubated to equilibrate for 24 h. The appearance of two phases was observed by a difference in color between the polymer solutions. Films were cast from the liquid-liquid phase separated solutions. Upon verification of liquid phase separation of polymer solutions by polarized light microscopy PLLA/PLGA microfibers were wet spun by phase inversion. Polymers were dissolved in DCM in appropriate w/w ratios. The phase separated polymer solution was loaded into a glass syringe fitted with a 22 gauge spinneret and placed in a syringe pump. Since DCM is miscible with petroleum ether, the immersion of the spinneret into the coagulation bath resulted in the continuous precipitation of monofilament microfibers.

A typical micrograph of a phase separated PLLA:PLGA solution is shown in FIG. 17, in which the micrograph PLLA spherulites are visible within the continuous PLGA phase. The phase separation of 1:1, 1:2 and 1:3 PLLA:PLGA solutions was observed under cross polarized optical microscopy. The 1:1 spin dope solution was thus determined to be suitable for wet spinning. The inherent viscosity and molecular weight of 1:2 and 1:3 phase separated solutions was found to be too low to fabricate continuous monofilaments within the spin bath.

DSC thermograms exhibited the presence of two glass transitions in the first heating scan of PLLA:PLGA (1:1) microfibers (FIG. 18 panel A). The presence of two glass transitions, each representative of PLLA and PLGA controls, is evidence of a phase separated blend. If the solution were a miscible blend of PLLA and PLGA, the thermal properties would be between those of the two unblended polymers. Analysis of cumulative release kinetics of PLGA, PLLA and PLLA:PLGA (1:1) microfibers loaded with BSA showed that fibers with PLLA:PLGA (1:1) exhibited a reduced burst effect compared to fibers of PLGA or PLLA (FIG. 21 panel A).

No apparent differences in the cross-sectional morphology of binary phase PLLA:PLGA (1:1) microfibers were observed compared to fibers of PLLA and PLGA (FIG. 19). FITC-dextran was encapsulated to analyze the ability to localize potential therapeutics within binary phase composite microfibers. Localization of FITC dextran within the PLLA phase of the composite microfiber was observed by fluorescence microscopy (FIG. 20).

The ability to localize drug to an inner core of composite microfibers is useful for controlling spatiotemporal release of therapeutics from small diameter monofilament delivery systems. Composite microfibers, unlike double-walled microspheres, do not exhibit distinct core-shell morphology. Double-walled microspheres are made by solvent removal and solvent evaporation, a process that takes several hours before microspheres are fully precipitated. Wet spinning by phase inversion is a nearly instantaneous process controlled by solvent and nonsolvent miscibility. Phase separated spin dope solutions did not fully separate during microfiber precipitation and PLLA regions were solidified with the continuous PLGA phase (FIG. 21 panel B, drawing to the right).

Example 25

Fiber Spinning

Biodegradable fibers were spun by phase inversion using a wet spinning system (FIG. 22). In wet spinning, an initially homogeneous polymer solution is extruded into a coagulation bath that induces phase inversion by counter-diffusion of solvent and nonsolvent (FIG. 22 panel A). As a result phase separation is initiated of the polymer solution into two phases, a polymer lean and polymer rich phase. Phase separation of polymers continues during the period of time the fiber is incubated in the coagulation bath. This time duration is referred to as the residence time. In wet spinning the parameters of size, shape, morphology, and strength of wet spun filaments, contribute to mechanical strength and drug delivery attributes, and these parameters depend on factors including polymer concentration, solubility of polymer in solvent, solvent/nonsolvent miscibility parameters, residence time, and fiber drawing methods.

To spin fibers, spin dope solutions of polymer formulations dissolved in DCM were added to a 5 mL pump-controlled syringe fitted with a 22-gauge spinneret. Spin dope solutions were extruded into a nonsolvent coagulation bath resulting in the rapid de-solvation of liquid polymer streams and continuous formation of monofilaments (FIG. 22 panel A). Different spin dope solutions were investigated. For encapsulation of DXM, 10% and 20% (w/v) solution compositions were fabricated from blends of PLLA, PLGA and PVP in co-solvent mixtures of 6:1 (v/v) DCM to THF. A co-solvent mixture was used to increase solubility of DXM in spin dope solutions. Fibers were extruded at 0.02-1.2 mL min$^{-1}$ into petroleum ether, 2-propanol, or mixtures thereof and were collected from the spin bath using one of the following methods: fibers were either left in the bath throughout the extrusion process (as-spun); drawn from the bath during extrusion (solution-drawn); or were removed from the spin bath and wound around metal bobbins under tension (post-drawn). Each of these processes was developed to determine the applicability of wet spun fibers for designing hybrid devices.

Example 26

Multifilament Yarn Production

Single fibers were used to produce multifilament yarns. Monofilaments were fabricated by extruding spin dope solutions of PLLA, PLGA, and PVP into a 50:50 (v/v) mixture of 2-propanol to petroleum ether coagulation bath for 1.5 min. Addition of 2-propanol was determined to be suitable for some formulations to overcome coagulation around the spinneret tip by slowing the rate of precipitation for the formation of continuous fibers. Fibers were cured for four minutes, and were removed from the spin bath and placed in an empty beaker. Samples were untangled and wound around metal bobbins (post-drawn) on a rotating mandrel positioned above the beaker. To create 6-ply yarns, six bobbins, four monofilaments of a 10% (w/v) polymer composite formulation 'A' and 2 monofilaments of a 20% (w/v) composite formulation 'B' were placed on a winding mandrel (pattern B, A, A, A, A, B). Monofilament fibers were grouped together using a surgical clamp and twisted along the longitudinal axis in the 'Z' direction (filament inclination from top right to bottom left) to create 30-inch multifilament yarns (FIG. 22 panel B). Yarns were wound around an empty bobbin and stored at −20° C.

Example 27

Scanning Electron Microscopy of Monofilaments of Different Wet Spun Formulations Representative samples of each formulation were evaluated by scanning electron microscopy. Samples were mounted on adhesive metal stubs and sputter-coated with a 50-100 Å layer of gold-palladium (Emitech, Kent, England). Micrographs were taken with a Hitachi S-2700 (Tokyo, Japan) at an accelerating voltage of 8 kV using a Quartz PCI digital imaging system. To determine the average diameter of microfilaments and yarns, five fields of view were obtained at 100× and 35×, respectively. The average porosity of cross-sectioned fibers was also determined from five fields of view at 1,300×. Micrographs were analyzed using NIH ImageJ software (Bethasda, Md.). Porosity was calculated as the pore area divided by the total cross-sectional area. Results of scanning electron microscopy of wet spun monofilaments of different formulations showed diverse surface features (FIG. 23).

Example 28

Dexamethasone Release Analysis

The polymer compositions of DXM-loaded formulations are shown in Table 8. Monofilaments and multifilament yarns (triplicate samples, 10 mg each) were incubated in 1.4 mL of phosphate buffered saline (PBS) at 37° C. At each time point, 1.0 mL of the releasate was removed and replaced with fresh PBS. Amounts of DXM released from individual fibers and multifilament yarns were quantified by UV absorption at 239 nm. A 96-well quartz plate was used to minimize background at the reading frequency. Drug concentration was determined by comparing absorbance values to standards of known DXM concentration. Polymer composition was observed to modulate drug release kinetics of DXM-loaded monofilaments (FIG. 26).

TABLE 8

Wet spun fiber formulations with DXM loading

| | Polymer composition (% w/w) | | | |
|---|---|---|---|---|
| | PLLA | PLGA | PLLA$_{0.94}$ | PVP |
| Solution-drawn 10% solution | | | | |
| SF-10a | 95 | 5 | — | — |
| SF-10b | 94 | 5 | — | 1 |
| SF-10c | 95 | — | 5 | — |
| SF-10d | 94 | — | 5 | 1 |
| SF-10e | 99 | — | — | 1 |
| As-spun 20% solution | | | | |
| SF-20a | 50 | 50 | — | — |
| SF-20b | 67 | 33 | — | — |
| SF-20c | 75 | 25 | — | — |
| SF-20d | 80 | 20 | — | — |
| Post-drawn 10% solution | | | | |
| SF-10 formulation 'A' Post-drawn 20% solution | 94 | 5 | — | 1 |

Example 29

Engineering Fibers with Desired Release Kinetics from Multifilament Yarns

The release kinetics of multifilament yarns were predicted from the experimental release of individual monofilaments. For a multifilament yarn, the theoretical release as a function of release time, t was calculated according to $$\text{Theoretical Release } (t) = f_A R_A(t) + f_B R_B(t) \tag{7}$$

in which f is the fraction of fibers from any given formulation relative to the total number of discrete monofilaments included in the yarn, and R is the amount of drug released from individual formulations as a function of release time, t. This equation is applied to number of individual formulations twisted to create multifilament drug-eluting yarns.

Example 30

In Vitro Bioactivity of Dexamethasone Released from Multifilament Yarns

Human aortic valve interstitial cells (hVICs) isolated from human cryopreserved conduits passage 2 through 4, (from the Cardiac Regenerative Surgery Research Laboratory, Children's Mercy Hospital) were used for in vitro analyses. Cells were maintained in hVIC media, Dulbecco's Modified Eagle's Medium (DMEM F12, Gibco) supplemented with 10% fetal bovine serum (FBS, Gibco), 1% L-glutamine, 1% penicillin/streptomyocin, and 1% amphotericin B. The biological activity of eluted DXM was determined using a cell proliferation assay (Reil T D et al., J Surg Res, 1999; 85:109-114). Passage 5 hVICs were plated with 10% FBS growth media at 5000 cells/cm$^2$ into collagen type I coated 12-well plates (BD BioCoat, San Jose Calif.) and cultured for 24 h. Cell growth was arrested by washing plates with PBS and adding 1% FBS serum starvation media. Growth arrest was maintained for 48 h to allow for cell cycle synchronization. Synchronized cells were then re-stimulated with 10% FBS growth media containing $10^{-7}$ mol/L DXM. DXM-supplemented growth media was made using eluted DXM releasates from multifilament yarns at 1-day and 56-day incubation. Fresh, unencapsulated drug and PBS vehicle were used as controls. The media for each experimental group was changed every 24 h continuing to a total exposure of 72 h. Results of the bioactivity of DXM released from multifilament yarns are shown in FIG. 28.

Example 31

Mechanical Testing

Uniaxial tensile tests were conducted using a materials testing system (Instron Model 4442) in accordance to the United States Pharmacopeia (USP) absorbable suture testing standards (United States Pharmacopeia and National Formulary (USP 34-NF 29), United States Pharmacopeial Convention, Rockville, Md., 2010). Monofilaments and yarns were secured to a paper frame (25 mm×25 mm) and loaded into the crosshead clamps of the machine. Prior to loading, the sides of the paper template were cut and the sample was maintained intact. An elongation rate of 50 mm min$^{-1}$ was applied until failure, and load-displacement data was collected by digital acquisition system. Load at break is a measure of elongation until fiber fracture. The ductility or strain at failure ($\epsilon = \Delta L L o - 1$) is calculated from the original gauge length (Lo) and the change in gauge length ($\Delta L$) as recorded by crosshead movement until fiber fracture. Ten replicates of each formulation were analyzed. Results of mechanical testing are shown in Table 9.

Example 32

Statistical Analysis

Statistical analysis was performed using SPSS v.19 statistical software (Chicago, Ill.). All data are expressed as mean±S.D. An ANOVA and a post hoc Tukey multiple comparisons test were used for group comparisons. To determine the significance of theoretical multifilament yarn drug release in comparison to experimental release, a two-tailed t-test was performed. A p value of less than 0.05 was considered statistically significant.

Example 33

Morphology of Wet Spun Monofilaments

Fibers were fabricated by applying post-handling techniques, varying spin dope precipitation strengths, and altering the solvent/nonsolvent miscibility parameters and were observed to have diverse surface structures. For example, as-spun PLGA fibers extruded into petroleum ether were characterized by a smooth surface morphology (FIG. 23 panels A and B). Conversely, solution-drawn PLLA$_{0.94}$ fibers extruded into a mixture of 2-propanol and petroleum ether and stretched under tension as the dope solution precipitated were characterized by longitudinal grooves along the direction of fiber drawing (FIG. 23 panels C and D). Fibers spun from high and low solution concentrations and extruded under otherwise identical conditions also resulted in diverse surface architectures. Initiation of gelation of fibers wet spun from 10% (w/v) PLLA (FIG. 23 panel E) was observed to be slower than that of 15% (w/v) PLLA (FIG. 23 panel F) fibers since there was more solvent volume to diffuse into the petroleum ether coagulation bath. Similarly, changing the molecular weight of the polymer solution was observed to alter the surface morphology of wet spun filaments. High molecular weight PLLA (FIG. 23 panel G) solutions were characterized by smoother surface structures compared to lower molecular weight PLLA$_{0.94}$ (FIG. 23 panel H) solutions spun under identical conditions. Altering the nonsolvent bath composition was observed to result in a change in the surface roughness of wet spun filaments. Composite spin dope solutions extruded into petroleum ether displayed smooth surface topography (FIG. 23 panel I), and the same solution extruded into a 50:50 mixture of 2-propanol to petroleum ether possessed surfaces with micron-rough grooves and spherical protrusions (FIG. 23 panel J). Solutions precipitated visibly slower in 2-propanol than petroleum ether. The changes observed in the rate of precipitation were a direct result of the solvent system used. The solubility parameter of DCM (δDCM=20.2 MPa½) is 5.5 units higher than petroleum ether (PE) (δPE=14.8 MPa½) and 3.6 units from 2-propanol (2-P) (δ2-P=23.8 MPa½), indicating that petroleum ether is a better nonsolvent for the polymer. Thus, the onset of precipitation was faster with petroleum ether and a smooth surface morphology was obtained.

Composite formulations selected for multifilament yarn production further demonstrated the diverse effects of processing conditions on surface structure and cross-sectional morphology of wet spun filaments. Post-drawn 10% (w/v) composite fiber surfaces were observed to have longitudinal striations with many spherulites (FIG. 24 panels A and C) compared to 20% (w/v) composite fibers having nano-porous surfaces and fewer spherulites (FIG. 24 panels E, G). The cross-sectional porosity of composite fibers was also significantly different. The porosity of 10% and 20% (w/v) composite fibers was observed to be 3.0±1.8 μm$^2$ and 9.1±2.8 μm$^2$, respectively.

Example 34

Drug Release Kinetics of as-Spun and Solution-Drawn Monofilaments

To investigate the effect of polymer composition and concentration on DXM release, the kinetics of drug release from composite monofilaments of 10% and 20% (w/v) polymer concentrations were determined. Polymer concentrations were selected based on mechanical characteristics of blank as-spun PLLA fibers (FIG. 25). Initial release analyses were terminated at 35 days in vitro to mimic the timeline of acute and chronic phases of wound healing.

The cumulative DXM release from 10% (w/v) composite monofilaments loaded with 2.5% (w/w) DXM is shown in FIG. 26 panel A. Each formulation exhibited an initial burst release from the first day of incubation, followed by a continuous linear release to 35 days. The initial release of drug was fastest from fibers prepared with more hydrophilic polymers. PLLA/PLGA/PVP composite fibers (SF-10b) were observed to have the highest initial burst of 5.5±0.7 μg mg$^{-1}$ of fibers, and the other formulations each exhibited a similar initial drug burst release of 2.5±0.5 μg mg$^{-1}$ of fibers.

The release kinetics of 20% (w/v) composite fibers loaded with 1.5% (w/w) actual DXM are shown in FIG. 26 panel B. Composite fibers were formulated from ratios of 1:1 (SF-20a), 1:2 (SF-20b), 1:3 (SF-20c), and 1:4 (SF-20d) PLGA to PLLA (20-50% PLGA content). Fibers prepared from 20% (w/v) spin dope solutions were observed to exhibit significantly different release kinetics compared to fibers wet spun from 10% (w/v) polymer solutions. PLGA/PLLA formulations prepared from 20% (w/v) spin dope solutions exhibited very little burst (<3% encapsulated DXM) within the first day of incubation, with a presence of PLGA to the extent of 50% fiber composition. Each formulation was observed to have a similar lag phase to 14-day incubation. At this phase, the formulation having 50% PLGA content showed a marked increase in release rate. At 35 days, the cumulative drug release was 13.6±2.7 μg mg$^{-1}$ of fibers (78% encapsulated DXM) for 1:1; 2.3±0.2 μg mg$^{-1}$ of fibers (21% encapsulated DXM) for 1:2; 1.7±0.7 μg mg$^{-1}$ of fibers (12% encapsulated DXM) for 1:3; and 1.8±0.8 μg mg$^{-1}$ of fibers (12% encapsulated DXM) for 1:4 PLGA/PLLA formulations. Drug release from 20% (w/v) polymer solutions with 50% PLGA content was observed to significantly increase compared to amount of the initial burst. PLLA/PLGA/PVP (SF-10b) and PLLA/PLGA (SF-10a) exhibited the greatest overall drug release (50% and 60% encapsulated DXM) with average daily release rates of 1.1 μg mg$^{-1}$ and 1.8 μg mg$^{-1}$ of fibers, respectively. PLLA/PVP (SF-10e), PLLA/PLLA$_{0.94}$/PVP (SF-10d), and PLLA/PLLA$_{0.94}$ (SF-10c) formulations released 24-29% total encapsulated drug and were observed to have a similar daily release rates of 0.6-0.7 μg mg$^{-1}$ of fibers.

Example 35

Drug Release Kinetics of Post-Drawn Composite Monofilaments and 'Z' Twisted Multifilament Yarns Drug-eluting wet spun microfilaments were engineered into macro-structured implants. Crystalline regions of PLLA were observed herein to contribute to mechanical strength, and to potentially decrease the rate of drug release. A linear release of up to 28% total encapsulated DXM was observed (Example 12, FIG. 27) from PLLA fibers incubated for eight weeks in vitro, and therapeutic levels of DXM from wet spun fibers using a low (7.5%) PLLA concentration were achieved. To increase the rate of release of DXM from higher PLLA concentrations (10% and 20% w/v) composite fibers with the addition of a lower molecular weight PLLA, amorphous PLGA, and water-soluble polymer PVP were formulated.

Monofilaments used for yarn fabrication were spun from 10% and 20% (w/v) concentrations. Polymer blends were selected to achieve therapeutic ranges of DXM treatment (Table 8). The PLGA and PVP content was increased for formulation of the 20% (w/v) composite fibers to further modulate release. The release kinetics of post-drawn monofilaments are shown in FIG. 27 panel A. Monofilaments spun from 10% (w/v) composite fibers loaded with 2.8% actual DXM were observed to have substantially less burst release compared to 20% (w/v) polymer solutions formulated with 2.4% actual DXM.

After the initial burst phase, fibers made from 10% (w/v) fibers exhibited linear release rates ($R^2$=0.98) in comparison to 20% (w/v) solutions, which exhibited logarithmic drug release ($R^2$=0.96) up to 56 days in vitro. The average daily release after the initial burst for composite solutions was 0.7 μg mg$^{-1}$ for 10% (w/v) fibers. For 20% (w/v) fibers, the average daily release up to 21-day incubation was 1.8 μg mg$^{-1}$, followed by a release rate of 0.2 μg mg$^1$. At 56-day incubation, 10% (w/v) formulations released 11.6±0.4 μg mg$^{-1}$ of fibers (21% encapsulated DXM), and 20% (w/v) formulations released 17.2±0.4 μg mg$^{-1}$ of fibers (36% encapsulated DXM).

Post-drawn fibers are potentially useful for tailoring release of therapeutics from medical implants by the formation of multifilament yarns. Yarns produced from several different combinations of single fibers are envisioned to achieve desired release profiles for specific clinical applications including sequential release of multiple small molecules or therapeutics. FIG. 27 panel B shows release profiles predicted from the experimental release of single fibers in FIG. 27 panel A using equation 7 for five different theoretical 6-ply yarns. The experimental DXM release from a 6-ply multifilament yarn formulation was evaluated. The release kinetics of 6-ply multifilament yarns produced by 'Z' twisting four single filaments of formulation 'A', with two single filaments of formulation 'B' (Table 8) were observed to have release profiles within the ranges of individual filaments (FIG. 27 panel C). Yarns released 5.3 µg mg$^{-1}$ (15% encapsulated DXM) in an initial burst release after one day of incubation, followed by an average daily release of 0.8 µg mg$^{-1}$ from day 1 to day 56 incubation. By day 56 of incubation, yarns released a total of 12.4±1 mg$^{-1}$ (35% encapsulated DXM). Good agreement was observed between the experimental drug release and the theoretical prediction. Release samples at the measured time points except days 14 and 28 were not statistically different (p<0.05) than the predicted release, suggesting monofilament twisting did not affect the release kinetics of constituent monofilaments. Therefore, with respect to drug release, fabrication of multifilament yarn from monofilament yarn did not affect linearity of release.

Example 36

Biological Activity of Eluted Dexamethasone from Multifilament Yarns

The effect of dexamethasone released from multifilament yarns on the proliferation of hVICs was studied to evaluate the biological activity of eluted drug. The proliferation of hVICs cultured in the presence of DXM-supplemented media from multifilament yarns that had been incubated for 1 day, and 56 days in comparison to control media was determined (FIG. 28). The hVICs cultured in the presence of medium that contained DXM proliferated at a significantly reduced rate after 72 hours compared to control cells with PBS vehicle. Proliferation of hVICs grown in medium that contained either fresh or eluted DXM were similar. These findings confirmed that wet spinning did not alter the biological activity of encapsulated DXM since each of eluted and unencapsulated DXM treatment was observed to affect the growth and proliferation of hVICs to the same extent.

Example 37

Mechanical Properties of Post-Drawn Monofilaments and 'Z' Twisted Multifilament Yarns The tensile properties of wet spun fibers wound around metal bobbins were evaluated to analyze the effects of post-drawing and multifilament yarn production on filament breaking strength and ductility. A summary of the tensile properties of single filaments (SF) and twisted (TW) 6-ply yarns is shown in Table 9. After fabrication, blank and drug-loaded monofilaments were observed to have a slight increase in load to failure as a function of increasing the polymer concentration from 10% to 20% (w/v). Addition of DXM into wet spun monofilaments did not significantly reduce the breaking strength of fibers, unlike other studies encapsulating drugs within wet spun fibers (Chang H I et al., J Biomed Mater Res Part A, 2008; 84:230-237; Mack B C et al., J Control Release, 2009; 139:205-211; Rissanen M., J Appl Polym Sci, 2010; 116:2174-2180). The ductility of 10% and 20% (w/v) blank (p=0.061) and drug-loaded (p=0.155) were similar. DXM-loaded and blank multifilament yarns possessed a fivefold increase (p=0.000) in load bearing capacity compared to individual DXM-loaded and blank fibers. The marked increase in load at failure correlated well with the summation of the failure strength of individual monofilaments. The ductility of yarns was significantly reduced (p<0.05) compared to individual blank and drug-loaded fiber formulations, indicating that monofilament twisting removed a portion of the strain within constituent monofilaments.

TABLE 9

Summary of tensile properties of post-drawn monofilaments and 'Z' twisted multifilament yarns. Data are represented as mean ± S.D. (n = 10)

| Sample type | Diameter (µm) | Load at failure (mN) | Strain at failure (mm/mm) |
|---|---|---|---|
| SF-10$_{blank}$ | 49.5 ± 7.9 | 64.3 ± 7.7 | 2.10 ± 0.59 |
| SF-20$_{blank}$ | 70.2 ± 7.9 | 89.9 ± 8.7 | 1.48 ± 0.72 |
| TW$_{blank}$ | 152.1 ± 6.3 | 341.5 ± 27.1 | 1.34 ± 0.35 |
| SF-10 | 48.4 ± 6.6 | 71.0 ± 8.7 | 2.55 ± 0.51 |
| SF-20 | 64.6 ± 6.9 | 77.3 ± 3.6 | 2.12 ± 0.59 |
| TW | 153.9 ± 7.5 | 447.1 ± 40.9 | 1.16 ± 0.40 |

Example 38

Handling Capabilities of 'Z' Twisted Multifilament Yarns

To scale up of microfilaments into complex structures, single microfilaments were grouped together and twisted into multifilament yarns. Six fibers were twisted in the 'Z' direction for the formation of 6-ply multifilament yarns. Twisted fibers were scaled to a thickness of around 150 µm with even entwining and small spaces between single fibers (FIG. 22 panel B). The handling capabilities of multifilament yarns were observed to have improved compared to constituent monofilaments. Yarns were capable of being readily braided, knitted or woven into complex geometries (FIG. 29).

What is claimed is:

1. A wet spun microfiber composition comprising at least one polymer wherein the composition comprises:
   a porous polymeric microstructure obtained by solvent induced crystallization (SINC), wherein the polymer is at least one selected from: poly-1-lactic acid (PLLA), poly-lactic-co-glycolide (PLGA), polyvinylpyrrolidone (PVP); and further comprises at least one encapsulated therapeutic agent, the polymer is dissolved in an organic solvent and the therapeutic agent is dispersed with the polymer in the organic solvent to produce a polymer-therapeutic agent solution, and the polymer-therapeutic agent solution is wet spun by extrusion in a non-solvent bath, provided that the non-solvent bath is not water, to obtain the wet spun microstructure; wherein the therapeutic agent is located in the microstructure and is controllably releasable from the composition, and wherein following evaporation of the solvent and the non-solvent the microfiber composition has a degree of crystallinity at least 10% greater than that of control polymer prior to wet spinning.

2. The composition according to claim 1 having a structure selected from the group of: a fiber, a suture, a sphere, an implant, and a scaffold.

3. The composition according to claim 2, wherein an encapsulated first therapeutic agent comprises dexamethasone.

4. The composition according to claim 3, further comprising an encapsulated second therapeutic agent.

5. The composition according to claim 4, wherein the second therapeutic agent comprises at least one selected from the group: a drug; a protein; a peptide; a sugar; a carbohydrate; and a nucleotide sequence.

6. The composition according to claim 5, wherein the protein comprises at least one selected from the group: a growth factor, an immunoglobulin, an enzyme, and a peptide antibiotic.

7. The composition according to claim 5, wherein the nucleotide sequence comprises a vector.

8. The composition according to claim 4, wherein the second therapeutic agent is a Nog (Noggin).

9. The microfiber composition according to claim 1, wherein the composition comprises at least about 75% of the initial tensile strength for at least about five weeks.

10. A kit for treating a subject having a medical condition comprising:
  a wet spun microfiber composition having at least one polymer selected from: poly-1-lactic acid (PLLA), poly-lactic-co-glycolide (PLGA), polyvinylpyrrolidone (PVP); wherein the composition comprises a porous polymeric microstructure obtained by solvent induced crystallization (SINC), and further comprises at least one encapsulated therapeutic agent, the polymer is dissolved in an organic solvent and the therapeutic agent is dispersed with the polymer in the organic solvent to produce a polymer-therapeutic agent solution, and the polymer-therapeutic agent solution is wet spun by extrusion in a non-solvent bath, provided that the non-solvent bath is not water, to obtain the wet spun microstructure; wherein the therapeutic agent is located in the microstructure and is controllably releasable from the composition, and wherein the microfiber composition has a degree of crystallinity at least 10% greater than that of control polymer prior to wet spinning;
  instructions for use; and,
  a container.

11. The kit according to claim 10 wherein a first therapeutic agent is dexamethasone.

12. The kit according to claim 10 further comprising a second therapeutic agent.

13. The kit according to claim 12, wherein the second therapeutic agent comprises at least one selected from the group: a sugar; a carbohydrate; a nucleotide sequence; a protein selected from the group of: a growth factor, an immunoglobulin, an enzyme, and an antibiotic; and a drug selected from the group comprising: an anti-apoptotic; an immunosuppressant; a pro-apoptotic; an anti-coagulant; an anti-tumor; an anti-viral; an anti-bacterial; an anti-mycobacterial; an anti-fungal; an anti-proliferative; an anti-inflammatory; and a steroid selected from the group of: a cortisone compound, a dexamethasone, a sex-related hormone; and a non-steroidal anti-inflammatory agent (NSAID).

14. The kit according to claim 13, wherein the nucleotide sequences comprises a vector.

15. The kit according to claim 10 wherein the composition has a structure selected from the group of: a fiber, a suture, a sphere, an implant, and a scaffold.

16. A device for treating a tissue comprising:
  at least one microstructure polymer obtained by solvent induced crystallization (SINC), and a composition, wherein the polymer secures or binds the tissue and is selected from the group of: a suture, a strand, a fiber, a filament, and a thread; wherein the polymer is a biocompatible ester compound and is at least one selected from: poly-1-lactic acid (PLLA), poly-lactic-co-glycolide (PLGA), polyvinylpyrrolidone (PVP); and the composition contains at least one therapeutic agent that forms a complex with the polymer; wherein the polymer is dissolved in an organic solvent and the therapeutic agent is dispersed in with the polymer in the organic solvent to produce a polymer-therapeutic agent solution, and the polymer-therapeutic agent solution is wet spun by extrusion in a non-solvent bath, provided that the non-solvent bath is not water, resulting in the wet spun microstructure; and is characterized by controllable release from the polymer.

17. The device according to claim 16 wherein the polymer comprises plurality of polymers.

18. The device according to claim 17 wherein the plurality of polymers is interlinked or bound closely together, wherein the plurality of polymers forms a structure selected from the group of: a screen, a fabric, a scaffold, a yarn, an implant, and a mesh.

19. The device according to claim 16, wherein the polymer is further characterized by at least one property selected from the group of: crystalline, amorphous, bio-resorbable, porous, elastic, and sterile.

20. The device according to claim 16, wherein the composition further comprises an additional agent that modulates strength or elasticity of the polymer, or that modulates release of the therapeutic agent from the device.

21. The device according to claim 20, wherein the polymer comprises a water-soluble polymer.

22. The device according to claim 21, wherein the polymer comprises an internal structure that is crystalline, amorphous, or a combination thereof.

23. The device according to claim 22, wherein the therapeutic agent comprises at least one of the group selected from: a low molecular weight drug, a glucosteroid, a steroid hormone, a protein, a peptide, a sugar, a carbohydrate, and a nucleotide sequence.

24. The device according to claim 22, wherein the therapeutic agent comprises at least one selected from the group of: a lysozyme, an insulin, dexamethasone, a noggin.

25. The device according to claim 22, wherein the therapeutic agent is at least one selected from the group consisting of: an anti-tumor, an antiviral, an antibacterial, an anti-inflammatory, an anti-mycobacterial, an anti-fungal, an anti-proliferative, an anti-apoptotic, and a bone morphogenic protein antagonist.

26. The device according to claim 25, wherein the polymer contacts the tissue and releases the therapeutic agent and treats or remediates a defect or a condition of cells of the tissue, wherein the tissue is selected from the group of: epithelial, endothelial, vascular, nerve, muscle, cartilage, and bone.

* * * * *